(12) United States Patent
Davis et al.

(10) Patent No.: US 12,227,512 B2
(45) Date of Patent: *Feb. 18, 2025

(54) BENZIMIDAZOLES AND METHODS OF USING SAME

(71) Applicant: University of Utah Research Foundation, Salt Lake City, UT (US)

(72) Inventors: Darrell Davis, Salt Lake City, UT (US); Shuanghu Liu, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/388,765

(22) Filed: Nov. 10, 2023

(65) Prior Publication Data

US 2024/0116944 A1    Apr. 11, 2024

Related U.S. Application Data

(60) Division of application No. 17/732,447, filed on Apr. 28, 2022, now abandoned, which is a continuation of application No. 17/023,323, filed on Sep. 16, 2020, now Pat. No. 11,339,173.

(60) Provisional application No. 63/013,473, filed on Apr. 21, 2020, provisional application No. 62/901,678, filed on Sep. 17, 2019.

(51) Int. Cl.
| | |
|---|---|
| C07D 491/147 | (2006.01) |
| C07D 235/30 | (2006.01) |
| C07D 487/04 | (2006.01) |
| C07D 491/048 | (2006.01) |
| C07D 491/052 | (2006.01) |
| C07D 495/14 | (2006.01) |

(52) U.S. Cl.
CPC ....... *C07D 491/147* (2013.01); *C07D 235/30* (2013.01); *C07D 487/04* (2013.01); *C07D 491/048* (2013.01); *C07D 491/052* (2013.01); *C07D 495/14* (2013.01)

(58) Field of Classification Search
None
See application file for complete search history.

(56) References Cited

U.S. PATENT DOCUMENTS

| 7,642,265 B2 | 1/2010 | Seth et al. |
|---|---|---|
| 2005/0165007 A1 | 7/2005 | Seth et al. |
| 2013/0136782 A1 | 5/2013 | Blackwell et al. |
| 2016/0046625 A1 | 2/2016 | Boezio et al. |
| 2017/0252277 A1 | 9/2017 | Staudigel |
| 2018/0265827 A1 | 9/2018 | Oh et al. |

FOREIGN PATENT DOCUMENTS

| BR | 1120220049102 | 9/2020 |
|---|---|---|
| CA | 3151327 | 9/2020 |
| CN | 202080076047 | 9/2020 |
| EP | 20864318 | 9/2020 |
| IL | 29136022 | 9/2020 |
| IN | 202217022264 | 9/2020 |
| JP | 2022517376 | 9/2020 |
| KR | 20220085774 | 9/2020 |
| MX | 2022003160 | 9/2020 |
| WO | WO 2004/050035 | 6/2004 |
| WO | WO 2012/018668 | 2/2012 |
| WO | WO 2013/050241 | 4/2013 |
| WO | WO2019/072515 | 4/2019 |
| WO | WO2019/177716 | 9/2019 |
| WO | WO 2019/069269 | 11/2019 |
| WO | WO US2020/051133 | 9/2020 |

OTHER PUBLICATIONS

International Search Report and Written Opinion mailed on Feb. 4, 2021 by the International Searching Authority for International Application No. PCT/US2020/51133, filed on Sep. 16, 2020 (Applicant—University of Utah Research Foundation) (12 Pages).
Pubchem CID 59127223, Create Date: Aug. 20, 2012.
Biron KK et al. Potent and selective inhibition of human cytomegalovirus replication by 1263W94, a benzimidazole L-riboside with a unique mode of action. Antimicrob Agents Chemother. Aug. 2002;46(8):2365-72.
Bryant ML et al. Antiviral L-nucleosides specific for hepatitis B virus infection. Antimicrob Agents Chemother. Jan. 2001;45(1):229-35.
Bucknall RA. The effects of substituted benzimidazoles on the growth of viruses and the nucleic acid metabolism of host cells. J Gen Virol. Jan. 1967;1(1):89-99.
Burton DE et al. 2-trifluoromethylbenzimidazoles: a new class of herbicidal compounds. Nature. Dec. 18, 1965;208(5016):1166-9.
Chen YL et al. Activation of peripheral blood mononuclear cells by dengue virus infection depotentiates balapiravir. J Virol. Feb. 2014;88(3):1740-7.
Filbin ME, Kieft JS. HCV IRES domain IIb affects the configuration of coding RNA in the 40S subunit's decoding groove. RNA. Jul. 2011;17(7):1258-73.
García LL et al. Inhibitors compounds of the flavivirus replication process. Virol J. May 15, 2017;14(1):95.

(Continued)

*Primary Examiner* — Samantha L Shterengarts
(74) *Attorney, Agent, or Firm* — Ballard Spahr LLP

(57) ABSTRACT

The present disclosure is concerned with benzimidazole compounds and methods of using these compounds for the treatment of hepatitis (e.g., hepatitis C), RNA virus infections (e.g., Zika virus, dengue virus, Powassan virus, Chikungunya virus, Enterovirus, respiratory syntactical virus (RSV), Rift Valley fever, Influenza virus, Tacaribe virus, Mayaro virus, West Nile virus, yellow fever virus, and coronavirus), and disorders of uncontrolled cellular proliferation (e.g., cancer). This abstract is intended as a scanning tool for purposes of searching in the particular art and is not intended to be limiting of the present invention.

12 Claims, 23 Drawing Sheets

(56) References Cited

OTHER PUBLICATIONS

Gumina G et al. L-Nucleosides as chemotherapeutic agents. FEMS Microbiol Lett. Aug. 7, 2001;202(1):9-15.
Gumina G et al. L-nucleosides: antiviral activity and molecular mechanism. Curr Top Med Chem. Oct. 2002;2(10):1065-86.
Low JG et al. Efficacy and safety of celgosivir in patients with dengue fever (CELADEN): a phase 1b, randomised, double-blind, placebo-controlled, proof-of-concept trial. Lancet Infect Dis. Aug. 2014;14(8):706-715.
Mathé C, Gosselin G. L-nucleoside enantiomers as antivirals drugs: a mini-review. Antiviral Res. Sep. 2006;71(2-3):276-81.
O'Hare T et al. In vitro activity of Bcr-Abl inhibitors AMN107 and BMS-354825 against clinically relevant imatinib-resistant Abl kinase domain mutants. Cancer Res. Jun. 1, 2005;65(11):4500-5.
Roth H et al. Flavivirus Infection Uncouples Translation Suppression from Cellular Stress Responses. mBio. Jan. 10, 2017;8(1):e02150-16.
Sehgal PB et al. Early Ad-2 transcription units: only promoter-proximal RNA continues to be made in the presence of DRB. Virology. Apr. 15, 1979;94(1):185-91.
Seth PP et al. SAR by MS: discovery of a new class of RNA-binding small molecules for the hepatitis C virus: internal ribosome entry site IIA subdomain. J Med Chem. Nov. 17, 2005;48(23):7099-102.
Stefańska JZ et al. Antimicrobial activity of substituted azoles and their nucleosides. Pharmazie. Dec. 1999;54(12):879-84.
Stoneley M et al. Analysis of the c-myc IRES; a potential role for cell-type specific trans-acting factors and the nuclear compartment. Nucleic Acids Res. Feb. 1, 2000;28(3):687-94.
Tamm I, Sehgal PB. Halobenzimidazole ribosides and RNA synthesis of cells and viruses. Adv Virus Res. 1978;22:187-258.
Tamm I et al. Short capped hnRNA precursor chains in HeLa cells: continued synthesis in the presence of 5,6-dichloro-1-beta-D-ribofuranosylbenzimidazole. Biochemistry. Jun. 10, 1980;19(12):2743-8.
Tamm I, Ribonucleic Acid Synthesis and Influenza Virus Multiplication. Science 1957, vol. 126, p. 1235 (Abstract).
Townsend LB et al. Design, synthesis, and antiviral activity of certain 2,5,6-trihalo-1-(beta-D-ribofuranosyl)benzimidazoles. J Med Chem. Sep. 29, 1995;38(20):4098-105.
Tunçbilek M et al. Synthesis and antimicrobial activity of some new anilino benzimidazoles. Arch Pharm (Weinheim). Dec. 1997;330(12):372-6.
Wang P et al. Recent advances in L-nucleosides: chemistry and biology. Antiviral Res. Dec. 1998;40(1-2):19-44.
Wang QY et al. A translation inhibitor that suppresses dengue virus in vitro and in vivo. Antimicrob Agents Chemother. Sep. 2011;55(9):4072-80.
Warren TK et al. Protection against filovirus diseases by a novel broad-spectrum nucleoside analogue BCX4430. Nature. Apr. 17, 2014;508(7496):402-5.
"New hair care and skin care polymers from Ashland deliver improved performance", Focus on Surfactants, Elsevier, Amsterdam, NL, vol. 2010, No. 6, Jun. 1, 2010 (Jun. 1, 2010), pp. 4, XP027079457, ISSN: 1351-4210, [retrieved on Jun. 1, 2010], DOI: 10.1016/S1351-4210(10)70138-4.
Paulsen et al. (2010) "Inhibitor-induced structural change in the HCV IRES domain IIa RNA," *Proceedings of the National Academy of Sciences* 107(16): 7263-7268.
Database Registry Chemical Abstracts Service, Columbus, Ohio, Accession No. RN 1232594-91-0. Entered STN: Jul. 16, 2010.
U.S. Appl. No. 17/732,4470 (US 2022/0275001), filed Apr. 28, 2022 (Sep. 1, 2022), Darrell Davis (University of Utah Research Foundation).
U.S. Appl. No. 17/023,323 (U.S. Pat. No. 11,339,173), filed Jun. 16, 2020 (May 24, 2022), Darrell Davis (University of Utah Research Foundation).
U.S. Appl. No. 63/013,473, filed Apr. 21, 2020, Darrell Davis (University of Utah Research Foundation).
U.S. Appl. No. 62/901,678, filed Sep. 17, 2019, Darrell Davis (University of Utah Research Foundation).
Liu S, et al., Measuring antiviral activity of benzimidazole molecules that alter IRES RNA structure with an infectious hepatitis C virus chimera expressing Renilla luciferase. Antiviral Res. Jan. 2011;89(1):54-63.
Seth PP, et al., SAR by MS: discovery of a new class of RNA-binding small molecules for the hepatitis C virus: internal ribosome entry site IIA subdomain. J Med Chem. Nov. 1, 20057;48(23):7099-102.

| Table 1. E2 Antiviral Activity for RNA Viruses | | | |
|---|---|---|---|
| Virus | Cell Line | DD011-E2 $EC_{50}$ (µM) | DD011-E1 $EC_{50}$ (µM) |
| SARS-CoV-2 | VeroE6 | 0.142 | ~20 |
| Zika (Flavi) | Vero | 0.04 | 6.5 |
| Dengue-2 (Flavi) | Huh7 | 0.32 | 0.88 |
| Powassan (Flavi) | Huh7 (Sec) | 0.12 | 1.2 |
| Yellow Fever (Flavi) | Huh7 | 0.32 | 3.2 |
| West Nile (Flavi) | Huh7 | 0.32 | 3.2 |
| Chikungunya (Toga) | Huh7(Sec) | 0.58 | 15 |
| EEEV (Toga) | Vero (Sec) | 0.21 | 12 |
| WEEV (Toga) | Vero (Sec) | 0.6 | 32 |
| VEEV (Toga) | Vero | 0.32 | 32 |
| Mayaro (Toga) | Vero | <0.1 | 32 |
| RVFV (Bunya) | Huh7(Sec) | 0.48 | 4.6 |
| Tacaribe (Arena) | Vero | 0.32 | 31 |

FIG. 1

Structure of JQ1

BENZIMIDAZOLES AND METHODS OF USING SAME

CROSS-REFERENCE TO RELATED APPLICATIONS

This application is a Divisional of U.S. application Ser. No. 17/732,447, filed Apr. 28, 2022, which is a Continuation of U.S. application Ser. No. 17/023,323, filed Sep. 16, 2020, which claims priority to U.S. Provisional Application Ser. No. 62/901,678, filed Sep. 17, 2019, and U.S. Provisional Application Ser. No. 63/013,473, filed Apr. 21, 2020, the contents of each of which are incorporated herein by reference in their entireties.

STATEMENT REGARDING FEDERALLY SPONSORED RESEARCH

This invention was made with government support under grant no. AI108104, awarded by the National Institutes of Health. The government has certain rights in the invention.

BACKGROUND

The benzimidazole core system is an integral part of numerous antiparasitic, fungicidal, anthelmintic, and anti-inflammatory drugs (Tuncbilek et al. (1997) *Arch. Pharm.* 330: 372; Burton et al. (1965) *Nature* (London) 208: 1166). In addition, modified benzimidacole nucleosides have also been found to be biologically active (Stefanska et al. (1999) *Pharmazie* 54: 879; Townsend et al. (1995) *J. Med. Chem.* 38: 4098; North et al. (2004) *Antimicrob. Agents Chemother.* 48: 2760). For example, 5,6-dichlorobenzimidazole ribonucleoside (DRB) inhibits cellular and viral RNA synthesis (Tamm, I. (1957) *Science* 126: 1235; Sehgal et al. (1979) *Virology* 94: 185; Tamm et al. (1980) *Biochemistry* 19: 2743). However, this activity is accompanied by a substantial cytotoxicity and, therefore, this compound has not found application as an antiviral drug (Tamm and Sehgal (1978) *Adv. Virus Res.* 22: 187; Bucknall, R. A. (1967) *J Gen. Virol.* 1:89).

More recently, the L-ribonucleoside of 5,6-dichloro-2-isopropylaminobenzimidazole (1263W94) was found to show increased activity against the herpes virus HCMV (human cytomegalovirus) in vitro compared to its parent compound 2-bromo-5,6-dichloro-1-β-D-ribofuranosylbenzimidazole (BDCRB) and also to have a low cytotoxicity (Biron et al. (2002) *Antimicrob. Agents Chemother.* 46: 2365). Without wishing to be bound by theory, this appears to be in line with the general observation that several L-nucleosides exhibit an antiviral activity comparable and sometimes greater than their D-enantiomers, due to a more favorable toxicological profile and a greater metabolic stability (Gumina et al. (2002) *Curr. Top. Med. Chem.* 2:1065; Gumina et al. (2001) *FEMS Microb. Lett.* 202:9). Thus, various L-nucleosides have been synthesized as potential antiviral and anticancer drugs such as, for example, 3TC (lamivudine), FTC (emtricitabine), and L-FMAU (clevudine). (Gumina et al. (2002) *Curr. Top. Med. Chem.* 2:1065; Gumina et al. (2001) *FEMS Microb. Lett.* 202:9; Wang et al. (1998) *Antiviral Res.* 40:19; Bryant et al. (2001) *Antimicrob. Agents Chemother.* 45: 229; Mathe and Gosselin (2006) *Antiviral Res.* 71: 276).

The widespread applicability of benzimidazole analogs continues to make them attractive pharmaceutical targets. Thus, there remains a need for novel benzimidazole analogs and methods of making and using same. In addition, known benzimidazole analogs may have applicability for other disorders and conditions not yet recognized. These needs and others are met by the present invention.

SUMMARY

In accordance with the purpose(s) of the invention, as embodied and broadly described herein, the invention, in one aspect, relates to compounds and compositions for use in the prevention and treatment of hepatitis (e.g., hepatitis C), RNA virus infections (e.g., Zika virus, dengue virus, Powassan virus, Chikungunya virus, Enterovirus, respiratory syntactical virus (RSV), Rift Valley fever, Influenza virus, Tacaribe virus, Mayaro virus, Mayaro virus, West Nile virus, yellow fever virus, and coronavirus), and disorders of uncontrolled cellular proliferation (e.g., cancer).

Thus, disclosed are compounds having a structure represented by a formula selected from:

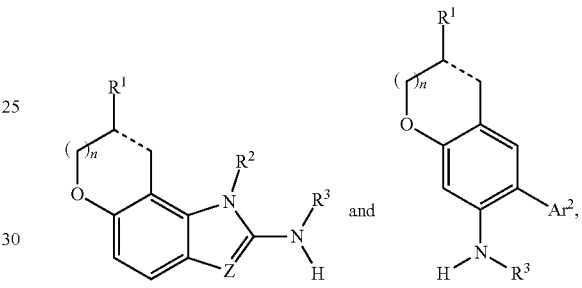

wherein ⌇ is a single or a double covalent bond; wherein n is 0 or 1; wherein Z, when present, is selected from N and $CR^{10}$; wherein $R^{10}$, when present, is selected from hydrogen and halogen; wherein $R^1$ is selected from —(C1-C4 alkyl) $OR^{11}$, —(C1-C4 alkyl)$NR^{12a}R^{12b}$, —$CO_2R^{13}$, and —C(O) $NR^{14a}R^{14b}$; wherein each of $R^{11}$, $R^{12a}$, and $R^{12b}$, when present, is independently selected from hydrogen, C1-C4 alkyl, —C(=NH)$NH_2$, —$CO_2$(C1-C4 alkyl), —(C1-C4 alkyl)$OR^{20}$, —(C1-C4 alkyl)$NR^{21a}R^{21b}$, —(C1-C4 alkyl) $Ar^1$, and $Ar^1$; wherein $Ar^1$, when present, is selected from aryl and heteroaryl and substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of $R^{13}$, $R^{14a}$, and $R^{14b}$, when present, is independently selected from hydrogen and C1-C4 alkyl; wherein $R^2$, when present, is selected from C1-C4 alkyl and —(C1-C4 alkyl)$NR^{15a}R^{15b}$; wherein each of $R^{15a}$ and $R^{15b}$, when present, is independently selected from hydrogen and C1-C4 alkyl; wherein $R^3$ is selected from hydrogen and C1-C4 alkyl; or wherein each of $R^2$, when present, and $R^3$ together comprise a 5- to 6-membered heterocycle substituted with a group selected from C1-C4 alkyl and —(C1-C4 alkyl)$NR^{16a}R^{16b}$; wherein each of $R^{16a}$ and $R^{16b}$, when present, is independently selected from hydrogen and C1-C4 alkyl; and wherein $Ar^2$ is a heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, provided that when the compound has a structure represented by a formula:

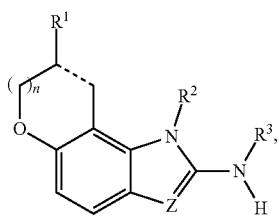

then either ⁀ is a double bond, Z is CR$^{10}$, or R$^2$ is C1-C4 alkyl, or a pharmaceutically acceptable salt thereof.

Also disclosed are compounds selected from:

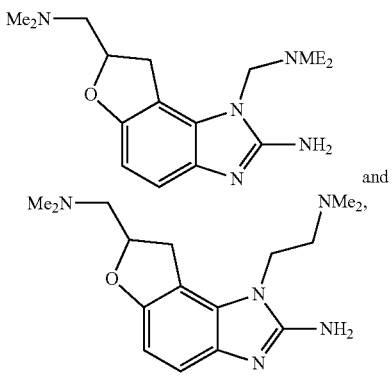

or a pharmaceutically acceptable salt thereof.

Also disclosed are pharmaceutical compositions comprising a therapeutically effective amount of a disclosed compound and a pharmaceutically acceptable carrier.

Also disclosed are methods for modulating hepatitis viral translation in a subject, the method comprising administering to the subject an effective amount of a disclosed compound.

Also disclosed are methods for modulating hepatitis viral translation in at least one cell, the method comprising contacting the cell with an effective amount of a disclosed compound.

Also disclosed are methods for treating hepatitis in a subject, the method comprising administering to the subject an effective amount of a disclosed compound.

Also disclosed are kits comprising a disclosed compound, and one or more of: (a) at least one agent known for the treatment of hepatitis; (b) instructions for administering the compound in connection with hepatitis; and (c) instructions for treating hepatitis.

Also disclosed are methods for modulating translation of a RNA virus in a subject, the method comprising administering to the subject an effective amount of a compound having a structure represented by a formula selected from:

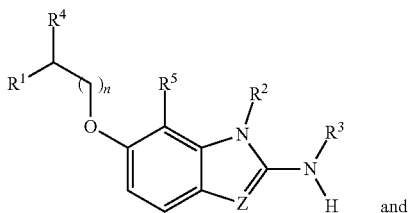
and

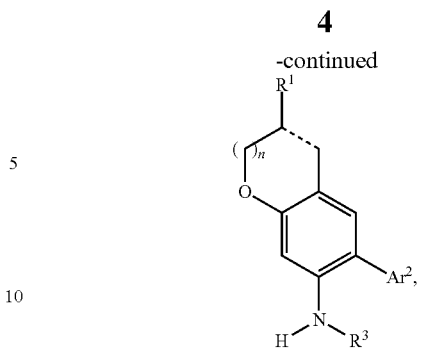

wherein ⁀ is a single or a double covalent bond; wherein n is 0 or 1; wherein Z, when present, is selected from N and CR$^{10}$; wherein R$^{10}$, when present, is selected from hydrogen and halogen; wherein R$^1$ is selected from —(C1-C4 alkyl)OR$^{11}$, —(C1-C4 alkyl)NR$^{12a}$R$^{12b}$, —CO$_2$R$^{13}$, and —C(O)NR$^{14a}$R$^{14b}$; wherein each of R$^{11}$, R$^{12a}$, and R$^{12b}$, when present, is independently selected from hydrogen, C1-C4 alkyl, —C(=NH)NH$_2$, —CO$_2$(C1-C4 alkyl), —(C1-C4 alkyl)OR$^{20}$, —(C1-C4 alkyl)NR$^{21a}$R$^{21b}$, —(C1-C4 alkyl)Ar$^1$, and Ar$^1$; wherein Ar$^1$, when present, is selected from aryl and heteroaryl and substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of R$^{13}$, R$^{14a}$, and R$^{14b}$, when present, is independently selected from hydrogen and C1-C4 alkyl; wherein R$^2$, when present, is selected from C1-C4 alkyl and —(C1-C4 alkyl)NR$^{15a}$R$^{15b}$; wherein each of R$^{15a}$ and R$^{15b}$, when present, is independently selected from hydrogen and C1-C4 alkyl; wherein R$^3$ is selected from hydrogen and C1-C4 alkyl; or wherein each of R$^2$, when present, and R$^3$ together comprise a 5- to 6-membered heterocycle substituted with a group selected from C1-C4 alkyl and —(C1-C4 alkyl)NR$^{16a}$R$^{16b}$; wherein each of R$^{16a}$ and R$^{16b}$, when present, is independently selected from hydrogen and C1-C4 alkyl; wherein each of R$^4$ and R$^5$ is hydrogen or together comprise a 5- to 6-membered heterocycle; and wherein Ar$^2$ is a heteroaryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, provided that when each of R$^4$ and R$^5$ is hydrogen, then R is —(C1-C4 alkyl)OR$^{11}$ or —(C1-C4 alkyl)NR$^{12a}$R$^{12b}$, or a pharmaceutically acceptable salt thereof.

Also disclosed are methods for modulating translation of a RNA virus in at least one cell, the method comprising contacting the cell with an effective amount of a compound having a structure represented by a formula selected from:

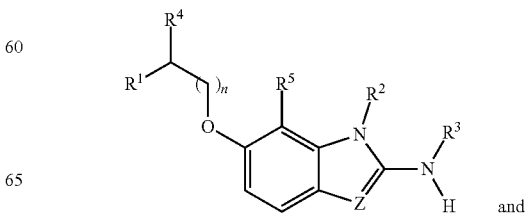
and

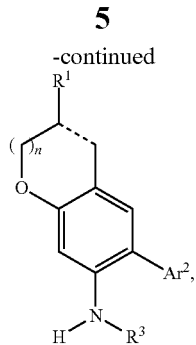

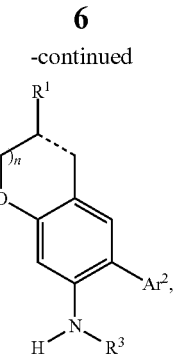

wherein ⌐⌐ is a single or a double covalent bond; wherein n is 0 or 1; wherein Z, when present, is selected from N and $CR^{10}$; wherein $R^{10}$, when present, is selected from hydrogen and halogen; wherein $R^1$ is selected from —(C1-C4 alkyl)$OR^{11}$, —(C1-C4 alkyl)$NR^{12a}R^{12b}$, —$CO_2R^{13}$, and —C(O)$NR^{14a}R^{14b}$; wherein each of $R^{11}$, $R^{12a}$, and $R^{12b}$, when present, is independently selected from hydrogen, C1-C4 alkyl, —C(=NH)$NH_2$, —$CO_2$(C1-C4 alkyl), —(C1-C4 alkyl)$OR^{20}$, —(C1-C4 alkyl)$NR^{21a}R^{21b}$, —(C1-C4 alkyl)$Ar^1$, and $Ar^1$; wherein $Ar^1$, when present, is selected from aryl and heteroaryl and substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of $R^{13}$, $R^{14a}$, and $R^{14b}$, when present, is independently selected from hydrogen and C1-C4 alkyl; wherein $R^2$, when present, is selected from C1-C4 alkyl and —(C1-C4 alkyl)$NR^{15a}R^{15b}$; wherein each of $R^{15a}$ and $R^{15b}$, when present, is independently selected from hydrogen and C1-C4 alkyl; wherein $R^3$ is selected from hydrogen and C1-C4 alkyl; or wherein each of $R^2$, when present, and $R^3$ together comprise a 5- to 6-membered heterocycle substituted with a group selected from C1-C4 alkyl and —(C1-C4 alkyl)$NR^{16a}R^{16b}$; wherein each of $R^{16a}$ and $R^{16b}$, when present, is independently selected from hydrogen and C1-C4 alkyl; wherein each of $R^4$ and $R^5$ is hydrogen or together comprise a 5- to 6-membered heterocycle; and wherein $Ar^2$ is a heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, provided that when each of $R^4$ and $R^5$ is hydrogen, then R is —(C1-C4 alkyl)$OR^{11}$ or —(C1-C4 alkyl)$NR^{12a}R^{12b}$, or a pharmaceutically acceptable salt thereof.

Also disclosed are methods for treating a RNA virus infection in a subject, the method comprising administering to the subject an effective amount of a compound having a structure represented by a formula selected from:

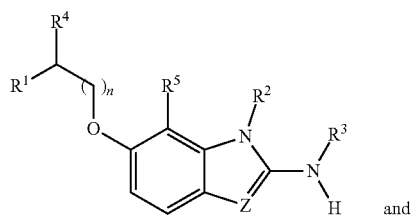

wherein ⌐⌐ is a single or a double covalent bond; wherein n is 0 or 1; wherein Z, when present, is selected from N and $CR^{10}$; wherein $R^{10}$, when present, is selected from hydrogen and halogen; wherein $R^1$ is selected from —(C1-C4 alkyl)$OR^{11}$, —(C1-C4 alkyl)$NR^{12a}R^{12b}$, —$CO_2R^{13}$, and —C(O)$NR^{14a}R^{14b}$; wherein each of $R^{11}$, $R^{12a}$, and $R^{12b}$, when present, is independently selected from hydrogen, C1-C4 alkyl, —C(=NH)$NH_2$, —$CO_2$(C1-C4 alkyl), —(C1-C4 alkyl)$OR^{20}$, —(C1-C4 alkyl)$NR^{21a}R^{21b}$, —(C1-C4 alkyl)$Ar^1$, and $Ar^1$; wherein $Ar^1$, when present, is selected from aryl and heteroaryl and substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of $R^{13}$, $R^{14a}$, and $R^{14b}$, when present, is independently selected from hydrogen and C1-C4 alkyl; wherein $R^2$, when present, is selected from C1-C4 alkyl and —(C1-C4 alkyl)$NR^{15a}R^{15b}$; wherein each of $R^{15a}$ and $R^{15b}$, when present, is independently selected from hydrogen and C1-C4 alkyl; wherein $R^3$ is selected from hydrogen and C1-C4 alkyl; or wherein each of $R^2$, when present, and $R^3$ together comprise a 5- to 6-membered heterocycle substituted with a group selected from C1-C4 alkyl and —(C1-C4 alkyl)$NR^{16a}R^{16b}$; wherein each of $R^{16a}$ and $R^{16b}$, when present, is independently selected from hydrogen and C1-C4 alkyl; wherein each of $R^4$ and $R^5$ is hydrogen or together comprise a 5- to 6-membered heterocycle; and wherein $Ar^2$ is a heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, provided that when each of $R^4$ and $R^5$ is hydrogen, then R is —(C1-C4 alkyl)$OR^{11}$ or —(C1-C4 alkyl)$NR^{12a}R^{12b}$, or a pharmaceutically acceptable salt thereof.

Also disclosed are kits comprising a compound having a structure represented by a formula selected from:

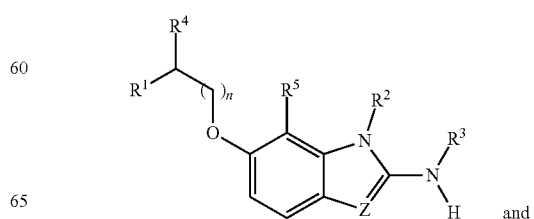

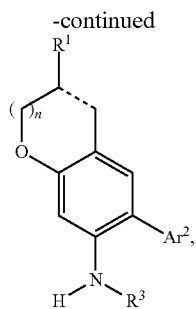

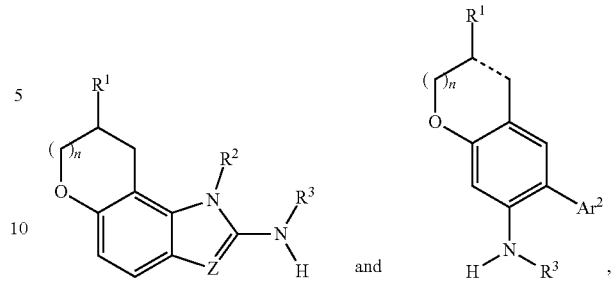

wherein ⁓ is a single or a double covalent bond; wherein n is 0 or 1; wherein Z, when present, is selected from N and $CR^{10}$; wherein $R^{10}$, when present, is selected from hydrogen and halogen; wherein $R^1$ is selected from —(C1-C4 alkyl)$OR^{11}$, —(C1-C4 alkyl)$NR^{12a}R^{12b}$, —$CO_2R^{13}$, and —C(O)$NR^{14a}R^{14b}$; wherein each of $R^{11}$, $R^{12a}$, and $R^{12b}$, when present, is independently selected from hydrogen, C1-C4 alkyl, —C(=NH)$NH_2$, —$CO_2$(C1-C4 alkyl), —(C1-C4 alkyl)$OR^{20}$, —(C1-C4 alkyl)$NR^{21a}R^{21b}$, —(C1-C4 alkyl)$Ar^1$, and $Ar^1$; wherein $Ar^1$, when present, is selected from aryl and heteroaryl and substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of $R^{13}$, $R^{14a}$, and $R^{14b}$, when present, is independently selected from hydrogen and C1-C4 alkyl; wherein $R^2$, when present, is selected from C1-C4 alkyl and —(C1-C4 alkyl)$NR^{15a}R^{15b}$; wherein each of $R^{11a}$ and $R^{15b}$, when present, is independently selected from hydrogen and C1-C4 alkyl; wherein $R^3$ is selected from hydrogen and C1-C4 alkyl; or wherein each of $R^2$, when present, and $R^3$ together comprise a 5- to 6-membered heterocycle substituted with a group selected from C1-C4 alkyl and —(C1-C4 alkyl)$NR^{16a}R^{16b}$; wherein each of $R^{16a}$ and $R^{16b}$, when present, is independently selected from hydrogen and C1-C4 alkyl; wherein each of $R^4$ and $R^5$ is hydrogen or together comprise a 5- to 6-membered heterocycle; and wherein $Ar^2$ is a heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, provided that when each of $R^4$ and $R^5$ is hydrogen, then R is —(C1-C4 alkyl)$OR^{11}$ or —(C1-C4 alkyl)$NR^{12a}R^{12b}$, or a pharmaceutically acceptable salt thereof, and one or more of: (a) at least one agent known for the treatment of a RNA virus infection; (b) instructions for administering the compound in connection with a RNA virus infection; (c) instructions for administering the compound in connection with reducing the risk of a RNA virus infection; and (d) instructions for treating a RNA virus infection.

Also disclosed are methods for treating a disorder of uncontrolled cellular proliferation in a subject, the method comprising administering to the subject an effective amount of a compound having a structure represented by a formula selected from:

wherein ⁓ is a single or a double covalent bond; wherein n is 0 or 1; wherein Z, when present, is selected from N and $CR^{10}$; wherein $R^{10}$, when present, is selected from hydrogen and halogen; wherein $R^1$ is selected from —(C1-C4 alkyl)$OR^{11}$, —(C1-C4 alkyl)$NR^{12a}R^{12b}$, —$CO_2R^{13}$, and —C(O)$NR^{14a}R^{14b}$; wherein each of $R^{11}$, $R^{12a}$, and $R^{12b}$, when present, is independently selected from hydrogen, C1-C4 alkyl, —C(=NH)$NH_2$, —$CO_2$(C1-C4 alkyl), —(C1-C4 alkyl)$OR^{20}$, —(C1-C4 alkyl)$NR^{21a}R^{21b}$, —(C1-C4 alkyl)$Ar^1$, and $Ar^1$; wherein $Ar^1$, when present, is selected from aryl and heteroaryl and substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of $R^{13}$, $R^{14a}$, and $R^{14b}$, when present, is independently selected from hydrogen and C1-C4 alkyl; wherein $R^2$, when present, is selected from C1-C4 alkyl and —(C1-C4 alkyl)$NR^{15a}R^{15b}$; wherein each of $R^{15a}$ and $R^{15b}$, when present, is independently selected from hydrogen and C1-C4 alkyl; wherein $R^3$ is selected from hydrogen and C1-C4 alkyl; or wherein each of $R^2$, when present, and $R^3$ together comprise a 5- to 6-membered heterocycle substituted with a group selected from C1-C4 alkyl and —(C1-C4 alkyl)$NR^{16a}R^{16b}$; wherein each of $R^{16a}$ and $R^{16b}$, when present, is independently selected from hydrogen and C1-C4 alkyl; and wherein $Ar^2$ is a heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, or a pharmaceutically acceptable salt thereof.

Also disclosed are kits comprising a compound having a structure represented by a formula selected from:

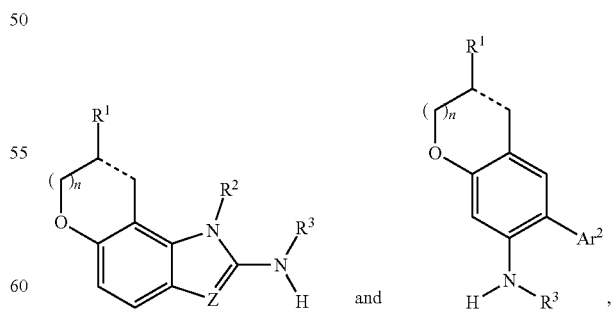

wherein ⁓ is a single or a double covalent bond; wherein n is 0 or 1; wherein Z, when present, is selected from N and $CR^{10}$; wherein $R^{10}$, when present, is selected from hydrogen and halogen; wherein $R^1$ is selected from —(C1-C4 alkyl)$OR^{11}$, —(C1-C4 alkyl)$NR^{12a}R^{12b}$, —$CO_2R^{13}$, and —C(O)

$NR^{14a}R^{14b}$; wherein each of $R^{11}$, $R^{12a}$, and $R^{12b}$, when present, is independently selected from hydrogen, C1-C4 alkyl, —C(=NH)NH$_2$, —CO$_2$(C1-C4 alkyl), —(C1-C4 alkyl)OR$^{20}$, —(C1-C4 alkyl)NR$^{21a}$R$^{21b}$, —(C1-C4 alkyl)Ar$^1$, and Ar$^1$; wherein Ar$^1$, when present, is selected from aryl and heteroaryl and substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of $R^{13}$, $R^{14a}$, and $R^{14b}$, when present, is independently selected from hydrogen and C1-C4 alkyl; wherein $R^2$, when present, is selected from C1-C4 alkyl and —(C1-C4 alkyl)NR$^{15a}$R$^{15b}$; wherein each of $R^{15a}$ and $R^{15b}$, when present, is independently selected from hydrogen and C1-C4 alkyl; wherein $R^3$ is selected from hydrogen and C1-C4 alkyl; or wherein each of $R^2$, when present, and $R^3$ together comprise a 5- to 6-membered heterocycle substituted with a group selected from C1-C4 alkyl and —(C1-C4 alkyl)NR$^{16a}$R$^{16b}$; wherein each of $R^{16a}$ and $R^{16b}$, when present, is independently selected from hydrogen and C1-C4 alkyl; and wherein Ar$^2$ is a heteroaryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, or a pharmaceutically acceptable salt thereof, and one or more of: (a) at least one agent associated with the treatment of a disorder of uncontrolled cellular proliferation; (b) instructions for administering the compound in connection with treating a disorder of uncontrolled cellular proliferation; and (c) instructions for treating a disorder of uncontrolled cellular proliferation.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

FIG. 1 shows representative antiviral activity of translation inhibitors.

Figure 2:
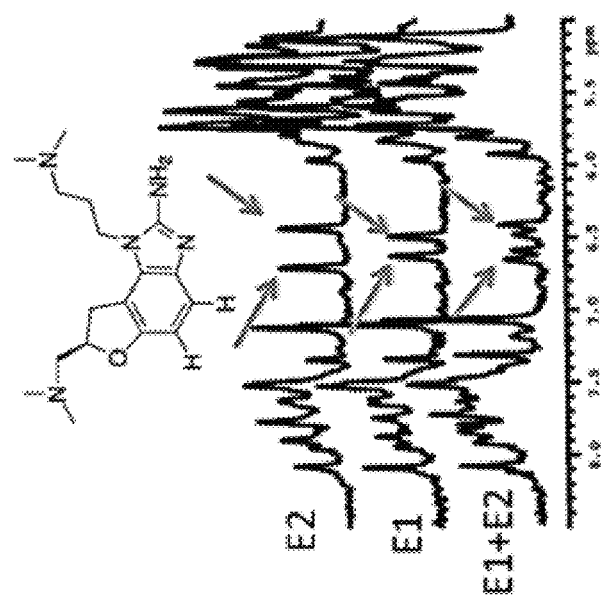
FIG. 2 shows a representative structural model of human iMet-tRNA anticodon domain in complex with compound E2 (left). The two proton NMR signals indicated with the arrows are from the aromatic protons on E2 as shown (right). These protons are shown shifted from their positions in the free drug. The NMR spectrum for the "same" two protons for bound E1 are also shown. For the free drug, the H1 and H2 protons for E1 and E2 have identical shifts since E1 and E2 are enantiomers. (E2+E1) is both drugs simultaneously bound to iMet. This shows that the bound conformations are distinct and that this distinction affects the H1/H2 proton shifts. The $K_D$ values for E1 and E2 are similar (~1 μM).
Figure 2:
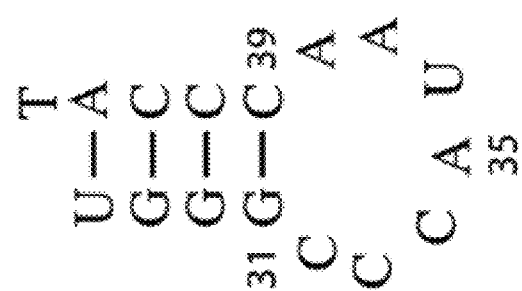
Figure 2:
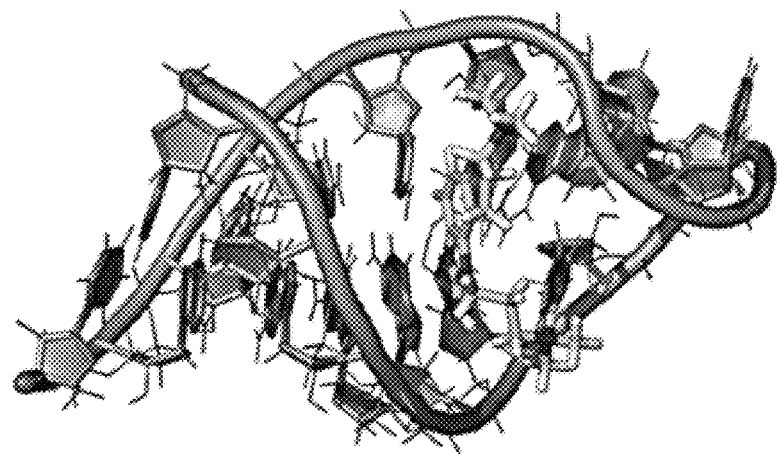

Additional advantages of the invention will be set forth in part in the description that follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half-maximal (50%) inhibitory concentration (IC) of a substance.

As used herein, "$EC_{50}$," is intended to refer to the concentration of a substance (e.g., a compound or a drug)

that is required for 50% agonism of a biological process, or component of a process, including a protein, subunit, organelle, ribonucleoprotein, etc. For example, an $EC_{50}$ can refer to the concentration of a compound that reduces viral replication by 50%. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response.

As used herein, "$EC_{90}$" is intended to refer to the concentration of a substance (e.g., a compound or a drug) that is required for 90% agonism of a biological process, or component of a process, including a protein, subunit, organelle, ribonucleoprotein, etc. For example, an $EC_{90}$ can refer to the concentration of a compound that reduces viral replication by 90%. In one aspect, an $EC_{90}$ can refer to the concentration of a substance that is required for 90% agonism in vivo, as further defined elsewhere herein. In a further aspect, $EC_{90}$ refers to the concentration of agonist that provokes a response halfway between the baseline and maximum response.

As used herein, "$CC_{50}$" is intended to refer to the concentration of a substance (e.g., a compound or a drug) that is required to reduce the viability of a biological process, or component of a process, including a cell, protein, subunit, organelle, ribonucleoprotein, etc. by 50%. For example, a $CC_{50}$ can refer to the concentration of a compound that reduces cell viability by 50%.

As used herein, "$SI_{50}$," is intended to refer to the $CC_{50}$ of a substance (e.g., a compound or a drug) divided by the $EC_{50}$ of the same substance (e.g., the same compound or drug).

As used herein, "$SI_{90}$," is intended to refer to the $CC_{90}$ of a substance (e.g., a compound or a drug) divided by the $EC_{90}$ of the same substance (e.g., the same compound or drug).

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; anti-ALS agents such as entry inhibitors, fusion inhibitors, non-nucleoside reverse transcriptase inhibitors (NNRTIs), nucleoside reverse transcriptase inhibitors (NRTIs), nucleotide reverse transcriptase inhibitors, NCP7 inhibitors, protease inhibitors, and integrase inhibitors; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —NH$_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(AO(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3- dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —N(R°)C(S)R°; —$(CH_2)_{0-4}N(R°)C(O)NR°_2$; —N(R°)C(S)NR°_2; —$(CH_2)_{0-4}N(R°)C(O)OR°$; —N(R°)N(R°)C(O)R°; —N(R°)N(R°)C(O)NR°_2; —N(R°)N(R°)C(O)OR°; —$(CH_2)_{0-4}C(O)R°$; —C(S)R°; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —OC(O)$(CH_2)_{0-4}SR$—, SC(S)SR°; —$(CH_2)_{0-4}SC(O)R°$; —$(CH_2)_{0-4}C(O)NR°_2$; —C(S)NR°_2; —C(S)SR°; —$(CH_2)_{0-4}OC(O)NR°_2$; —C(O)N(OR°)R°; —C(O)C(O)R°; —C(O)CH_2C(O)R°; —C(NOR°)R°; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —N(R°)S(O)_2NR°_2; —N(R°)S(O)_2R°; —N(OR°)R°; —C(NH)NR°_2; —P(O)_2R°; —P(O)R°_2; —OP(O)R°_2; —OP(O)(OR°)_2; SiR°_3; —$(C_{1-4}$ straight or branched alkylene)O—N(R°)_2; or —$(C_{1-4}$ straight or branched alkylene)C(O)O—N(R°)_2, wherein each R° may be substituted as defined below and is independently hydrogen, C1-6 aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^●$, -(haloR$^●$), —$(CH_2)_{0-2}OH$, —$(CH_2)_{0-2}OR^●$, —$(CH_2)_{0-2}CH(OR^●)_2$; —O(haloR$^●$), —CN, —$N_3$, —$(CH_2)_{0-2}C(O)R^●$, —$(CH_2)_{0-2}C(O)OH$, —(CH$_2$)$_{0-2}$C(O)OR●, —(CH$_2$)$_{0-2}$SR●, —(CH$_2$)$_{0-2}$SH, —(CH$_2$)$_{0-2}$NH$_2$, —(CH$_2$)$_{0-2}$NHR●, —(CH$_2$)$_{0-2}$NR●$_2$, —NO$_2$, —SiR●$_3$, —OSiR●$_3$, —C(O)SR●, —(C$_{1-4}$ straight or branched alkylene)C(O)OR●, or —SSR● wherein each R● is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

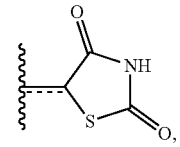

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radioactively labeled forms, isomers, solvates and combinations thereof. The "combinations" mentioned in this context are refer to derivatives falling within at least two of the groups: pharmaceutically acceptable salts, prodrugs, deuterated forms, radioactively labeled forms, isomers, and solvates. Examples of radioactively labeled forms include compounds labeled with tritium, phosphorous-32, iodine-129, carbon-11, fluorine-18, and the like.

Compounds described herein comprise atoms in both their natural isotopic abundance and in non-natural abundance. The disclosed compounds can be isotopically labeled or isotopically substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules that owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

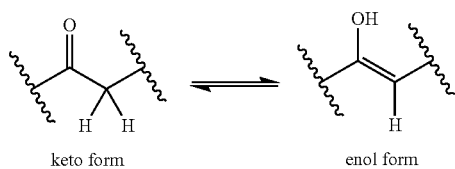

keto form          enol form

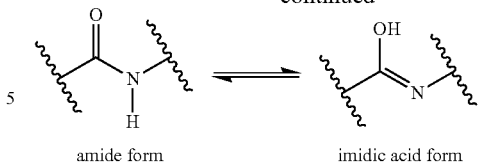

amide form          imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and N-unsubstituted, 5-$A^3$ as shown below.

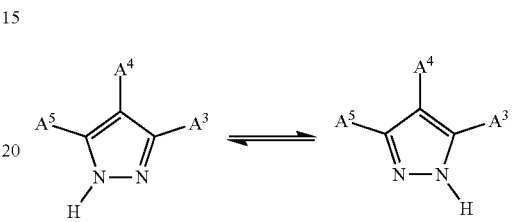

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

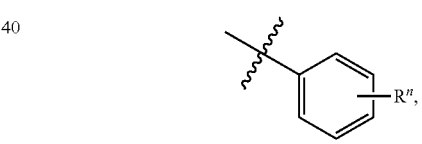

which is understood to be equivalent to a formula:

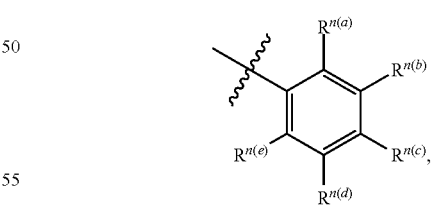

wherein n is typically an integer. That is, R is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Strem Chemicals (Newburyport, MA), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful in, for example, the prevention and treatment of hepatitis (e.g., hepatitis C), RNA virus infections (e.g., Zika virus, dengue virus, Powassan virus, Chikungunya virus, Enterovirus, respiratory syntactical virus (RSV), Rift Valley fever, Influenza virus, Tacaribe virus, Mayaro virus, West Nile virus, yellow fever virus, and coronavirus), and disorders of uncontrolled cellular proliferation (e.g., cancer).

In one aspect, the disclosed compounds exhibit modulation of hepatitis viral translation. In a further aspect, the disclosed compounds exhibit inhibition of hepatitis viral translation.

In one aspect, the disclosed compounds exhibit modulation of translation of a RNA viral infection. In a further aspect, the disclosed compounds exhibit inhibition of translation of a RNA viral infection.

In one aspect, the disclosed compounds exhibit modulation of c-Myc signaling. In a further aspect, the disclosed compounds exhibit inhibition of c-Myc signaling.

In one aspect, the compounds of the invention are useful in modulating hepatitis viral translation in a mammal. In a further aspect, the compounds of the invention are useful in modulating hepatitis viral translation in at least one cell.

In one aspect, the compounds of the invention are useful in modulating translation of a RNA viral infection in a mammal. In a further aspect, the compounds of the invention are useful in modulating translation of a RNA viral infection in at least one cell.

In one aspect, the compounds of the invention are useful in modulating c-Myc signaling in a mammal. In a further aspect, the compounds of the invention are useful in modulating c-Myc signaling in at least one cell.

In one aspect, the compounds of the invention are useful in the treatment of hepatitis, as further described herein.

In one aspect, the compounds of the invention are useful in the treatment of a RNA virus, as further described herein.

In one aspect, the compounds of the invention are useful in the treatment of a disorder of uncontrolled cellular proliferation, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula selected from:

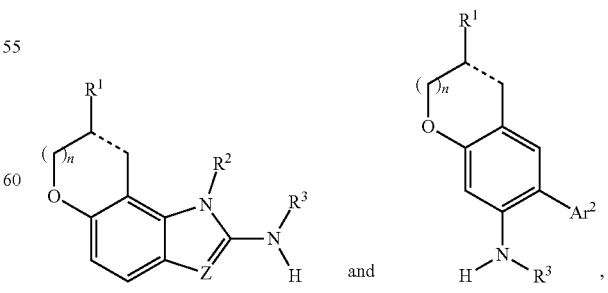

wherein ⌢ is a single or a double covalent bond; wherein n is 0 or 1; wherein Z, when present, is selected from N and CR$^{10}$; wherein R$^{10}$, when present, is selected from hydrogen and halogen; wherein R$^1$ is selected from —(C1-C4 alkyl)OR$^{11}$, —(C1-C4 alkyl)NR$^{12a}$R$^{12b}$, —CO$_2$R$^{13}$, and —C(O)NR$^{14a}$R$^{14b}$; wherein each of R$^{11}$, R$^{12a}$, and R$^{12b}$, when present, is independently selected from hydrogen, C1-C4 alkyl, —C(=NH)NH$_2$, —CO$_2$(C1-C4 alkyl), —(C1-C4 alkyl)OR$^{20}$, —(C1-C4 alkyl)NR$^{21a}$R$^{21b}$, —(C1-C4 alkyl)Ar$^1$, and Ar$^1$; wherein Ar$^1$, when present, is selected from aryl and heteroaryl and substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of R$^{13}$, R$^{14a}$, and R$^{14b}$, when present, is independently selected from hydrogen and C1-C4 alkyl; wherein R$^2$, when present, is selected from C1-C4 alkyl and —(C1-C4 alkyl)NR$^{15a}$R$^{15b}$; wherein each of R$^{15a}$ and R$^{15b}$, when present, is independently selected from hydrogen and C1-C4 alkyl; wherein R$^3$ is selected from hydrogen and C1-C4 alkyl; or wherein each of R$^2$, when present, and R$^3$ together comprise a 5- to 6-membered heterocycle substituted with a group selected from C1-C4 alkyl and —(C1-C4 alkyl)NR$^{16a}$R$^{16b}$; wherein each of R$^{16a}$ and R$^{16b}$, when present, is independently selected from hydrogen and C1-C4 alkyl; and wherein Ar$^2$ is a heteroaryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, provided that when the compound has a structure represented by a formula:

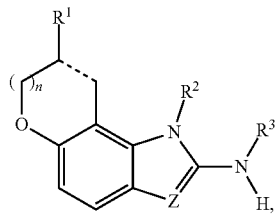

then either ⋰ is a double bond, Z is CR$^{10}$, or R$^2$ is C1-C4 alkyl, or a pharmaceutically acceptable salt thereof.

In one aspect, disclosed are compounds selected from:

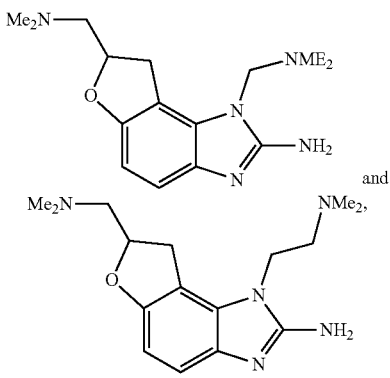

or a pharmaceutically acceptable salt thereof.

In one aspect, disclosed are compounds having a structure represented by a formula selected from:

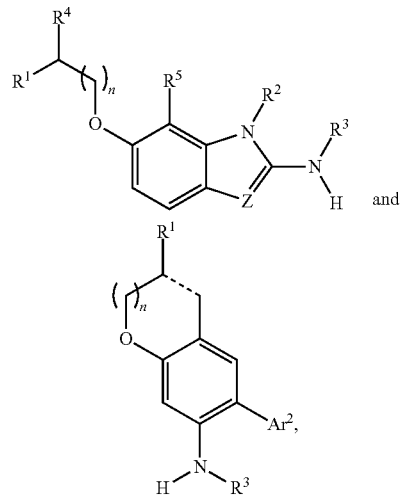

wherein ⋰ is a single or a double covalent bond; wherein n is 0 or 1; wherein Z, when present, is selected from N and CR$^{10}$; wherein R$^{10}$, when present, is selected from hydrogen and halogen; wherein R$^1$ is selected from —(C1-C4 alkyl)OR$^{11}$, —(C1-C4 alkyl)NR$^{12a}$R$^{12b}$, —CO$_2$R$^{13}$, and —C(O)NR$^{14a}$R$^{14b}$; wherein each of R$^{11}$, R$^{12a}$, and R$^{12b}$, when present, is independently selected from hydrogen, C1-C4 alkyl, —C(=NH)NH$_2$, —CO$_2$(C1-C4 alkyl), —(C1-C4 alkyl)OR$^{20}$, —(C1-C4 alkyl)NR$^{21a}$R$^{21b}$, —(C1-C4 alkyl)Ar$^1$, and Ar$^1$; wherein Ar$^1$, when present, is selected from aryl and heteroaryl and substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of R$^{13}$, R$^{14a}$, and R$^{14b}$, when present, is independently selected from hydrogen and C1-C4 alkyl; wherein R$^2$, when present, is selected from C1-C4 alkyl and —(C1-C4 alkyl)NR$^{15a}$R$^{15b}$; wherein each of R$^{11a}$ and R$^{15b}$, when present, is independently selected from hydrogen and C1-C4 alkyl; wherein R$^3$ is selected from hydrogen and C1-C4 alkyl; or wherein each of R$^2$, when present, and R$^3$ together comprise a 5- to 6-membered heterocycle substituted with a group selected from C1-C4 alkyl and —(C1-C4 alkyl)NR$^{16a}$R$^{16b}$; wherein each of R$^{16a}$ and R$^{16b}$, when present, is independently selected from hydrogen and C1-C4 alkyl; wherein each of R$^4$ and R$^5$ is hydrogen or together comprise a 5- to 6-membered heterocycle; and wherein Ar$^2$ is a heteroaryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, provided that when each of R$^4$ and R$^5$ is hydrogen, then R is —(C1-C4 alkyl)OR$^{11}$ or —(C1-C4 alkyl)NR$^{12a}$R$^{12b}$, or a pharmaceutically acceptable salt thereof.

In one aspect, disclosed are compounds having a structure represented by a formula selected from:

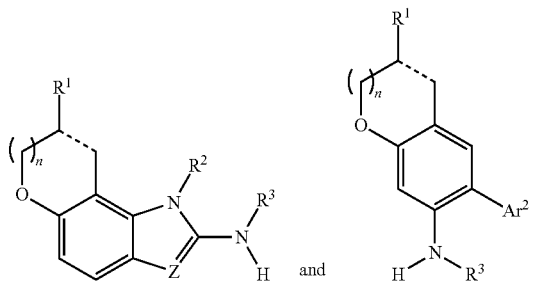

and wherein ⁓ is a single or a double covalent bond; wherein n is 0 or 1; wherein Z, when present, is selected from N and $CR^{10}$; wherein $R^{10}$, when present, is selected from hydrogen and halogen; wherein $R^1$ is selected from —(C1-C4 alkyl) $OR^{11}$, —(C1-C4 alkyl)$NR^{12a}R^{12b}$, —$CO_2R^{13}$, and —C(O)$NR^{14a}R^{14b}$; wherein each of $R^{11}$, $R^{12a}$, and $R^{12b}$, when present, is independently selected from hydrogen, C1-C4 alkyl, —C(=NH)$NH_2$, —$CO_2$(C1-C4 alkyl), —(C1-C4 alkyl)$OR^{20}$, —(C1-C4 alkyl)$NR^{21a}R^{21b}$, —(C1-C4 alkyl) $Ar^1$, and $Ar^1$; wherein $Ar^1$, when present, is selected from aryl and heteroaryl and substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of $R^{13}$, $R^{14a}$, and $R^{14b}$, when present, is independently selected from hydrogen and C1-C4 alkyl; wherein $R^2$, when present, is selected from C1-C4 alkyl and —(C1-C4 alkyl)$NR^{15a}R^{15b}$; wherein each of $R^{15a}$ and $R^{15b}$, when present, is independently selected from hydrogen and C1-C4 alkyl; wherein $R^3$ is selected from hydrogen and C1-C4 alkyl; or wherein each of $R^2$, when present, and $R^3$ together comprise a 5- to 6-membered heterocycle substituted with a group selected from C1-C4 alkyl and —(C1-C4 alkyl)$NR^{16a}R^{16b}$; wherein each of $R^{16a}$ and $R^{16b}$, when present, is independently selected from hydrogen and C1-C4 alkyl; and wherein $Ar^2$ is a heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, or a pharmaceutically acceptable salt thereof.

In a further aspect, each of $R^4$ and $R^5$ is hydrogen. In a still further aspect, each of $R^4$ and $R^5$ together comprise a 5- to 6-membered heterocycle.

In a further aspect, the compound has a structure represented by a formula:

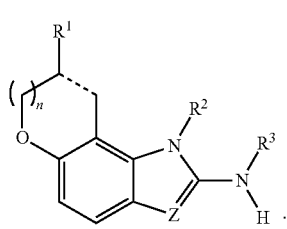

In a further aspect, the compound has a structure represented by a formula:

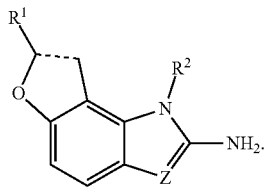

In a further aspect, the compound has a structure represented by a formula:

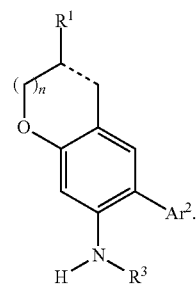

In a further aspect, the compound has a structure represented by a formula:

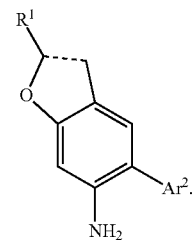

In a further aspect, the compound has a structure represented by a formula:

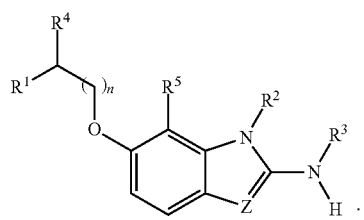

In a further aspect, the compound is selected from:

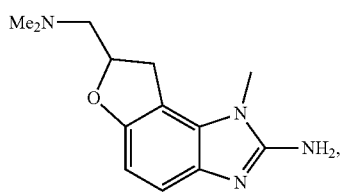

37
-continued
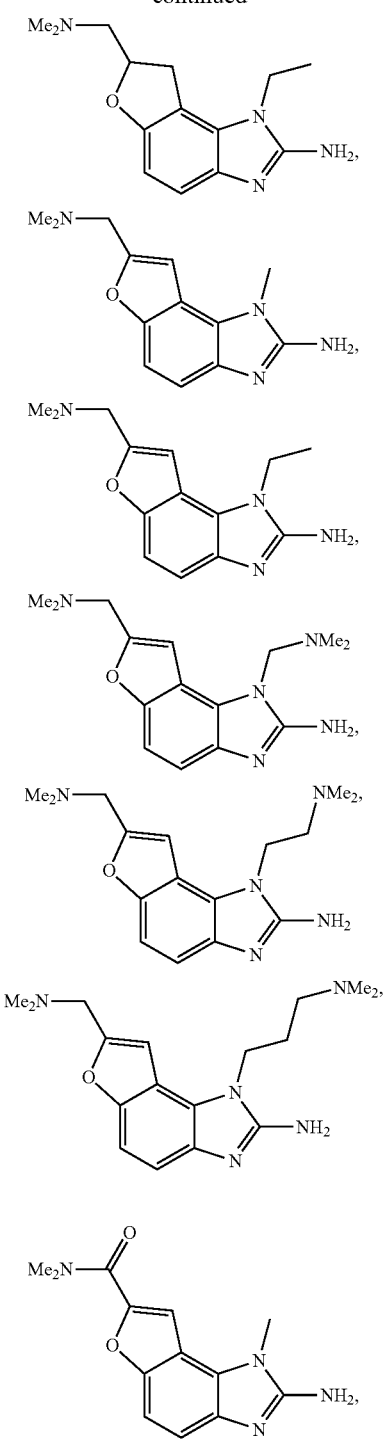
38
-continued
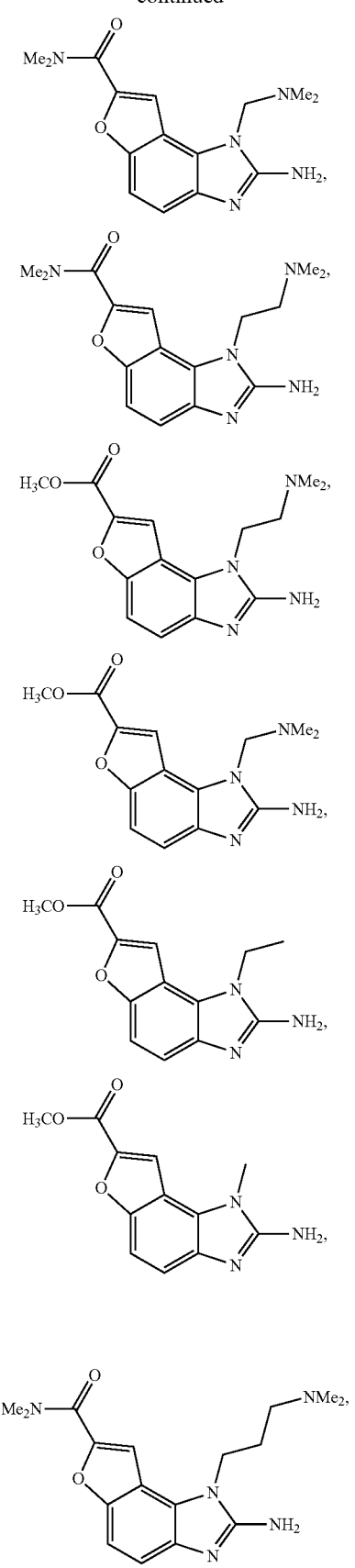

-continued
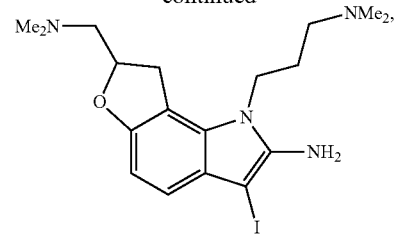
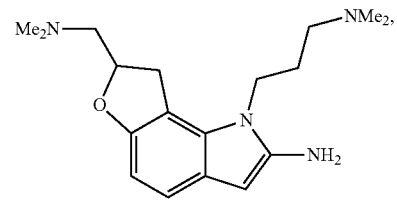
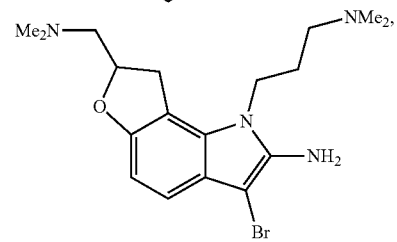
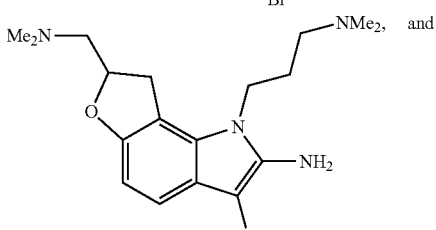
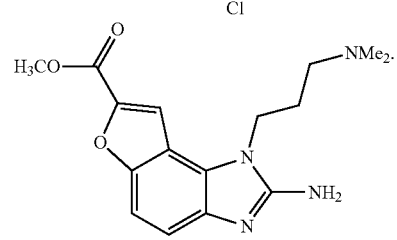
In a further aspect, the compound is selected from:
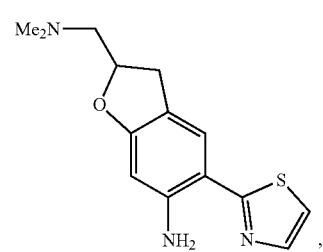
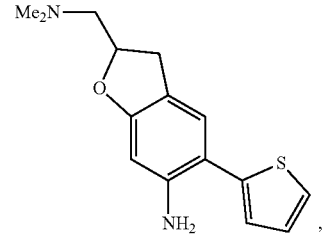
-continued
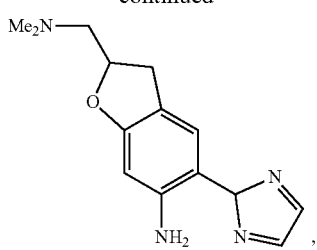
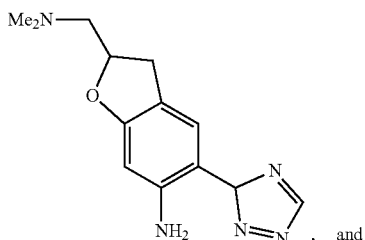
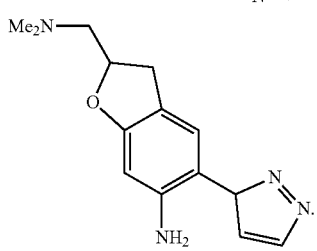
In a further aspect, the compound is selected from:
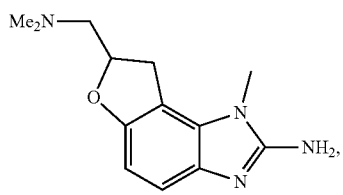
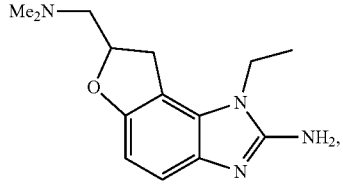
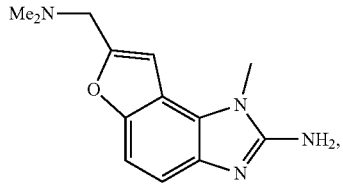
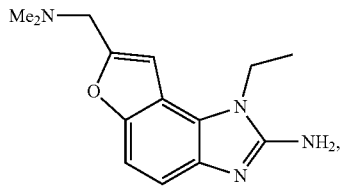

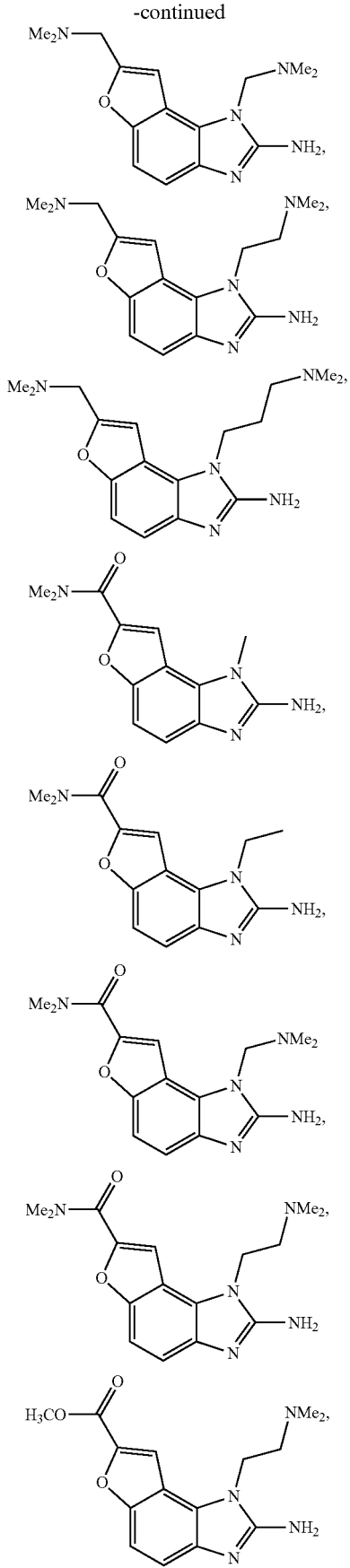
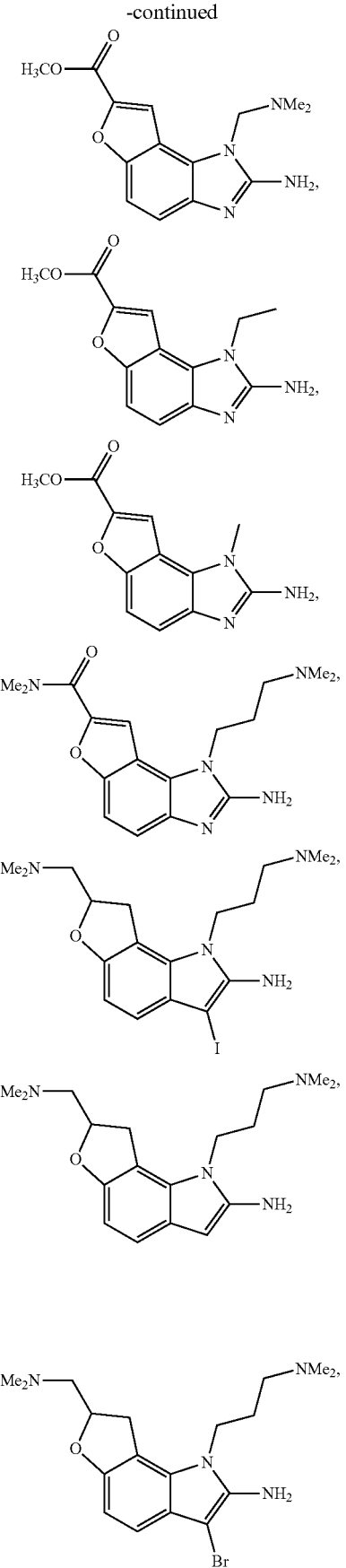

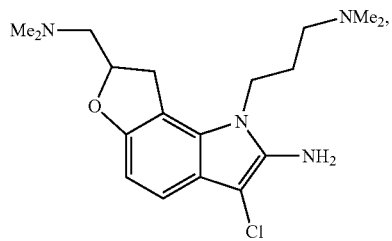
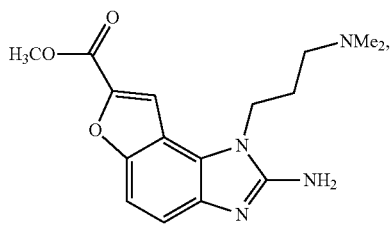
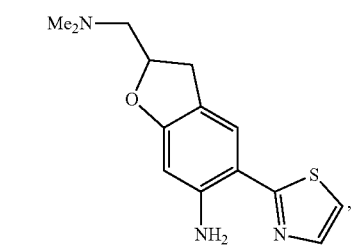
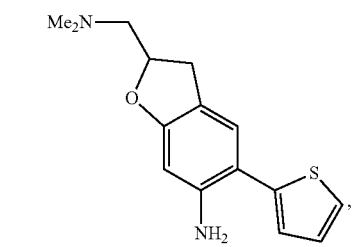
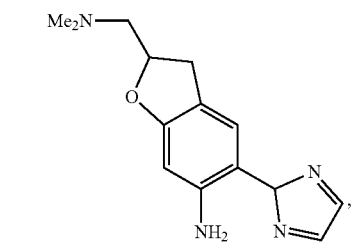
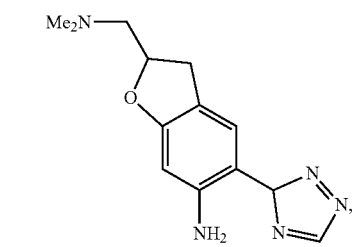
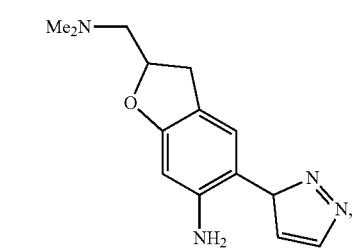
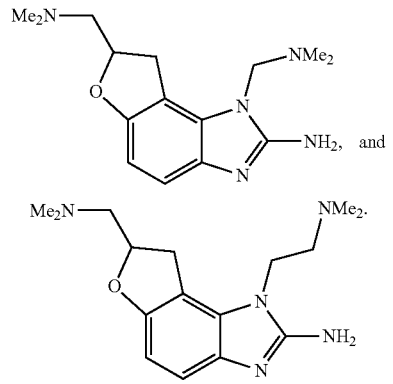
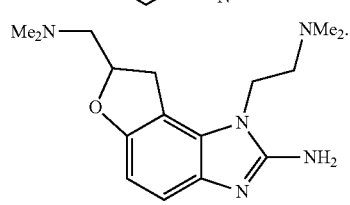
In a further aspect, the compound is selected from:
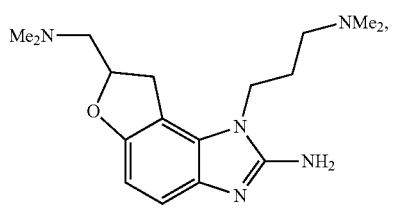
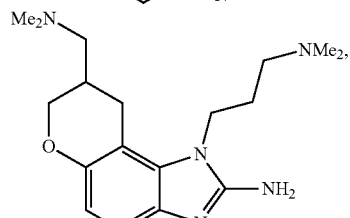
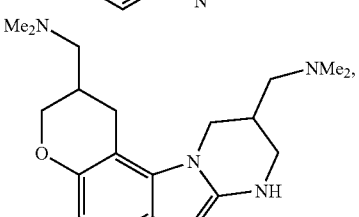
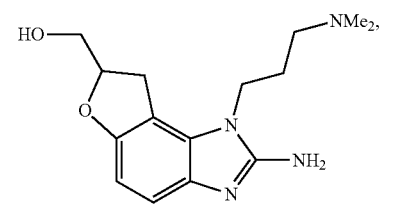
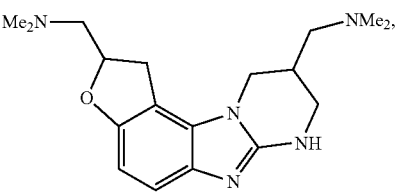

-continued

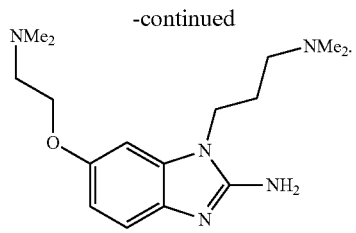

In one aspect, ⌐ is a single or a double covalent bond. In a further aspect, ⌐ is a single covalent bond. In a still further aspect, ⌐ is a double covalent bond.

In one aspect, n is 0 or 1. In a further aspect, n is 0. In a still further aspect, n is 1.

a. Z Groups

In one aspect, Z, when present, is selected from N and $CR^{10}$. In a further aspect, Z, when present, is N. In a still further aspect, Z, when present, is $CR^{10}$.

In a further aspect, Z, when present, is selected from N and CH. In a further aspect, Z, when present, is CH.

b. $R^1$ Groups

In one aspect, $R^1$ is selected from —(C1-C4 alkyl)$OR^{11}$, —(C1-C4 alkyl)$NR^{12a}R^{12b}$, —$CO_2R^{13}$, and —$C(O)NR^{14a}R^{14b}$. In a further aspect, $R^1$ is selected from —$CH_2OR^{11}$, —$CH_2CH_2OR^{11}$, —$CH_2CH_2CH_2OR^{11}$, —CH($CH_3$)$CH_2OR^{11}$, —$CH_2NR^{12a}R^{12b}$, —$CH_2CH_2NR^{12a}R^{12b}$, —$CH_2CH_2CH_2NR^{12a}R^{12b}$, —CH($CH_3$)$CH_2NR^{12a}R^{12b}$, —$CO_2R^{13}$, and —$C(O)NR^{14a}R^{14b}$. In a still further aspect, $R^1$ is selected from —$CH_2OR^{11}$, —$CH_2CH_2OR^{11}$, —$CH_2NR^{12a}R^{12b}$, —$CH_2CH_2NR^{12a}R^{12b}$, —$CO_2R^{13}$, and —$C(O)NR^{14a}R^{14b}$. In yet a further aspect, $R^1$ is selected from —$CH_2OR^{11}$, —$CH_2NR^{12a}R^{12b}$, —$CO_2R^{13}$, and —$C(O)NR^{14a}R^{14b}$.

In various aspects, $R^1$ is selected from —(C1-C4 alkyl)$OR^1$ and —(C1-C4 alkyl)$NR^{12a}R^{12b}$. In a further aspect, $R^1$ is selected from —$CH_2OR^{11}$, —$CH_2CH_2OR^{11}$, —$CH_2CH_2CH_2OR^{11}$, —CH($CH_3$)$CH_2OR^{11}$, —$CH_2NR^{12a}R^{12b}$, —$CH_2CH_2NR^{12a}R^{12b}$, $CH_2CH_2CH_2NR^{12a}R^{12b}$, and —CH($CH_3$)$CH_2NR^{12a}R^{12b}$. In a still further aspect, $R^1$ is selected from —$CH_2OR^{11}$, —$CH_2CH_2OR^{11}$, —$CH_2NR^{12a}R^{12b}$, and —$CH_2CH_2NR^{12a}R^{12b}$. In yet a further aspect, $R^1$ is selected from —$CH_2OR^{11}$ and —$CH_2NR^{12a}R^{12b}$.

In various aspects, $R^1$ is —(C1-C4 alkyl)$OR^{11}$. In a further aspect, $R^1$ is selected from —$CH_2OR^{11}$, —$CH_2CH_2OR^{11}$, —$CH_2CH_2CH_2OR^{11}$, and —CH($CH_3$)$CH_2OR^{11}$. In a still further aspect, $R^1$ is selected from —$CH_2OR^{11}$ and —$CH_2CH_2OR^{11}$. In yet a further aspect, $R^1$ is —$CH_2OR^{11}$.

In various aspects, $R^1$ is —(C1-C4 alkyl)$NR^{12a}R^{12b}$. In a further aspect, $R^1$ is selected from —$CH_2NR^{12a}R^{12b}$, —$CH_2CH_2NR^{12a}R^{12b}$, —$CH_2CH_2CH_2NR^{12a}R^{12b}$, and —CH($CH_3$)$CH_2NR^{12a}R^{12b}$. In a still further aspect, $R^1$ is selected from —$CH_2NR^{12a}R^{12b}$ and —$CH_2CH_2NR^{12a}R^{12b}$. In yet a further aspect, $R^1$ is —$CH_2NR^{12a}R^{12b}$.

In various aspects, $R^1$ is selected from —$CO_2R^{13}$ and —$C(O)NR^{14a}R^{14b}$. In a further aspect, $R^1$ is —$CO_2R^{13}$. In a still further aspect, $R^1$ is —$C(O)NR^{14a}R^{14b}$.

c. $R^2$ Groups and $R^3$ Groups

In one aspect, $R^2$, when present, is selected from C1-C4 alkyl and —(C1-C4 alkyl)$NR^{15a}R^{15b}$ and $R^3$ is selected from hydrogen and C1-C4 alkyl or each of $R^2$, when present, and $R^3$ together comprise a 5- to 6-membered heterocycle substituted with a group selected from C1-C4 alkyl and —(C1-C4 alkyl)$NR^{16a}R^{16b}$.

In one aspect, $R^2$, when present, is selected from C1-C4 alkyl and —(C1-C4 alkyl)$NR^{15a}R^{15b}$ and $R^3$ is selected from hydrogen and C1-C4 alkyl.

In one aspect, $R^2$, when present, is selected from C1-C4 alkyl and —(C1-C4 alkyl)$NR^{15a}R^{15b}$. In a further aspect, $R^2$, when present, is selected from methyl, ethyl, n-propyl, isopropyl, —$CH_2NR^{15a}R^{15b}$, —$CH_2CH_2NR^{15a}R^{15b}$, —$CH_2CH_2CH_2NR^{15a}R^{15b}$, and —CH($CH_3$)$CH_2NR^{15a}R^{15b}$. In a still further aspect, $R^2$, when present, is selected from methyl, ethyl, —$CH_2NR^{15a}R^{15b}$ and —$CH_2CH_2NR^{15a}R^{15b}$. In yet a further aspect, $R^2$, when present, is selected from methyl and —$CH_2NR^{15a}R^{15b}$.

In one aspect, $R^3$ is selected from hydrogen and C1-C4 alkyl. In a further aspect, $R^3$ is selected from hydrogen, methyl, ethyl, n-propyl, and isopropyl. In a still further aspect, $R^3$ is selected from hydrogen, methyl, and ethyl. In yet a further aspect, $R^3$ is selected from hydrogen and ethyl. In an even further aspect, $R^3$ is selected from hydrogen and methyl.

In various aspects, $R^2$, when present, is C1-C4 alkyl. In a further aspect, $R^2$, when present, is selected from methyl, ethyl, n-propyl, and isopropyl. In a still further aspect, $R^2$, when present, is selected from methyl and ethyl. In yet a further aspect, $R^2$, when present, is methyl.

In various aspects, $R^2$, when present, is —(C1-C4 alkyl)$NR^{15a}R^{15b}$. In a further aspect, $R^2$, when present, is selected from —$CH_2NR^{15a}R^{15b}$, —$CH_2CH_2NR^{15a}R^{15b}$, —$CH_2CH_2CH_2NR^{15a}R^{15b}$, and —CH($CH_3$)$CH_2NR^{15a}R^{15b}$. In a still further aspect, $R^2$, when present, is selected from —$CH_2NR^{15a}R^{15b}$, and —$CH_2CH_2NR^{15a}R^{15b}$. In yet a further aspect, $R^2$, when present, is —$CH_2NR^{15a}R^{15b}$.

In a further aspect, $R^3$ is selected from hydrogen.

In various aspects, $R^3$ is C1-C4 alkyl. In a further aspect, $R^3$ is selected from methyl, ethyl, n-propyl, and isopropyl. In a still further aspect, $R^3$ is selected from methyl and ethyl. In yet a further aspect, $R^3$ is ethyl. In an even further aspect, $R^3$ is methyl.

In one aspect, each of $R^2$, when present, and $R^3$ together comprise a 5- to 6-membered heterocycle substituted with a group selected from C1-C4 alkyl and —(C1-C4 alkyl)$NR^{16a}R^{16b}$. In a further aspect, each of $R^2$, when present, and $R^3$ together comprise a 5- to 6-membered heterocycle substituted with a group selected from methyl, ethyl, n-propyl, isopropyl, —$CH_2NR^{15a}R^{15b}$, —$CH_2CH_2NR^{15a}R^{15b}$, —$CH_2CH_2CH_2NR^{15a}R^{15b}$, and —CH($CH_3$)$CH_2NR^{15a}R^{15b}$. In a still further aspect, each of $R^2$, when present, and $R^3$ together comprise a 5- to 6-membered heterocycle substituted with a group selected from methyl, ethyl, —$CH_2NR^{15a}R^{15b}$ and —$CH_2CH_2NR^{15a}R^{15b}$. In yet a further aspect, each of $R^2$, when present, and $R^3$ together comprise a 5- to 6-membered heterocycle substituted with a group selected from methyl and —$CH_2NR^{15a}R^{15b}$.

In various aspects, each of $R^2$, when present, and $R^3$ together comprise a 5-membered heterocycle substituted with a group selected from C1-C4 alkyl and —(C1-C4 alkyl)$NR^{16a}R^{16b}$. Examples of 5-membered heterocycles include, but are not limited to, pyrrolidine, 3-pyrroline, 2-pyrroline, 2H-pyrrole, 1H-pyrrole, pyrazolidine, imidazolidine, 2-pyrazoline, 2-imidazoline, tetrahydrofuran, furan, 1,3-dioxolane, tetrahydrothiophene, thiophene, oxazole, isothiazole, and thiazole. In a further aspect, each of $R^2$, when present, and $R^3$ together comprise a 5-membered heterocycle substituted with a group selected from methyl, ethyl, n-propyl, isopropyl, —$CH_2NR^{15a}R^{15b}$, —$CH_2CH_2NR^{15a}R^{15b}$, —$CH_2CH_2CH_2NR^{15a}R^{15b}$, and —CH($CH_3$)$CH_2NR^{15a}R^{15b}$. In a still further aspect, each of $R^2$, when present, and $R^3$ together comprise a 5-membered heterocycle substituted with a group selected from methyl, ethyl, —CH$_2$NR$^{15a}$R$^{15b}$, and —CH$_2$CH$_2$NR$^{15a}$R$^{15b}$. In yet a further aspect, each of $R^2$, when present, and $R^3$ together comprise a 5-membered heterocycle substituted with a group selected from methyl and —CH$_2$NR$^{15a}$R$^{15b}$.

In various aspects, each of $R^2$, when present, and $R^3$ together comprise a 6-membered heterocycle substituted with a group selected from C1-C4 alkyl and —(C1-C4 alkyl)NR$^{16a}$R$^{16b}$. Examples of 6-membered heterocycles include, but are not limited to, piperidine, pyridine, piperazine, pyridazine, pyrimidine, pyrazine, 1,2,4-triazine, 1,3,5-triazine, tetrahydropyran, thiane, 2H-thiopyran, 4H-thiopyran, 1,3-dithiane, 1,3,5-trithiane, morpholine, 4H-1,2-oxazine, 2H-1,2-oxazine, thiomorpholine, 4H-1,4-thiazine, 2H-1,2-thiazine, and 2H-1,4-thiazine. In a further aspect, each of $R^2$, when present, and $R^3$ together comprise a 6-membered heterocycle substituted with a group selected from methyl, ethyl, n-propyl, isopropyl, —CH$_2$NR$^{15a}$R$^{15b}$, —CH$_2$CH$_2$NR$^{15a}$R$^{15b}$, —CH$_2$CH$_2$CH$_2$NR$^{15a}$R$^{15b}$, and —CH(CH$_3$)CH$_2$NR$^{15a}$R$^{15b}$. In a still further aspect, each of $R^2$, when present, and $R^3$ together comprise a 6-membered heterocycle substituted with a group selected from methyl, ethyl, —CH$_2$NR$^{15a}$R$^{15b}$, and —CH$_2$CH$_2$NR$^{15a}$R$^{15b}$. In yet a further aspect, each of $R^2$, when present, and $R^3$ together comprise a 6-membered heterocycle substituted with a group selected from methyl and —CH$_2$NR$^{15a}$R$^{15b}$.

d. $R^4$ and $R^5$ Groups

In one aspect, each of $R^4$ and $R^5$ is hydrogen or together comprise a 5- to 6-membered heterocycle.

In a further aspect, each of $R^4$ and $R^5$ is hydrogen.

In a further aspect, each of $R^4$ and $R^5$ together comprise a 5- to 6-membered heterocycle. In a still further aspect, each of $R^4$ and $R^5$ together comprise an unsubstituted 5- to 6-membered heterocycle.

In a further aspect, each of $R^4$ and $R^5$ together comprise a 5-membered heterocycle. Examples of 5-membered heterocycles include, but are not limited to, pyrrolidine, 3-pyrroline, 2-pyrroline, 2H-pyrrole, 1H-pyrrole, pyrazolidine, imidazolidine, 2-pyrazoline, 2-imidazoline, tetrahydrofuran, furan, 1,3-dioxolane, tetrahydrothiophene, thiophene, oxazole, isothiazole, and thiazole. In a still further aspect, each of $R^4$ and $R^5$ together comprise an unsubstituted 5-membered heterocycle. In yet a further aspect, each of $R^4$ and $R^5$ together comprise a 5-membered heterocycloalkyl.

In a further aspect, each of $R^4$ and $R^5$ together comprise a 6-membered heterocycle. Examples of 6-membered heterocycles include, but are not limited to, piperidine, pyridine, piperazine, pyridazine, pyrimidine, pyrazine, 1,2,4-triazine, 1,3,5-triazine, tetrahydropyran, thiane, 2H-thiopyran, 4H-thiopyran, 1,3-dithiane, 1,3,5-trithiane, morpholine, 4H-1,2-oxazine, 2H-1,2-oxazine, thiomorpholine, 4H-1,4-thiazine, 2H-1,2-thiazine, and 2H-1,4-thiazine. In a still further aspect, each of $R^4$ and $R^5$ together comprise an unsubstituted 6-membered heterocycle. In yet a further aspect, each of $R^4$ and $R^5$ together comprise a 6-membered heterocycloalkyl.

e. $R^{10}$ Groups

In one aspect, $R^{10}$, when present, is selected from hydrogen and halogen. In a further aspect, $R^{10}$, when present, is selected from hydrogen, —F, —Br, and —Cl. In a still further aspect, $R^{10}$, when present, is selected from hydrogen, —F, and —Cl. In yet a further aspect, $R^{10}$, when present, is selected from hydrogen and —F. In an even further aspect, $R^{10}$, when present, is selected from hydrogen and —Cl.

In various aspects, $R^{10}$, when present, is halogen. In a further aspect, $R^{10}$, when present, is selected from —F, —Br, and —Cl. In a still further aspect, $R^{10}$, when present, is selected from —F and —Cl. In yet a further aspect, $R^{10}$, when present, is —F. In an even further aspect, $R^{10}$, when present, is —Cl.

f. $R^{11}$, $R^{12a}$, and $R^{12B}$ Groups

In one aspect, each of $R^{11}$, $R^{12a}$, and $R^{12b}$, when present, is independently selected from hydrogen, C1-C4 alkyl, —C(=NH)NH$_2$, —CO$_2$(C1-C4 alkyl), —(C1-C4 alkyl)OR$^{20}$, —(C1-C4 alkyl)NR$^{21a}$R$^{21b}$, —(C1-C4 alkyl)Ar$^1$, and Ar$^1$. In a further aspect, each of $R^{11}$, $R^{12a}$, and $R^{12b}$, when present, is independently selected from hydrogen, methyl, ethyl, n-propyl, isopropyl, —C(=NH)NH$_2$, —CO$_2$CH$_3$, —CO$_2$CH$_2$CH$_3$, —CO$_2$CH$_2$CH$_2$CH$_3$, —CO$_2$CH(CH$_3$)$_2$, —CH$_2$OR$^{20}$, —CH$_2$CH$_2$OR$^{20}$, —CH$_2$CH$_2$CH$_2$OR$^{20}$, —CH(CH$_3$)CH$_2$OR$^{20}$, —CH$_2$NR$^{21a}$R$^{21b}$, —CH$_2$CH$_2$NR$^{21a}$R$^{21b}$, —CH$_2$CH$_2$CH$_2$NR$^{21a}$R$^{21b}$, —CH(CH$_3$)CH$_2$NR$^{21a}$R$^{21b}$, —CH$_2$Ar$^1$, —CH$_2$CH$_2$Ar$^1$, —CH$_2$CH$_2$CH$_2$Ar$^1$, —CH(CH$_3$)CH$_2$Ar$^1$, and Ar$^1$. In a still further aspect, each of $R^{11}$, $R^{12a}$, and $R^{12b}$, when present, is independently selected from hydrogen, methyl, ethyl, —C(=NH)NH$_2$, —CO$_2$CH$_3$, —CO$_2$CH$_2$CH$_3$, —CH$_2$OR$^{20}$, —CH$_2$CH$_2$OR$^{20}$, —CH$_2$NR$^{21a}$R$^{21b}$, —CH$_2$CH$_2$NR$^{21a}$R$^{21b}$, —CH$_2$Ar$^1$, —CH$_2$CH$_2$Ar$^1$, and Ar$^1$. In yet a further aspect, each of $R^{11}$, $R^{12a}$, and $R^{12b}$, when present, is independently selected from hydrogen, methyl, —C(=NH)NH$_2$, —CO$_2$CH$_3$, —CH$_2$OR$^{20}$, —CH$_2$NR$^{21a}$R$^{21b}$, —CH$_2$Ar$^1$, and Ar$^1$.

In various aspects, each of $R^{11}$, $R^{12a}$, and $R^{12b}$, when present, is independently selected from hydrogen, C1-C4 alkyl, —C(=NH)NH$_2$, —CO$_2$(C1-C4 alkyl), —(C1-C4 alkyl)OR$^{20}$, and —(C1-C4 alkyl)NR$^{21a}$R$^{21b}$. In a further aspect, each of $R^{11}$, $R^{12a}$, and $R^{12b}$, when present, is independently selected from hydrogen, methyl, ethyl, n-propyl, isopropyl, —C(=NH)NH$_2$, —CO$_2$CH$_3$, —CO$_2$CH$_2$CH$_3$, —CO$_2$CH$_2$CH$_2$CH$_3$, —CO$_2$CH(CH$_3$)$_2$, —CH$_2$OR$^{20}$, —CH$_2$CH$_2$OR$^{20}$, —CH$_2$CH$_2$CH$_2$OR$^{20}$, —CH(CH$_3$)CH$_2$OR$^{20}$, —CH$_2$NR$^{21a}$R$^{21b}$, —CH$_2$CH$_2$NR$^{21a}$R$^{21b}$, —CH$_2$CH$_2$CH$_2$NR$^{21a}$R$^{21b}$, and —CH(CH$_3$)CH$_2$NR$^{21a}$R$^{21b}$. In a still further aspect, each of $R^{11}$, $R^{12a}$, and $R^{12b}$, when present, is independently selected from hydrogen, methyl, ethyl, —C(=NH)NH$_2$, —CO$_2$CH$_3$, —CO$_2$CH$_2$CH$_3$, —CH$_2$OR$^{20}$, —CH$_2$CH$_2$OR$^{20}$, —CH$_2$NR$^{21a}$R$^{21b}$, and —CH$_2$CH$_2$NR$^{21a}$R$^{21b}$. In yet a further aspect, each of RD, $R^{12a}$, and $R^{12b}$, when present, is independently selected from hydrogen, methyl, —C(=NH)NH$_2$, —CO$_2$CH$_3$, —CH$_2$OR$^{20}$, and —CH$_2$NR$^{21a}$R$^{21b}$.

In various aspects, each of $R^{11}$, $R^{12a}$, and $R^{12b}$, when present, is independently selected from hydrogen, —CO$_2$(C1-C4 alkyl), —(C1-C4 alkyl)OR$^{20}$, and —(C1-C4 alkyl)NR$^{21a}$R$^{21b}$. In a further aspect, each of $R^{11}$, $R^{12a}$, and $R^{12b}$, when present, is independently selected from hydrogen, —CO$_2$CH$_3$, —CO$_2$CH$_2$CH$_3$, —CO$_2$CH$_2$CH$_2$CH$_3$, —CO$_2$CH(CH$_3$)$_2$, —CH$_2$OR$^{20}$, —CH$_2$CH$_2$OR$^{20}$, —CH$_2$CH$_2$CH$_2$OR$^{20}$, —CH(CH$_3$)CH$_2$OR$^{20}$, —CH$_2$NR$^{21a}$R$^{21b}$, —CH$_2$CH$_2$NR$^{21a}$R$^{21b}$, —CH$_2$CH$_2$CH$_2$NR$^{21a}$R$^{21b}$ and —CH(CH$_3$)CH$_2$NR$^{21a}$R$^{21b}$ In a still further aspect, each of $R^{11}$, $R^{12a}$, and $R^{12b}$, when present, is independently selected from hydrogen, —CO$_2$CH$_3$, —CO$_2$CH$_2$CH$_3$, —CH$_2$OR$^{20}$, —CH$_2$CH$_2$OR$^{20}$, —CH$_2$NR$^{21a}$R$^{21b}$ and —CH$_2$CH$_2$NR$^{21a}$R$^{21b}$. In yet a further aspect, each of $R^{11}$, $R^{12a}$, and $R^{12b}$, when present, is independently selected from hydrogen, —CO$_2$CH$_3$, —CH$_2$OR$^{20}$, and —CH$_2$NR$^{21a}$R$^{21b}$.

In various aspects, each of $R^{11}$, $R^{12a}$, and $R^{12b}$, when present, is independently selected from hydrogen, —CO$_2$ (C1-C4 alkyl), and —(C1-C4 alkyl)OR$^{20}$. In a further aspect, each of $R^{11}$, $R^{12a}$, and $R^{12b}$, when present, is independently selected from hydrogen, —CO$_2$CH$_3$, —CO$_2$CH$_2$CH$_3$, —CO$_2$CH$_2$CH$_2$CH$_3$, —CO$_2$CH(CH$_3$)$_2$, —CH$_2$OR$^{20}$, —CH$_2$CH$_2$OR$^{20}$, —CH$_2$CH$_2$CH$_2$OR$^{20}$, and —CH(CH$_3$)CH$_2$OR$^{20}$. In a still further aspect, each of R$^{11}$, R$^{12a}$, and R$^{12b}$, when present, is independently selected from hydrogen, —CO$_2$CH$_3$, —CO$_2$CH$_2$CH$_3$, —CH$_2$OR$^{20}$, and —CH$_2$CH$_2$OR$^{20}$. In yet a further aspect, each of R$^{11}$, R$^{12a}$, and R$^{12b}$, when present, is independently selected from hydrogen, —CO$_2$CH$_3$, and —CH$_2$OR$^{20}$.

In various aspects, each of R$^{11}$, R$^{12a}$, and R$^{12b}$, when present, is independently selected from hydrogen and —(C1-C4 alkyl)NR$^{21a}$R$^{21b}$. In a further aspect, each of R$^{11}$, R$^{12a}$ and R$^{12b}$, when present, is independently selected from hydrogen, —CH$_2$NR$^{21a}$R$^{21b}$, —CH$_2$CH$_2$NR$^{21a}$R$^{21b}$, —CH$_2$CH$_2$CH$_2$NR$^{21a}$R$^{21b}$, and —CH(CH$_3$)CH$_2$NR$^{21a}$R$^{21b}$. In a still further aspect, each of R$^{11}$, R$^{12a}$, and R$^{12b}$, when present, is independently selected from hydrogen, —CH$_2$NR$^{21a}$R$^{21b}$, and —CH$_2$CH$_2$NR$^{21a}$R$^{21b}$. In yet a further aspect, each of R$^{11}$, R$^{12a}$, and R$^{12b}$, when present, is independently selected from hydrogen and —CH$_2$NR$^{21a}$R$^{21b}$.

In various aspects, each of R$^{11}$, R$^{12a}$, and R$^{12b}$, when present, is independently selected from hydrogen, C1-C4 alkyl, —(C1-C4 alkyl)Ar$^1$, and Ar$^1$. In a further aspect, each of R$^{11}$, R$^{12a}$, and R$^{12b}$, when present, is independently selected from hydrogen, methyl, ethyl, n-propyl, isopropyl, —CH$_2$Ar$^1$, —CH$_2$CH$_2$Ar$^1$, —CH$_2$CH$_2$CH$_2$Ar$^1$, —CH(CH$_3$)CH$_2$Ar$^1$, and Ar$^1$. In a still further aspect, each of R$^{11}$, R$^{12a}$, and R$^{12b}$, when present, is independently selected from hydrogen, methyl, ethyl, —CH$_2$Ar$^1$, —CH$_2$CH$_2$Ar$^1$, and Ar$^1$. In yet a further aspect, each of R$^1$, R$^{12}$, and R$^{12b}$, when present, is independently selected from hydrogen, methyl, —CH$_2$Ar$^1$, and Ar$^1$.

In various aspects, each of R$^{11}$, R$^{12a}$, and R$^{12b}$, when present, is independently selected from hydrogen, —(C1-C4 alkyl)Ar$^1$, and Ar$^1$. In a further aspect, each of R$^{11}$, R$^{12a}$ and R$^{12b}$, when present, is independently selected from hydrogen, —CH$_2$Ar$^1$, —CH$_2$CH$_2$Ar$^1$, —CH$_2$CH$_2$CH$_2$Ar$^1$, —CH(CH$_3$)CH$_2$Ar$^1$, and Ar$^1$. In a still further aspect, each of R$^1$, R$^{12}$, and R$^{12b}$, when present, is independently selected from hydrogen, —CH$_2$Ar$^1$, —CH$_2$CH$_2$Ar$^1$, and Ar$^1$. In yet a further aspect, each of R$^{11}$, R$^{12a}$, and R$^{12b}$, when present, is independently selected from hydrogen, —CH$_2$Ar$^1$, and Ar$^1$.

In various aspects, each of R$^{11}$, R$^{12a}$, and R$^{12b}$, when present, is independently selected from hydrogen and C1-C4 alkyl. In a further aspect, each of R$^{11}$, R$^{12a}$, and R$^{12b}$, when present, is independently selected from hydrogen, methyl, ethyl, n-propyl, and isopropyl. In a still further aspect, each of R$^{11}$, R$^{12a}$, and R$^{12b}$, when present, is independently selected from hydrogen, methyl, and ethyl. In yet a further aspect, each of R$^{11}$, R$^{12a}$, and R$^{12b}$, when present, is independently selected from hydrogen and methyl.

In a further aspect, each of R$^{11}$, R$^{12a}$, and R$^{12b}$, when present, is hydrogen.

g. R$^{13}$, R$^{14A}$, and R$^{14B}$ Groups

In one aspect, each of R$^{13}$, R$^{14a}$, and R$^{14b}$, when present, is independently selected from hydrogen and C1-C4 alkyl. In a further aspect, each of R$^{13}$, R$^{14a}$, and R$^{14b}$, when present, is independently selected from hydrogen, methyl, ethyl, i-propyl, and n-propyl. In a still further aspect, each of R$^{13}$, R$^{14a}$, and R$^{14b}$, when present, is independently selected from hydrogen, methyl, and ethyl. In yet a further aspect, each of R$^{13}$, R$^{14a}$, and R$^{14b}$, when present, is independently selected from hydrogen and methyl.

In a further aspect, each of R$^{13}$, R$^{14a}$, and R$^{14b}$, when present, is hydrogen.

In various aspects, each of R$^{13}$, R$^{14a}$, and R$^{14b}$, when present, is independently C1-C4 alkyl. In a further aspect, each of R$^{13}$, R$^{14a}$, and R$^{14b}$, when present, is independently selected from methyl, ethyl, i-propyl, and n-propyl. In a still further aspect, each of R$^{13}$, R$^{14a}$, and R$^{14b}$, when present, is independently selected from methyl and ethyl. In yet a further aspect, each of R$^{13}$, R$^{14a}$, and R$^{14b}$, when present, is ethyl. In an even further aspect, each of R$^{13}$, R$^{14a}$, and R$^{14b}$, when present, is methyl.

h. R$^{15A}$ and R$^{15B}$ Groups

In one aspect, each of R$^{15a}$ and R$^{15b}$, when present, is independently selected from hydrogen and C1-C4 alkyl. In a further aspect, each of R$^{15a}$ and R$^{15b}$, when present, is independently selected from hydrogen, methyl, ethyl, n-propyl, and isopropyl. In a still further aspect, each of R$^{15a}$ and R$^{15b}$, when present, is independently selected from hydrogen, methyl, and ethyl. In yet a further aspect, each of R$^{15a}$ and R$^{15b}$, when present, is independently selected from hydrogen and ethyl. In an even further aspect, each of R$^{15a}$ and R$^{15b}$, when present, is independently selected from hydrogen and methyl.

In one aspect, each of R$^{15a}$ and R$^{15b}$, when present, is hydrogen.

In various aspects, each of R$^{15a}$ and R$^{15b}$, when present, is independently C1-C4 alkyl. In a further aspect, each of R$^{15a}$ and R$^{15b}$, when present, is independently selected from methyl, ethyl, n-propyl, and isopropyl. In a still further aspect, each of R$^{15a}$ and R$^{15b}$, when present, is independently selected from methyl and ethyl. In yet a further aspect, each of R$^{15a}$ and R$^{15b}$, when present, is ethyl. In an even further aspect, each of R$^{15a}$ and R$^{15b}$, when present, is methyl.

i. R$^{16A}$ and R$^{16B}$ Groups

In one aspect, each of R$^{16a}$ and R$^{16b}$, when present, is independently selected from hydrogen and C1-C4 alkyl. In a further aspect, each of R$^{16a}$ and R$^{16b}$, when present, is independently selected from hydrogen, methyl, ethyl, n-propyl, and isopropyl. In a still further aspect, each of R$^{16a}$ and R$^{16b}$, when present, is independently selected from hydrogen, methyl, and ethyl. In yet a further aspect, each of R$^{16a}$ and R$^{16b}$, when present, is independently selected from hydrogen and ethyl. In an even further aspect, each of R$^{16a}$ and R$^{16b}$, when present, is independently selected from hydrogen and methyl.

In various aspects, each of R$^{16a}$ and R$^{16b}$, when present, is independently C1-C4 alkyl. In a further aspect, each of R$^{16a}$ and R$^{16b}$, when present, is independently selected from methyl, ethyl, n-propyl, and isopropyl. In a still further aspect, each of R$^{16a}$ and R$^{16b}$, when present, is independently selected from methyl and ethyl. In yet a further aspect, each of R$^{16a}$ and R$^{16b}$, when present, is ethyl. In an even further aspect, each of R$^{16a}$ and R$^{16b}$, when present, is methyl.

In a further aspect, each of R$^{16a}$ and R$^{16b}$, when present, is hydrogen.

j. Ar$^1$ Groups

In one aspect, Ar$^1$, when present, is selected from aryl and heteroaryl and substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. In a further aspect, Ar$^1$, when present, is selected from aryl and heteroaryl and substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. In a still further aspect, Ar$^1$, when present, is selected from aryl and heteroaryl and substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. In yet a further aspect, Ar$^1$, when present, is selected from aryl and heteroaryl and monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. In an even further aspect, Ar$^1$, when present, is selected from aryl and heteroaryl and is unsubstituted.

In various aspects, Ar$^1$, when present, is aryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. Examples of aryls include, but are not limited to, phenyl, naphthyl, phenanthrenyl, anthracenyl, and pyrenyl. In a further aspect, Ar$^1$, when present, is aryl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. In a still further aspect, Ar$^1$, when present, is aryl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. In yet a further aspect, Ar$^1$, when present, is aryl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. In an even further aspect, Ar$^1$, when present, is unsubstituted aryl.

In various aspects, Ar$^1$, when present, is heteroaryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. Examples of heteroaryls include, but are not limited to, pyrrole, furan, thiophene, pyridine, pyridazine, pyrimidine, pyrazine, triazine, indole, indazole, benzimidazole, azaindazole, purine, benzofuran, benzo[b]thiophene, benzo[d]oxazole, and benzo[d]isothiazole. In a further aspect, Ar$^1$, when present, is heteroaryl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. In a still further aspect, Ar$^1$, when present, is heteroaryl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. In yet a further aspect, Ar$^1$, when present, is heteroaryl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. In an even further aspect, Ar$^1$, when present, is unsubstituted heteroaryl.

k. Ar$^2$ Groups

In one aspect, Ar$^2$ is a heteroaryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. Examples of heteroaryls include, but are not limited to, pyrrole, furan, thiophene, pyridine, pyridazine, pyrimidine, pyrazine, triazine, indole, indazole, benzimidazole, azaindazole, purine, benzofuran, benzo[b]thiophene, benzo[d]oxazole, and benzo[d]isothiazole. In a further aspect, Ar$^2$ is a heteroaryl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. In a still further aspect, Ar$^2$ is a heteroaryl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. In yet a further aspect, Ar$^2$ is a heteroaryl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. In an even further aspect, Ar$^2$ is an unsubstituted heteroaryl.

In various aspects, Ar$^2$ is selected from thiophenyl and thiazolyl, and substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. In a further aspect, Ar$^2$ is selected from thiophenyl and thiazolyl, substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. In a still further aspect, Ar$^2$ is selected from thiophenyl and thiazolyl, substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. In yet a further aspect, Ar$^2$ is selected from thiophenyl and thiazolyl, monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. In an even further aspect, Ar$^2$ is selected from thiophenyl and thiazolyl, and is unsubstituted.

In various aspects, Ar$^2$ is selected from imidazolyl, pyrazolyl, and triazolyl, and substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. In a further aspect, Ar$^2$ is selected from imidazolyl, pyrazolyl, and triazolyl, substituted with 0, 1, or 2 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. In a still further aspect, $Ar^2$ is selected from imidazolyl, pyrazolyl, and triazolyl, substituted with 0 or 1 group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. In yet a further aspect, $Ar^2$ is selected from imidazolyl, pyrazolyl, and triazolyl, monosubstituted with a group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino. In an even further aspect, $Ar^2$ is selected from imidazolyl, pyrazolyl, and triazolyl, and is unsubstituted.

2. Example Compounds

In one aspect, a compound can be present as one or more of the following structures:

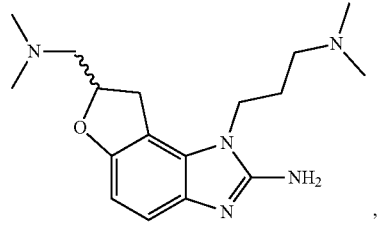
,
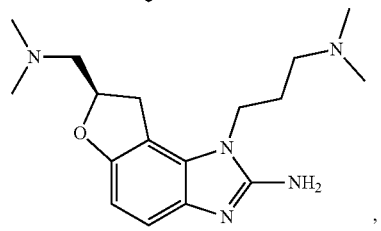
,
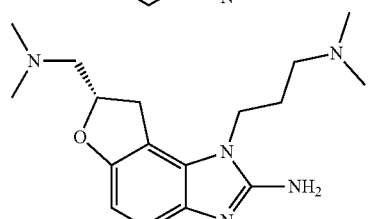
,
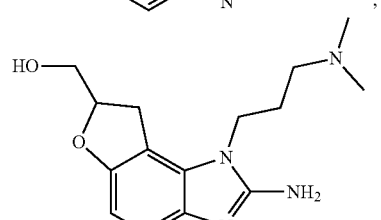
,
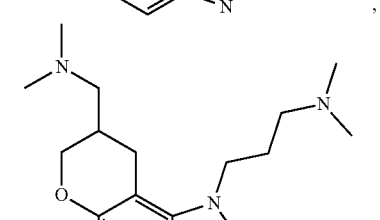
,
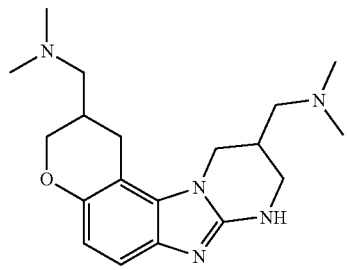
,
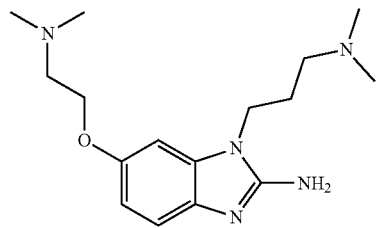
,
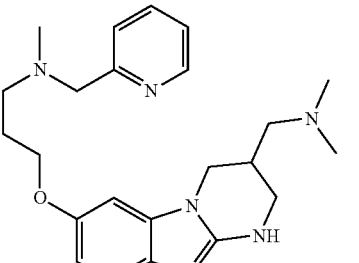
,
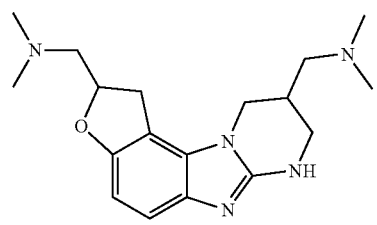
, and
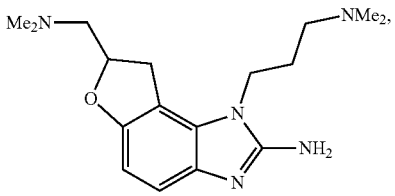
, or a pharmaceutically acceptable salt thereof.

In one aspect, a compound can be present as one or more of the following structures:

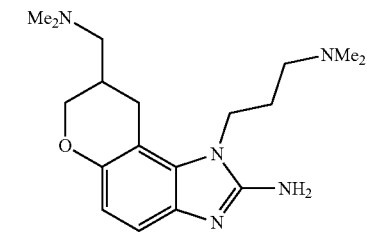

-continued

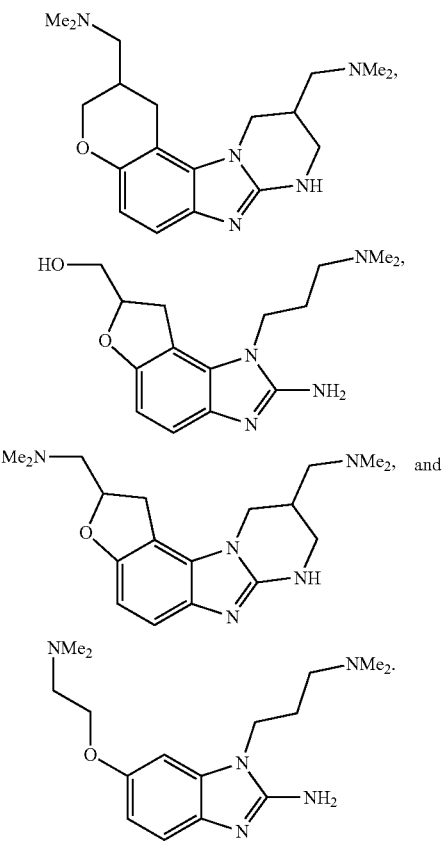

In one aspect, a compound can be present as:

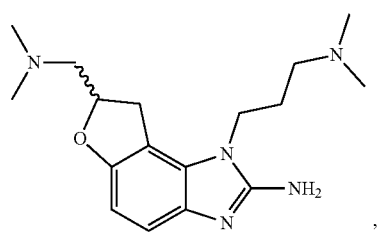

or a pharmaceutically acceptable salt thereof.

In one aspect, a compound can be present as:

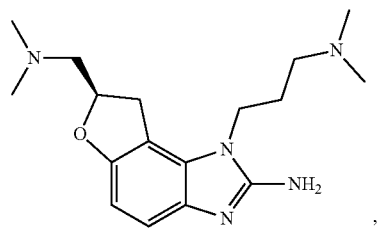

or a pharmaceutically acceptable salt thereof.

In one aspect, a compound can be present as:

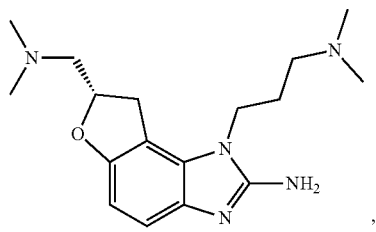

or a pharmaceutically acceptable salt thereof.

3. Prophetic Compound Examples

The following compound examples are prophetic, and can be prepared using the synthesis methods described herein above and other general methods as needed as would be known to one skilled in the art. It is anticipated that the prophetic compounds would be active in the treatment of hepatitis (e.g., hepatitis C), RNA virus infections (e.g., Zika virus, dengue virus, Powassan virus, Chikungunya virus, Enterovirus, respiratory syntactical virus (RSV), Rift Valley fever, Influenza virus, Tacaribe virus, Mayaro virus, West Nile virus, yellow fever virus, and coronavirus), and/or disorders of uncontrolled cellular proliferation (e.g., cancer), and such activity can be determined using the assay methods described herein below.

In one aspect, a compound can be selected from:

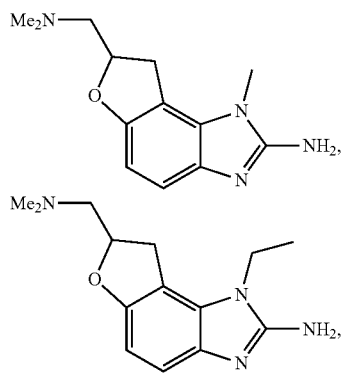

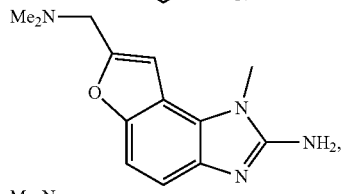

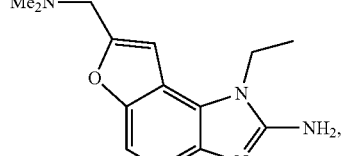

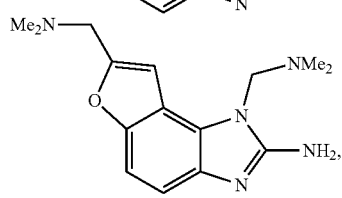

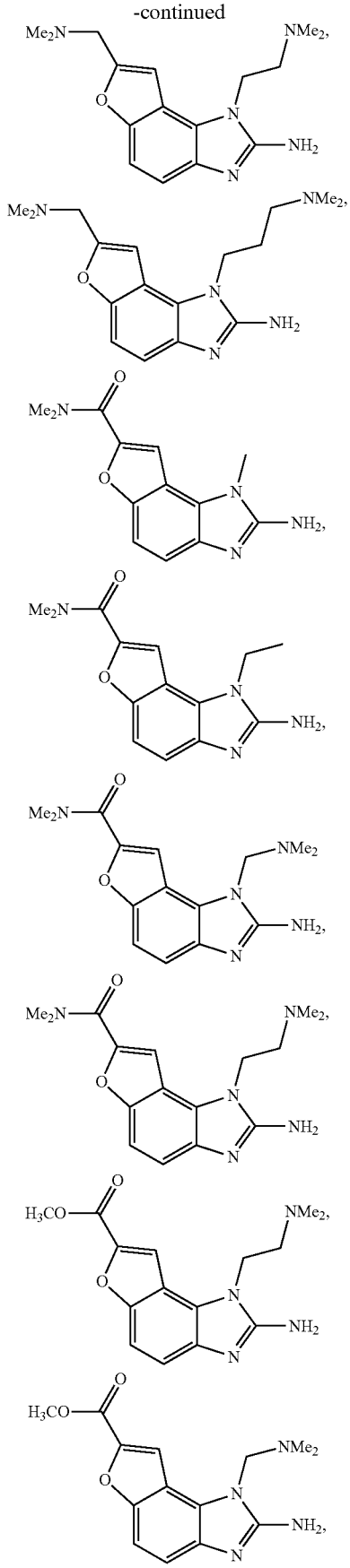
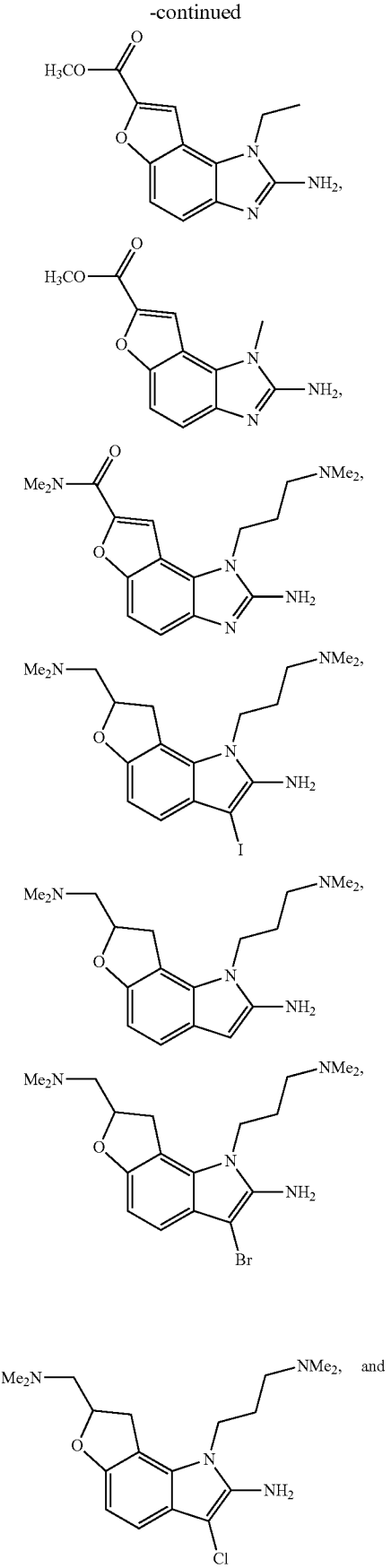

-continued
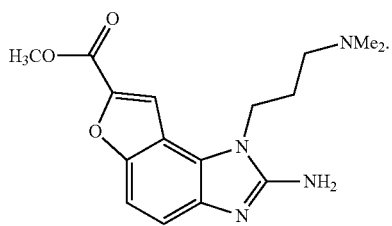
In one aspect, a compound can be selected from:
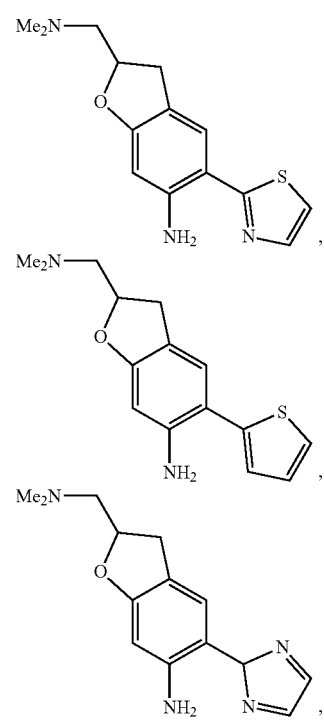
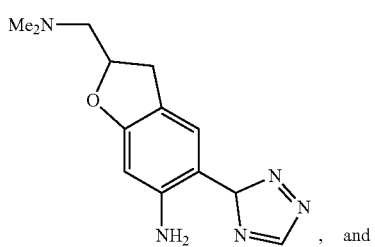
, and
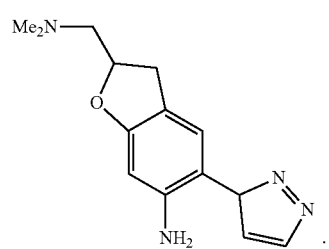
In one aspect, a compound can be selected from:
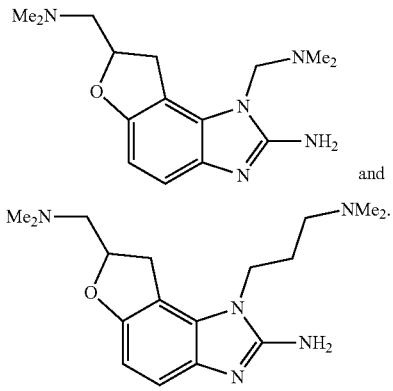
and
In one aspect, a compound can be selected from:
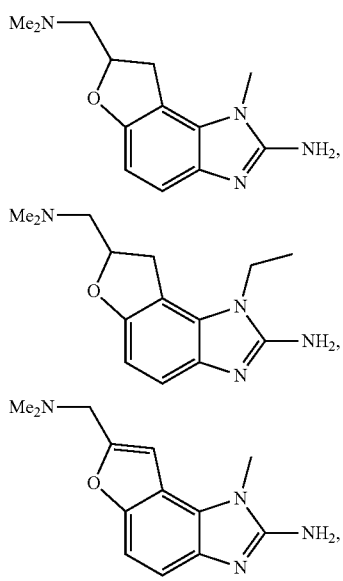
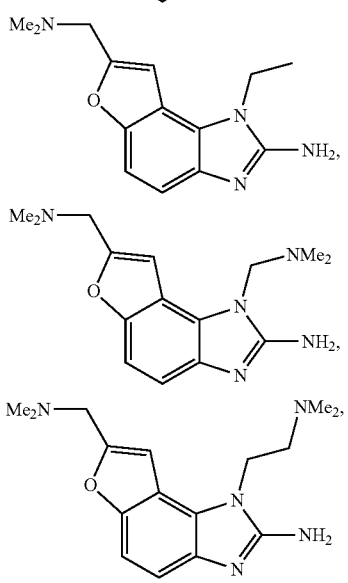

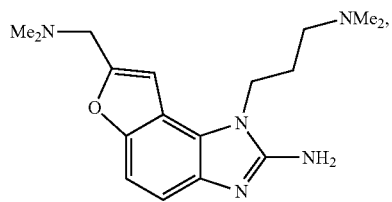
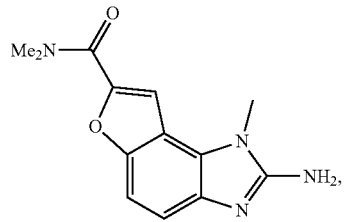
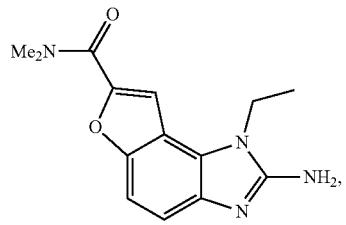
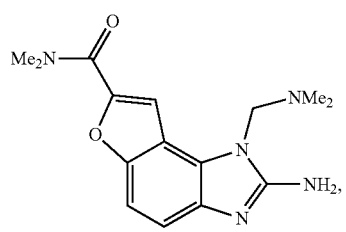
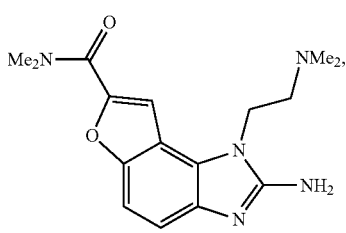
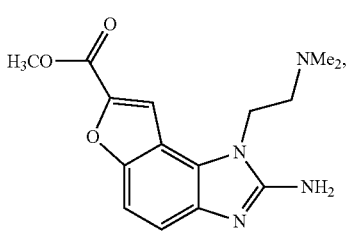
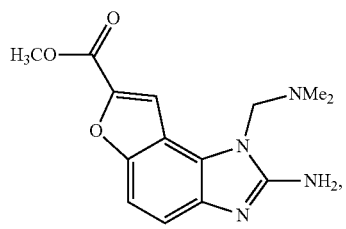
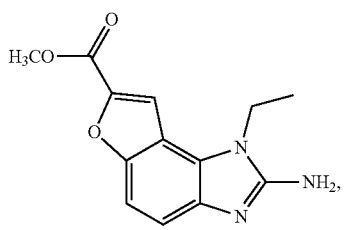
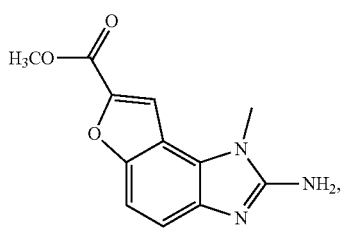
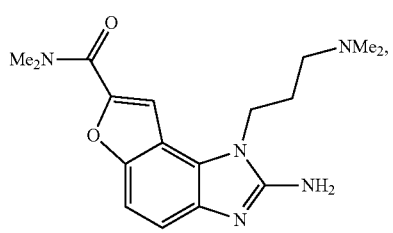
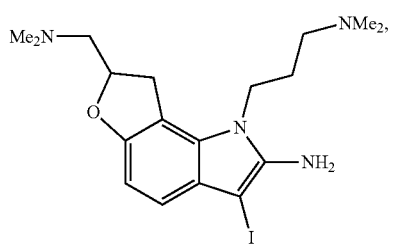
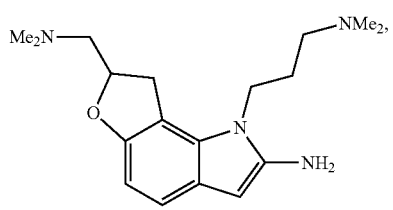
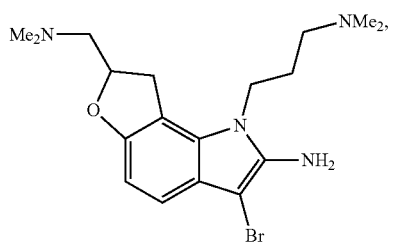
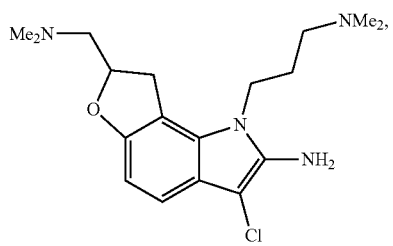

-continued

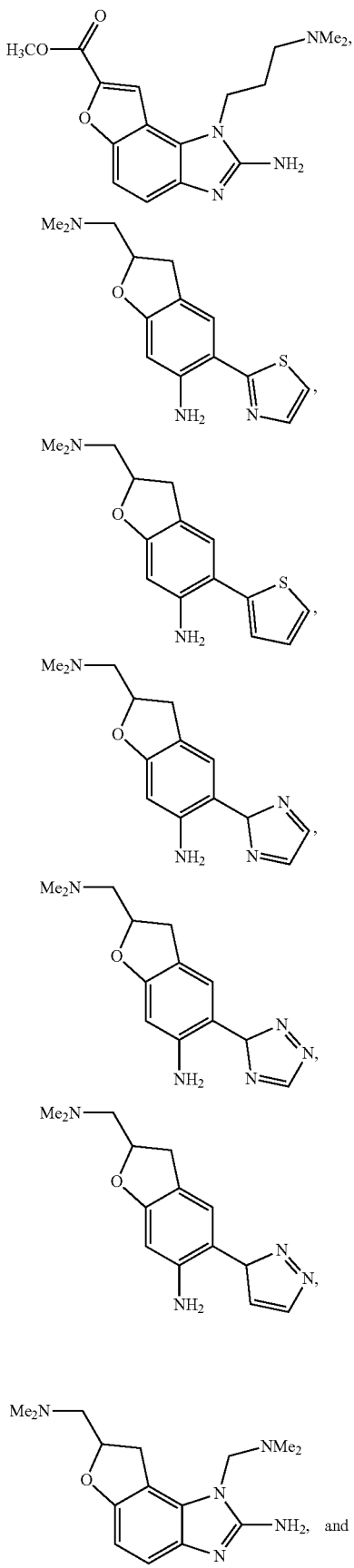

-continued

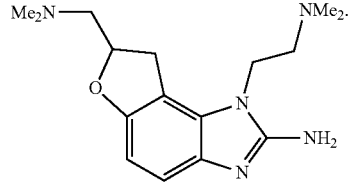

In one aspect, a compound can be selected from:

It is contemplated that one or more compounds can optionally be omitted from the disclosed invention.

It is understood that the disclosed compounds can be used in connection with the disclosed methods, compositions, kits, and uses.

It is understood that pharmaceutical acceptable derivatives of the disclosed compounds can be used also in connection with the disclosed methods, compositions, kits, and uses. The pharmaceutical acceptable derivatives of the compounds can include any suitable derivative, such as pharmaceutically acceptable salts as discussed below, isomers, radiolabeled analogs, tautomers, and the like.

C. Pharmaceutical Compositions

In one aspect, disclosed are pharmaceutical compositions comprising a disclosed compound, or a pharmaceutically acceptable salt thereof and a pharmaceutically acceptable carrier.

In one aspect, disclosed are pharmaceutical compositions comprising a therapeutically effective amount of a compound having a structure represented by a formula selected from:

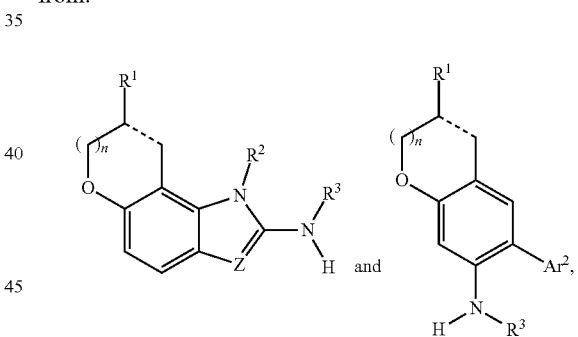

wherein ⁓ is a single or a double covalent bond; wherein n is 0 or 1; wherein Z, when present, is selected from N and $CR^{10}$; wherein $R^{10}$, when present, is selected from hydrogen and halogen; wherein $R^1$ is selected from —(C1-C4 alkyl)$OR^{11}$, —(C1-C4 alkyl)$NR^{12a}R^{12b}$, —$CO_2R^{13}$, and —C(O)$NR^{14a}R^{14b}$; wherein each of $R^{11}$, $R^{12a}$, and $R^{12b}$, when present, is independently selected from hydrogen, C1-C4 alkyl, —C(=NH)$NH_2$, —$CO_2$(C1-C4 alkyl), —(C1-C4 alkyl)$OR^{20}$, —(C1-C4 alkyl)$NR^{21a}R^{21b}$, —(C1-C4 alkyl)$Ar^1$, and $Ar^1$; wherein $Ar^1$, when present, is selected from aryl and heteroaryl and substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of $R^{13}$, $R^{14a}$, and $R^{14b}$, when present, is independently selected from hydrogen and C1-C4 alkyl; wherein $R^2$, when present, is selected from C1-C4 alkyl and —(C1-C4 alkyl)$NR^{15a}R^{15b}$; wherein each of $R^{15a}$ and $R^{15b}$, when present, is independently selected from hydrogen and C1-C4 alkyl; wherein $R^3$ is selected from hydrogen and C1-C4 alkyl; or wherein each of $R^2$, when present, and $R^3$ together comprise a 5- to 6-membered heterocycle substituted with a group selected from C1-C4 alkyl and —(C1-C4 alkyl)$NR^{16a}R^{16b}$; wherein each of $R^{16a}$ and $R^{16b}$, when present, is independently selected from hydrogen and C1-C4 alkyl; and wherein $Ar^2$ is a heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, provided that when the compound has a structure represented by a formula:

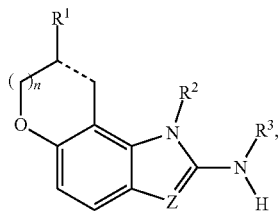

then either ⁓ is a double bond, Z is $CR^{10}$, or $R^2$ is C1-C4 alkyl, or a pharmaceutically acceptable salt thereof, and a pharmaceutically acceptable carrier.

In one aspect, disclosed are pharmaceutical compositions comprising a therapeutically effective amount of a compound selected from:

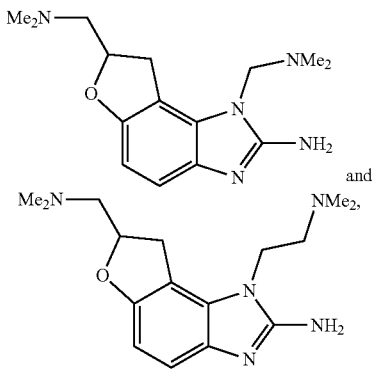

or a pharmaceutically acceptable salt thereof, and a pharmaceutically acceptable carrier.

In one aspect, disclosed are pharmaceutical compositions comprising a therapeutically effective amount of a compound having a structure represented by a formula selected from:

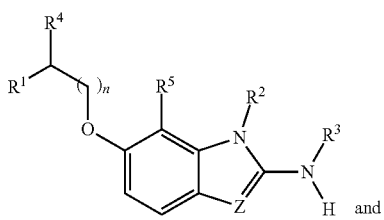

-continued

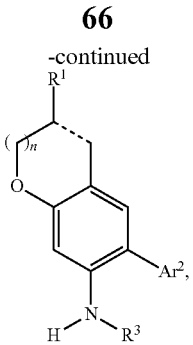

wherein ⁓ is a single or a double covalent bond; wherein n is 0 or 1; wherein Z, when present, is selected from N and $CR^{10}$; wherein $R^{10}$, when present, is selected from hydrogen and halogen; wherein $R^1$ is selected from —(C1-C4 alkyl)$OR^{11}$, —(C1-C4 alkyl)$NR^{12a}R^{12b}$, —$CO_2R^{13}$, and —C(O)$NR^{14a}R^{14b}$; wherein each of $R^{11}$, $R^{12a}$, and $R^{12b}$, when present, is independently selected from hydrogen, C1-C4 alkyl, —C(=NH)$NH_2$, —$CO_2$(C1-C4 alkyl), —(C1-C4 alkyl)$OR^{20}$, —(C1-C4 alkyl)$NR^{21a}R^{21b}$, —(C1-C4 alkyl)$Ar^1$, and $Ar^1$; wherein $Ar^1$, when present, is selected from aryl and heteroaryl and substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of $R^{13}$, $R^{14a}$, and $R^{14b}$, when present, is independently selected from hydrogen and C1-C4 alkyl; wherein $R^2$, when present, is selected from C1-C4 alkyl and —(C1-C4 alkyl)$NR^{15a}R^{15b}$; wherein each of $R^{15a}$ and $R^{15b}$, when present, is independently selected from hydrogen and C1-C4 alkyl; wherein $R^3$ is selected from hydrogen and C1-C4 alkyl; or wherein each of $R^2$, when present, and $R^3$ together comprise a 5- to 6-membered heterocycle substituted with a group selected from C1-C4 alkyl and —(C1-C4 alkyl)$NR^{16a}R^{16b}$; wherein each of $R^{16a}$ and $R^{16b}$, when present, is independently selected from hydrogen and C1-C4 alkyl; wherein each of $R^4$ and $R^5$ is hydrogen or together comprise a 5- to 6-membered heterocycle; and wherein $Ar^2$ is a heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, provided that when each of $R^4$ and $R^5$ is hydrogen, then R is —(C1-C4 alkyl)$OR^{11}$ or —(C1-C4 alkyl)$NR^{12a}R^{12b}$, or a pharmaceutically acceptable salt thereof, and a pharmaceutically acceptable carrier.

In one aspect, disclosed are pharmaceutical compositions comprising a therapeutically effective amount of a compound having a structure represented by a formula selected from:

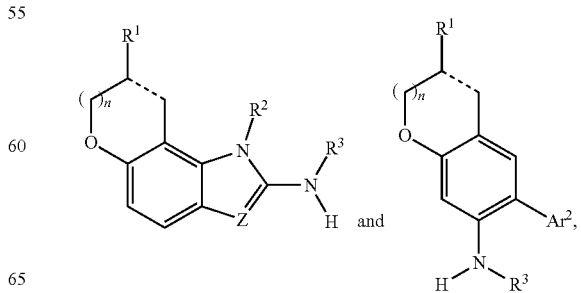

wherein ⌐ is a single or a double covalent bond; wherein n is 0 or 1; wherein Z, when present, is selected from N and $CR^{10}$; wherein $R^{10}$, when present, is selected from hydrogen and halogen; wherein $R^1$ is selected from —(C1-C4 alkyl)$OR^{11}$, —(C1-C4 alkyl)$NR^{12a}R^{12b}$, —$CO_2R^{13}$, and —C(O)$NR^{14a}R^{14b}$; wherein each of $R^{11}$, $R^{12a}$, and $R^{12b}$, when present, is independently selected from hydrogen, C1-C4 alkyl, —C(=NH)$NH_2$, —$CO_2$(C1-C4 alkyl), —(C1-C4 alkyl)$OR^{20}$, —(C1-C4 alkyl)$NR^{21a}R^{21b}$, —(C1-C4 alkyl)$Ar^1$, and $Ar^1$; wherein $Ar^1$, when present, is selected from aryl and heteroaryl and substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of $R^{13}$, $R^{14a}$, and $R^{14b}$, when present, is independently selected from hydrogen and C1-C4 alkyl; wherein $R^2$, when present, is selected from C1-C4 alkyl and —(C1-C4 alkyl)$NR^{15a}R^{15b}$; wherein each of $R^{15a}$ and $R^{15b}$, when present, is independently selected from hydrogen and C1-C4 alkyl; wherein $R^3$ is selected from hydrogen and C1-C4 alkyl; or wherein each of $R^2$, when present, and $R^3$ together comprise a 5- to 6-membered heterocycle substituted with a group selected from C1-C4 alkyl and —(C1-C4 alkyl)$NR^{16a}R^{16b}$; wherein each of $R^{16a}$ and $R^{16b}$, when present, is independently selected from hydrogen and C1-C4 alkyl; and wherein $Ar^2$ is a heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, or a pharmaceutically acceptable salt thereof, and a pharmaceutically acceptable carrier.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, PA 1990.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to treat a disorder such as, for example, hepatitis (e.g., hepatitis C), RNA virus infections (e.g., Zika virus, dengue virus, Powassan virus, Chikungunya virus, Enterovirus, respiratory syntactical virus (RSV), Rift Valley fever, Influenza virus, Tacaribe virus, Mayaro virus, West Nile virus, yellow fever virus, and coronavirus), and/or disorders of uncontrolled cellular proliferation (e.g., cancer). In a still further aspect, the pharmaceutical composition is used to treat hepatitis. In yet a further aspect, the pharmaceutical composition is used to treat a RNA virus infection. In an even further aspect, the pharmaceutical composition is used to treat a disorder of uncontrolled cellular proliferation.

In a further aspect, the pharmaceutical composition is used to treat a disorder is associated with dysregulation of hepatitis viral translation. In a still further aspect, the pharmaceutical composition is used to treat a disorder associated with activation of hepatitis viral translation.

In a further aspect, the pharmaceutical composition is used to treat a disorder is associated with dysregulation of RNA viral translation. In a still further aspect, the pharmaceutical composition is used to treat a disorder associated with activation of RNA viral translation.

It is understood that the disclosed compositions can be prepared from the disclosed compounds. It is also understood that the disclosed compositions can be employed in the disclosed methods of using.

D. Methods of Making a Compound

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Routes I-V, as described and exemplified below. The following examples are provided so that the invention might be more fully understood, are illustrative only, and should not be construed as limiting.

1. Route I

In one aspect, substituted benzimidazole analogs can be prepared as shown below.

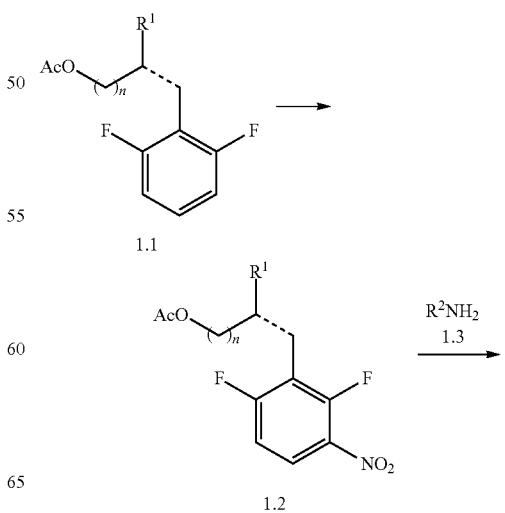

SCHEME 1A

-continued

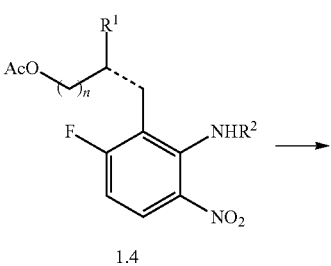
1.4

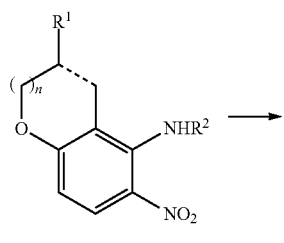
1.5

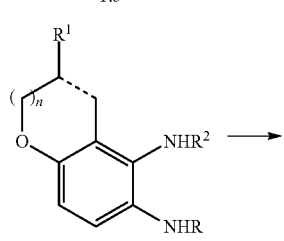
1.6

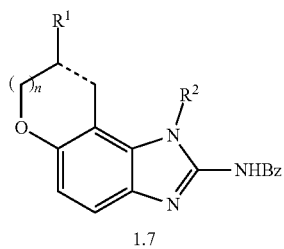
1.7

Compounds are represented in generic form, wherein R is a leaving group and with other substituents as noted in compound descriptions elsewhere herein. A more specific example is set forth below.

SCHEME 1B

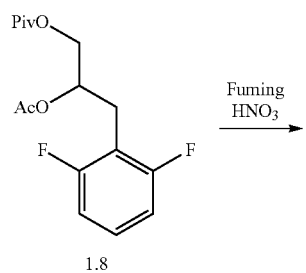
1.8

-continued

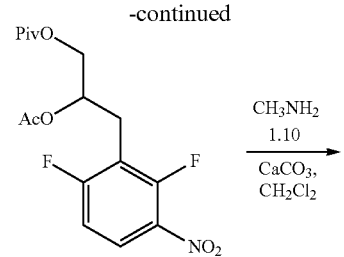
1.9

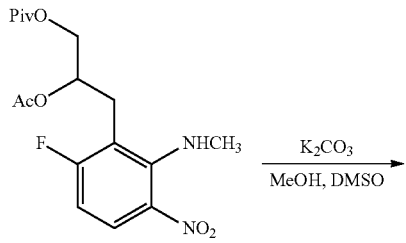
1.11

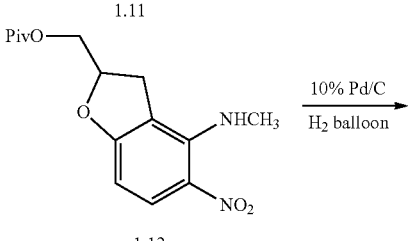
1.12

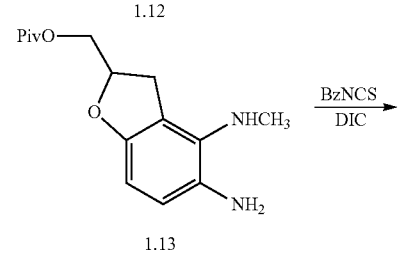
1.13

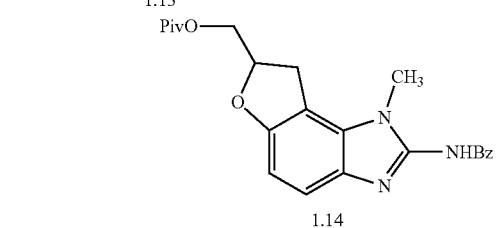
1.14

In one aspect, compounds of type 1.14, and similar compounds, can be prepared according to reaction Scheme 1B above. Thus, compounds of type 1.9 can be prepared by a nitration reaction of an appropriate aryl halide, e.g., 1.8 as shown above. Appropriate aryl halides are commercially available or prepared by methods known to one skilled in the art. The nitration is carried out in the presence of an appropriate nitrating agent, e.g., fuming nitric acid. Compounds of type 1.11 can be prepared by substitution of an appropriate aryl halide, e.g., 1.9 as shown above, with an appropriate amine, e.g., 1.10 as shown above. The substitution reaction is carried out in the presence of an appropriate base, e.g., calcium carbonate, in an appropriate solvent, e.g., dichloromethane. Appropriate amines are commercially available or prepared by methods known to one skilled in the art. Compounds of type 1.12 can be prepared by cyclization of an appropriate aryl halide, e.g., 1.11 as shown above. The cyclization is carried out in the presence of an appropriate base, e.g., potassium carbonate, and an appropriate alcohol, e.g., methanol, in an appropriate solvent, e.g., dimethylsulfoxide. Compounds of type 1.13 can be prepared by reduction of an appropriate aryl nitrate, e.g., 1.12 as shown above. The reduction is carried out in the presence of an appropriate reducing agent, e.g., hydrogen gas, and an appropriate catalyst, e.g., palladium on carbon. Compounds of type 1.14 can be prepared by cyclization of an appropriate amine, e.g., 1.13 as shown above. The cyclization is carried out in the presence of an appropriate thiocyanate, e.g., benzyl thiocyanate, and an appropriate activating agent, e.g., N,N'-diisopropylcarbodiimide. As can be appreciated by one skilled in the art, the above reaction provides an example of a generalized approach wherein compounds similar in structure to the specific reactants above (compounds similar to compounds of type 1.1, 1.2, 1.3, 1.4, 1.5, and 1.6), can be substituted in the reaction to provide substituted benzimidazole analogs similar to Formula 1.7. Additional exemplary synthetic protocols for the preparation of substituted benzimidazole analogs can be found in, for example, U.S. Pat. No. 7,642,265 B2, Seth et al. (2005) *J Med. Chem.* 48(23): 7099-7102, and International Patent Publication No. WO 2013/186335.

2. Route II

In one aspect, substituted benzimidazole analogs can be prepared as shown below.

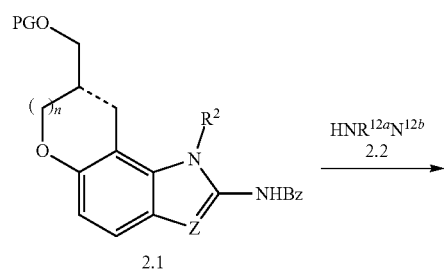

Compounds are represented in generic form, where PG is an alcohol protecting group and with other substituents as noted in compound descriptions elsewhere herein. A more specific example is set forth below.

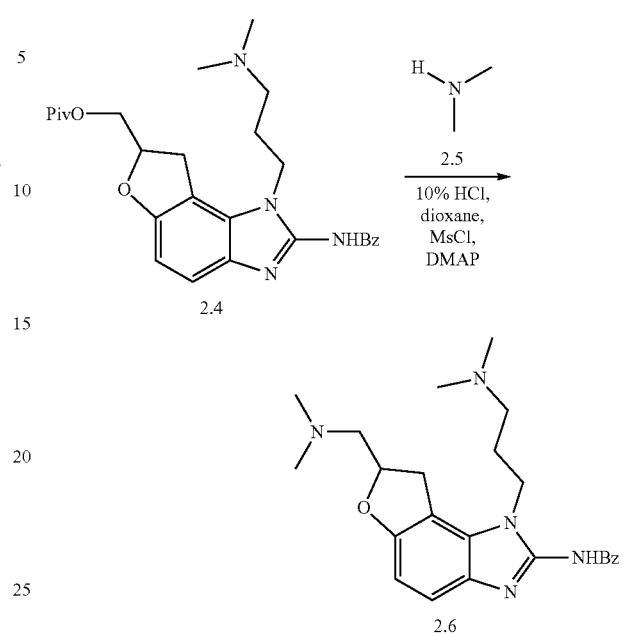

In one aspect, compounds of type 2.6, and similar compounds, can be prepared according to reaction Scheme 2B above. Thus, compounds of type 2.6 can be prepared by a substitution/deprotection reaction (simultaneously or sequentially) between an appropriate benzimidazole, e.g., 2.4 as shown above, and an appropriate amine, e.g., 2.5 as shown above. Appropriate amines are commercially available or prepared by methods known to one skilled in the art. The substitution reaction is carried out in the presence of an appropriate activating agent, e.g., 4-dimethylamino pyridine (DMAP), and an appropriate activated halide, e.g., methane sulfonyl chloride. The deprotection reaction is carried out in the presence of an appropriate deprotecting agent, e.g., 10% hydrochloric acid, in an appropriate solvent, e.g., dioxane. As can be appreciated by one skilled in the art, the above reaction provides an example of a generalized approach wherein compounds similar in structure to the specific reactants above (compounds similar to compounds of type 2.1 and 2.2), can be substituted in the reaction to provide substituted benzimidazole analogs similar to Formula 2.3.

3. Route III

In one aspect, substituted benzimidazole analogs can be prepared as shown below.

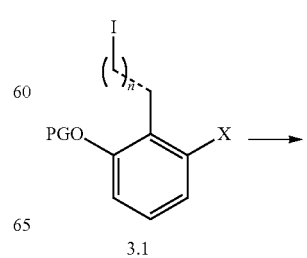

-continued

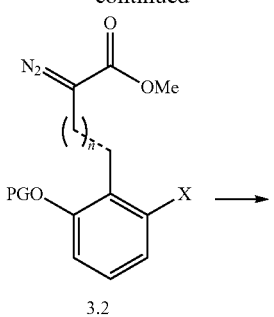
3.2

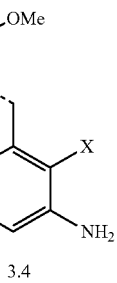
3.3     3.4

Compounds are represented in generic form, where X is a halogen, PG is an alcohol protecting group, and with other substituents as noted in compound descriptions elsewhere herein. A more specific example is set forth below.

SCHEME 3B

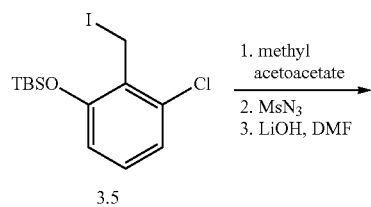
3.5

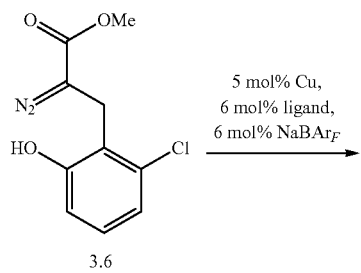
3.6

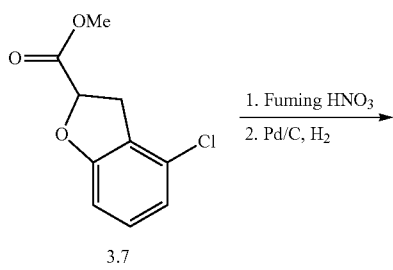
3.7

-continued

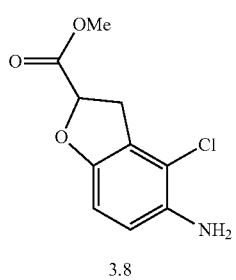
3.8

In one aspect, compounds of type 3.8, and similar compounds, can be prepared according to reaction Scheme 3B above. Thus, compounds of type 3.6 can be prepared by a diazo transfer and deprotection beginning from an appropriate halide, e.g., 3.5 as shown above. Appropriate halides are commercially available or prepared by methods known to one skilled in the art. The diazo transfer is carried out by converting the halide to a 0-ketoester, followed by transfer of the diazo moiety from mesyl azide. Addition of an appropriate deprotecting agent, e.g., lithium hydroxide in dimethylformamide, leads to the appropriate phenol, e.g., 3.6 as shown above. Compounds of type 3.7 can be prepared by cyclization of an appropriate azide, e.g., 3.6 as shown above. The cyclization is carried out in the presence of an appropriate metal, e.g., 5 mol % copper catalyst, and an appropriate ligand and an appropriate catalyst, e.g., sodium tetrakis[3,5-bis(trifluoromethyl)phenyl]borate as shown above. Compounds of type 3.8 can be prepared by nitration and reduction of an appropriate aryl halide, e.g., 3.7 as shown above. The nitration is carried out in the presence of an appropriate nitrating agent, e.g., fuming nitric acid, followed by reduction using an appropriate reducing agent, e.g., hydrogen gas, and an appropriate catalyst, e.g., palladium on carbon. As can be appreciated by one skilled in the art, the above reaction provides an example of a generalized approach wherein compounds similar in structure to the specific reactants above (compounds similar to compounds of type 3.1, 3.2, and 3.3), can be substituted in the reaction to provide substituted benzimidazole analogs similar to Formula 3.4.

4. Route IV

In one aspect, substituted benzimidazole analogs can be prepared as shown below.

SCHEME 4A

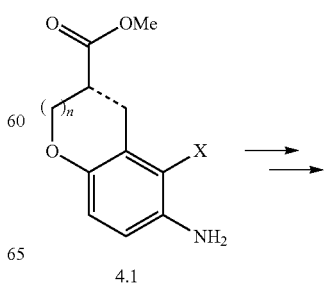
4.1

5. Route V

In one aspect, substituted benzimidazole analogs can be prepared as shown below.

SCHEME 5A

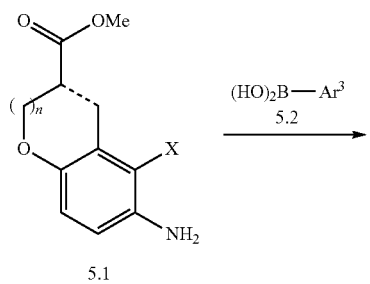

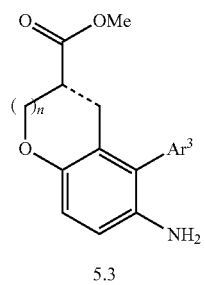

Compounds are represented in generic form, with substituents as noted in compound descriptions elsewhere herein. A more specific example is set forth below.

SCHEME 5B

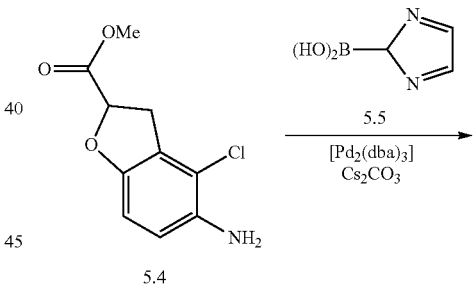

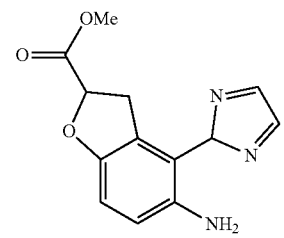

In one aspect, compounds of type 5.6, and similar compounds, can be prepared according to reaction Scheme 5B above. Thus, compounds of type 5.6 can be prepared by a substitution reaction of an appropriate aryl halide, e.g., 5.4 as shown above, and an appropriate boronic acid, e.g., 5.5 as shown above. Appropriate boronic acids are commercially available or prepared by methods known to one skilled in the art. The substitution reaction is carried out in the presence of an appropriate catalyst, e.g., tris(dibenzylideneacetone)di-

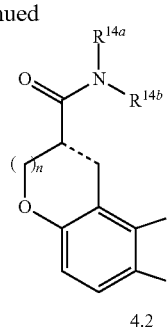

Compounds are represented in generic form, where X is a halogen and with other substituents as noted in compound descriptions elsewhere herein. A more specific example is set forth below.

SCHEME 4B

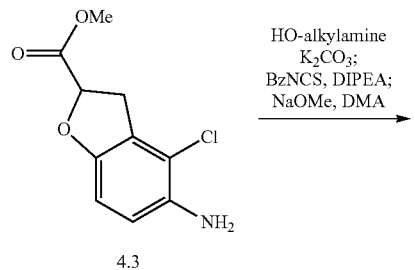

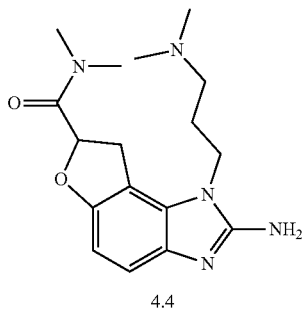

In one aspect, compounds of type 4.4, and similar compounds, can be prepared according to reaction Scheme 4B above. Thus, compounds of type 4.4 can be prepared from an appropriate aryl halide, e.g., 4.3 as shown above. Appropriate halides are commercially available or prepared by methods known to one skilled in the art. For example, a substitution reaction between the halide and an appropriate amine, e.g., a hydroxyalkylamine, in the presence of an appropriate base, e.g., potassium carbonate, results in the corresponding aryl amine. Next, a cyclization reaction is carried out using an appropriate thiocyanate, e.g., benzyl thiocyanate, and an appropriate base, e.g., diisopropylethylamine, thereby converting the aryl amine to a benzimidazole analog. Finally, an amidation reaction is carried out in the presence of an appropriate amine, e.g., dimethylamine, in the presence of an appropriate base, e.g., sodium methoxide. As can be appreciated by one skilled in the art, the above reaction provides an example of a generalized approach wherein compounds similar in structure to the specific reactants above (compounds similar to compounds of type 4.1 and 4.2), can be substituted in the reaction to provide substituted benzimidazole analogs similar to Formula 4.3.

palladium (0), and an appropriate base, e.g., cesium carbonate. As can be appreciated by one skilled in the art, the above reaction provides an example of a generalized approach wherein compounds similar in structure to the specific reactants above (compounds similar to compounds of type 5.1 and 5.2), can be substituted in the reaction to provide substituted benzimidazole analogs similar to Formula 5.3.

6. Additional Routes to Access Benzimidazole Analogs

Additional exemplary routes to access the disclosed benzimidazole analogs are shown in Scheme 6A and Scheme 6B below.

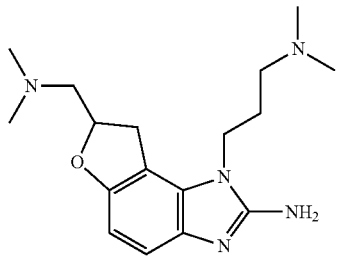
-continued

SCHEME 6A

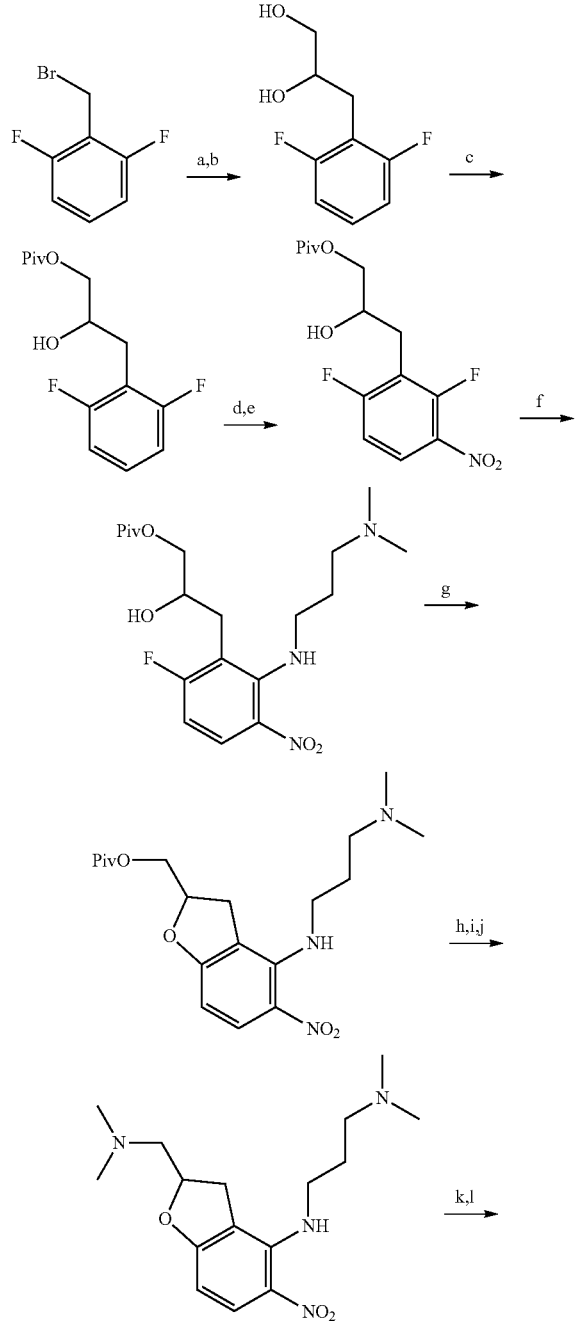

SCHEME 6B

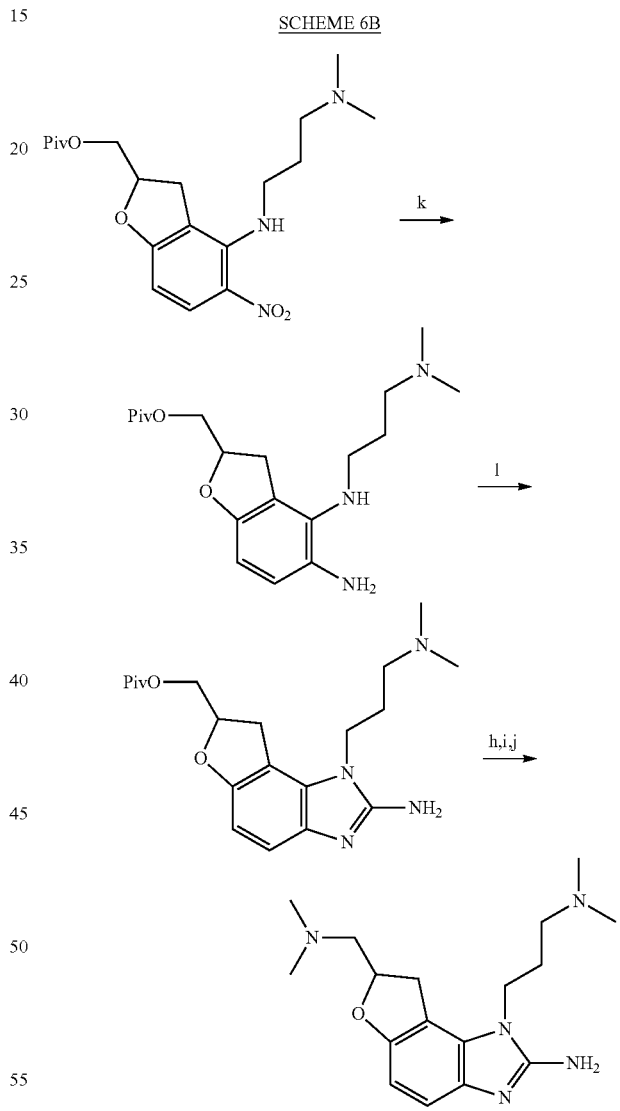

Exemplary Reagents & Conditions. (a) Vinyl magnesium bromide, CuI, 2,2'-dipyridyl (b) $OsO_4$, NMO (c) Pivaloyl chloride, $CH_2Cl_2$, $Et_3N$ (d) Acetyl chloride, $CH_2Cl_2$, 2,4,6-collidine (e) Fuming $HNO_3$, 0° C., 30 min. (f) 3-Dimethyl-amino-propylamine, $CH_2Cl_2$, $CaCO_3$, rt, 16 h (g) dry DMSO, MeOH, $K_2CO_3$, 50° C., 4 h (h) 10% HCl, dioxane, reflux, 8 h (i) $CH_3SO_2Cl$, $Et_3N$, DMAP, $CH_2Cl_2$ (j) 40% $Me_2NH/H_2O$, DMF, 40° C. (k) Pd/C, $H_2$ balloon, MeOH (l) CNBr, $CH_3CN$.

E. Methods of Using the Compounds

The compounds and pharmaceutical compositions of the invention are useful in treating or controlling disorders associated with hepatitis viral translation and/or RNA viral translation. Examples of disorders for which the compounds and compositions can be useful in treating, include, but are not limited to, hepatitis (e.g., hepatitis C), RNA virus infections (e.g., Zika virus, dengue virus, Powassan virus, Chikungunya virus, Enterovirus, respiratory syntactical virus (RSV), Rift Valley fever, Influenza virus, Tacaribe virus, Mayaro virus, West Nile virus, yellow fever virus, and coronavirus), and disorders of uncontrolled cellular proliferation (e.g., cancer).

To treat or control the disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a disorder, such as hepatitis (e.g., hepatitis C), RNA virus infections (e.g., Zika virus, dengue virus, Powassan virus, Chikungunya virus, Enterovirus, respiratory syntactical virus (RSV), Rift Valley fever, Influenza virus, Tacaribe virus, Mayaro virus, West Nile virus, yellow fever virus, and coronavirus), and/or disorders of uncontrolled cellular proliferation (e.g., cancer).

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a disorder, such as hepatitis (e.g., hepatitis C), RNA virus infections (e.g., Zika virus, dengue virus, Powassan virus, Chikungunya virus, Enterovirus, respiratory syntactical virus (RSV), Rift Valley fever, Influenza virus, Tacaribe virus, Mayaro virus, West Nile virus, yellow fever virus, and coronavirus), and/or disorders of uncontrolled cellular proliferation (e.g., cancer).

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

1. Treatment Methods

The compounds disclosed herein are useful for treating or controlling hepatitis (e.g., hepatitis C), RNA virus infections (e.g., Zika virus, dengue virus, Powassan virus, Chikungunya virus, Enterovirus, respiratory syntactical virus (RSV), Rift Valley fever, Influenza virus, Tacaribe virus, Mayaro virus, West Nile virus, yellow fever virus, and coronavirus), and/or disorders of uncontrolled cellular proliferation (e.g., cancer). Thus, provided is a method comprising administering a therapeutically effective amount of a composition comprising a disclosed compound to a subject. In a further aspect, the method can be a method for treating hepatitis. In a still further aspect, the method can be a method for treating a RNA virus infection. In yet a further aspect, the method can be a method for treating a disorder of uncontrolled cellular proliferation a. Treating Hepatitis In one aspect, disclosed are methods of treating hepatitis in a subject, the method comprising the step of administering to the subject a therapeutically effective amount of at least one disclosed compound, or a pharmaceutically acceptable salt thereof.

In one aspect, disclosed are methods of treating hepatitis in a subject, the method comprising the step of administering to the subject a therapeutically effective amount of at least one compound having a structure represented by a formula selected from:

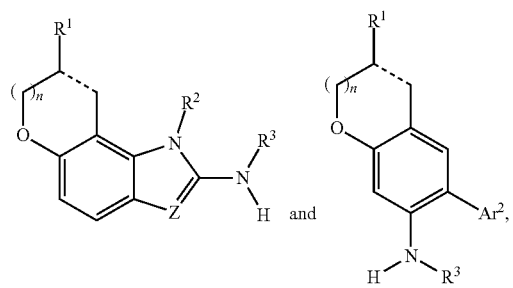

wherein ⁓ is a single or a double covalent bond; wherein n is 0 or 1; wherein Z, when present, is selected from N and $CR^{10}$; wherein $R^{10}$, when present, is selected from hydrogen and halogen; wherein $R^1$ is selected from —(C1-C4 alkyl)$OR^{11}$, —(C1-C4 alkyl)$NR^{12a}R^{12b}$, —$CO_2R^{13}$, and —C(O)$NR^{14a}R^{14b}$; wherein each of $R^{11}$, $R^{12a}$, and $R^{12b}$, when present, is independently selected from hydrogen, C1-C4 alkyl, —C(=NH)$NH_2$, —$CO_2$(C1-C4 alkyl), —(C1-C4 alkyl)$OR^{20}$, —(C1-C4 alkyl)$NR^{21a}R^{21b}$, —(C1-C4 alkyl)$Ar^1$, and $Ar^1$; wherein $Ar^1$, when present, is selected from aryl and heteroaryl and substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of $R^{13}$, $R^{14a}$, and $R^{14b}$, when present, is independently selected from hydrogen and C1-C4 alkyl; wherein $R^2$, when present, is selected from C1-C4 alkyl and —(C1-C4 alkyl)NR$^{15a}$R$^{15b}$; wherein each of R$^{15a}$ and R$^{15b}$, when present, is independently selected from hydrogen and C1-C4 alkyl; wherein R$^3$ is selected from hydrogen and C1-C4 alkyl; or wherein each of R$^2$, when present, and R$^3$ together comprise a 5- to 6-membered heterocycle substituted with a group selected from C1-C4 alkyl and —(C1-C4 alkyl)NR$^{16a}$R$^{16b}$; wherein each of R$^{16a}$ and R$^{11b}$, when present, is independently selected from hydrogen and C1-C4 alkyl; and wherein Ar$^2$ is a heteroaryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, provided that when the compound has a structure represented by a formula:

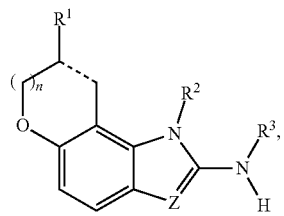

then either ⁓ is a double bond, Z is CR$^{10}$, or R$^2$ is C1-C4 alkyl, or a pharmaceutically acceptable salt thereof.

In one aspect, disclosed are methods of treating hepatitis in a subject, the method comprising the step of administering to the subject a therapeutically effective amount of at least one compound selected from:

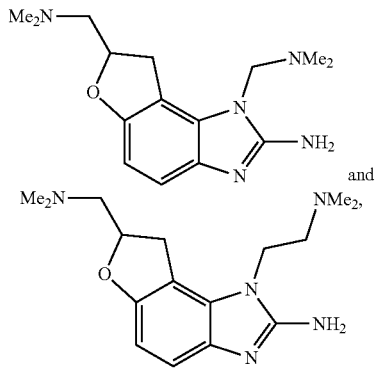

or a pharmaceutically acceptable salt thereof, and a pharmaceutically acceptable carrier.

Examples of hepatitis include, but are not limited to, hepatitis A, hepatitis B, and hepatitis C. In a further aspect, the hepatitis is hepatitis C.

In a further aspect, the subject has been diagnosed with a need for treatment of hepatitis prior to the administering step.

In a further aspect, the subject is a mammal. In a still further aspect, the mammal is a human.

In a further aspect, the method further comprises the step of identifying a subject in need of treatment of hepatitis.

In a further aspect, the hepatitis is associated with hepatitis viral translation.

In a further aspect, the hepatitis is selected from hepatitis A, hepatitis B, and hepatitis C. In yet a further aspect, the hepatitis is hepatitis C.

In a further aspect, the effective amount is a therapeutically effective amount. In a still further aspect, the effective amount is a prophylactically effective amount.

In a further aspect, the method further comprises the step of administering a therapeutically effective amount of at least one agent associated with the treatment of hepatitis. In a still further aspect, the at least one agent is selected from an antiviral agent (e.g., entecavir, tenofovir, lamivudine, adefovir, telbivudine, ribovarin) and an interferon (e.g., interferon alfa-2b, peginterferon).

In a further aspect, the at least one compound and the at least one agent are administered sequentially. In a still further aspect, the at least one compound and the at least one agent are administered simultaneously.

In a further aspect, the at least one compound and the at least one agent are co-formulated. In a still further aspect, the at least one compound and the at least one agent are co-packaged.

b. Treating a RNA Virus Infection

In one aspect, disclosed are methods of treating a RNA virus infection in a subject, the method comprising the step of administering to the subject a therapeutically effective amount of at least one disclosed compound, or a pharmaceutically acceptable salt thereof.

In one aspect, disclosed are methods for treating a RNA virus infection in a subject, the method comprising administering to the subject an effective amount of a compound having a structure represented by a formula selected from:

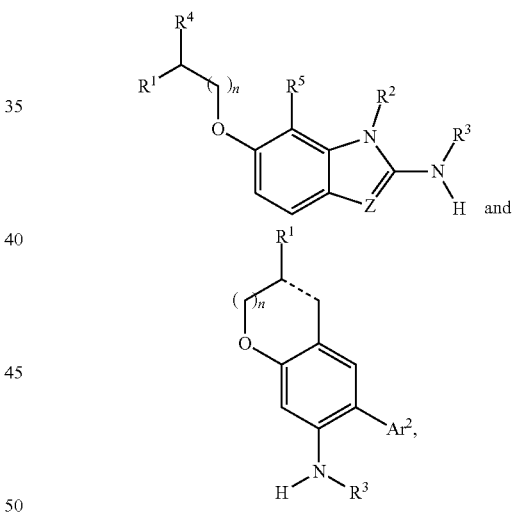

wherein ⁓ is a single or a double covalent bond; wherein n is 0 or 1; wherein Z, when present, is selected from N and CR$^{10}$; wherein R$^{10}$, when present, is selected from hydrogen and halogen; wherein R$^1$ is selected from —(C1-C4 alkyl)OR$^{11}$, —(C1-C4 alkyl)NR$^{12a}$R$^{12b}$, —CO$_2$R$^{13}$, and —C(O)NR$^{14a}$R$^{14b}$; wherein each of R$^{11}$, R$^{12a}$, and R$^{12b}$, when present, is independently selected from hydrogen, C1-C4 alkyl, —C(=NH)NH$_2$, —CO$_2$(C1-C4 alkyl), —(C1-C4 alkyl)OR$^{20}$, —(C1-C4 alkyl)NR$^{21a}$R$^{21b}$, —(C1-C4 alkyl)Ar$^1$, and Ar$^1$; wherein Ar$^1$, when present, is selected from aryl and heteroaryl and substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of R$^{13}$, R$^{14a}$, and R$^{14b}$, when present, is independently selected from hydrogen and C1-C4 alkyl; wherein $R^2$, when present, is selected from C1-C4 alkyl and —(C1-C4 alkyl)$NR^{15a}R^{15b}$; wherein each of $R^{15a}$ and $R^{15b}$, when present, is independently selected from hydrogen and C1-C4 alkyl; wherein $R^3$ is selected from hydrogen and C1-C4 alkyl; or wherein each of $R^2$, when present, and $R^3$ together comprise a 5- to 6-membered heterocycle substituted with a group selected from C1-C4 alkyl and —(C1-C4 alkyl)$NR^{16a}R^{16b}$; wherein each of $R^{16a}$ and $R^{16b}$, when present, is independently selected from hydrogen and C1-C4 alkyl; wherein each of $R^4$ and $R^5$ is hydrogen or together comprise a 5- to 6-membered heterocycle; and wherein $Ar^2$ is a heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, provided that when each of $R^4$ and $R^5$ is hydrogen, then R is —(C1-C4 alkyl)$OR^{11}$ or —(C1-C4 alkyl)$NR^{12a}R^{12b}$, or a pharmaceutically acceptable salt thereof.

Examples of RNA virus infections include, but are not limited to, Zika virus, dengue virus, Powassan virus, Chikungunya virus, Enterovirus, respiratory syntactical virus (RSV), Rift Valley fever, Influenza virus, Tacaribe virus, Mayaro virus, West Nile virus, yellow fever virus, and coronavirus.

In a further aspect, the subject has been diagnosed with a need for treatment of the RNA virus infection prior to the administering step.

In a further aspect, the subject is a mammal. In a still further aspect, the mammal is a human.

In a further aspect, the method further comprises the step of identifying a subject in need of treatment of the RNA virus infection.

In a further aspect, the effective amount destroys the RNA virus infection. In a still further aspect, the effective amount prevents replication of the RNA virus infection.

In a further aspect, the RNA virus infection is selected from Zika virus, dengue virus, Powassan virus, Chikungunya virus, Enterovirus, respiratory syntactical virus (RSV), Rift Valley fever, Influenza virus, Tacaribe virus, Mayaro virus, West Nile virus, yellow fever virus, and coronavirus. In yet a further aspect, the RNA virus infection is Zika virus.

In a further aspect, the RNA virus infection is coronavirus. Examples of coronavirus diseases include, but are not limited to, 229E (alpha coronavirus), NL63 (alpha coronavirus), OC43 (beta coronavirus), HKU1 (beta coronavirus), Middle East respiratory syndrome coronavirus (MERS-CoV), severe acute respiratory syndrome coronavirus (SARS-CoV), and coronavirus disease 2019 (COID-19). In a still further aspect, the RNA virus infection is severe acute respiratory syndrome coronavirus 2 (SARS-CoV-2).

In a further aspect, the effective amount is a therapeutically effective amount. In a still further aspect, the effective amount is a prophylactically effective amount.

In a further aspect, the method further comprises the step of administering a therapeutically effective amount of at least one agent associated with the treatment of a RNA virus infection. In a still further aspect, the at least one agent is selected from nucleoside analogs such as, for example, ribavirin, 7DMA, NITD008, 2'-deoxy-2'-fluoro nucleoside analogs (e.g., 2'-deoxy-2'-fluoro guanosine, 2'-deoxy-2'-fluoro cytidine), flavipiravir, lumicitabine, and GS-5734.

In a further aspect, the at least one compound and the at least one agent are administered sequentially. In a still further aspect, the at least one compound and the at least one agent are administered simultaneously.

In a further aspect, the at least one compound and the at least one agent are co-formulated. In a still further aspect, the at least one compound and the at least one agent are co-packaged.

c. Treating a Disorder of Uncontrolled Cellular Proliferation

In one aspect, disclosed are methods for treating a disorder of uncontrolled cellular proliferation in a subject, the method comprising the step of administering to the subject a therapeutically effective amount of at least one disclosed compound, or a pharmaceutically acceptable salt thereof.

In one aspect, disclosed are methods for treating a disorder of uncontrolled cellular proliferation in a subject, the method comprising administering to the subject an effective amount of a compound having a structure represented by a formula selected from:

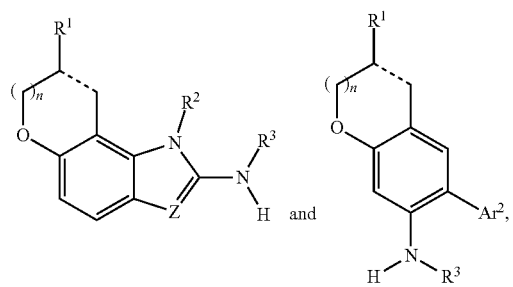

wherein ⸺ is a single or a double covalent bond; wherein n is 0 or 1; wherein Z, when present, is selected from N and $CR^{10}$; wherein $R^{10}$, when present, is selected from hydrogen and halogen; wherein $R^1$ is selected from —(C1-C4 alkyl)$OR^{11}$, —(C1-C4 alkyl)$NR^{12a}R^{12b}$, —$CO_2R^{13}$, and —C(O)$NR^{14a}R^{14b}$; wherein each of $R^{11}$, $R^{12a}$, and $R^{12b}$, when present, is independently selected from hydrogen, C1-C4 alkyl, —C(=NH)$NH_2$, —$CO_2$(C1-C4 alkyl), —(C1-C4 alkyl)$OR^{20}$, —(C1-C4 alkyl)$NR^{21a}R^{21b}$, —(C1-C4 alkyl)$Ar^1$, and $Ar^1$; wherein $Ar^1$, when present, is selected from aryl and heteroaryl and substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of $R^{13}$, $R^{14a}$, and $R^{14b}$, when present, is independently selected from hydrogen and C1-C4 alkyl; wherein $R^2$, when present, is selected from C1-C4 alkyl and —(C1-C4 alkyl)$NR^{15a}R^{15b}$; wherein each of $R^{15a}$ and $R^{15b}$, when present, is independently selected from hydrogen and C1-C4 alkyl; wherein $R^3$ is selected from hydrogen and C1-C4 alkyl; or wherein each of $R^2$, when present, and $R^3$ together comprise a 5- to 6-membered heterocycle substituted with a group selected from C1-C4 alkyl and —(C1-C4 alkyl)$NR^{16a}R^{16b}$; wherein each of $R^{16a}$ and $R^{16b}$, when present, is independently selected from hydrogen and C1-C4 alkyl; and wherein $Ar^2$ is a heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, or a pharmaceutically acceptable salt thereof.

Examples of disorders of uncontrolled cellular proliferation include, but are not limited to, cancers such as, for example, sarcomas, carcinomas, hematological cancers, solid tumors, breast cancer, cervical cancer, gastrointestinal cancer, colorectal cancer, brain cancer, skin cancers, prostate cancer, ovarian cancer, thyroid cancer, testicular cancer, pancreatic cancer, endometrial cancer, melanoma, glioma, medulloblastoma, leukemia, lymphoma, chronic myeloproliferative disorder, myelodysplastic syndrome, myeloproliferative neoplasm, and plasma cell neoplasm (myeloma).

In a further aspect, the subject has been diagnosed with a need for treatment of the disorder of uncontrolled cellular proliferation prior to the administering step.

In a further aspect, the subject is a mammal. In a still further aspect, the mammal is a human.

In a further aspect, the method further comprises the step of identifying a subject in need of treatment of the disorder of uncontrolled cellular proliferation.

In a further aspect, the disorder of uncontrolled cellular proliferation is associated with dysregulation of c-Myc signaling. In a still further aspect, the disorder of uncontrolled cellular proliferation is associated with activation and/or over-activation of c-Myc signaling.

In a further aspect, the disorder of uncontrolled cellular proliferation is a cancer. In yet a further aspect, the cancer is selected from a sarcoma, a carcinoma, a hematological cancer, a solid tumor, breast cancer, cervical cancer, gastrointestinal cancer, colorectal cancer, brain cancer, skin cancer, prostate cancer, ovarian cancer, thyroid cancer, testicular cancer, pancreatic cancer, endometrial cancer, melanoma, glioma, medulloblastoma, leukemia, lymphoma, chronic myeloproliferative disorder, myelodysplastic syndrome, myeloproliferative neoplasm, and plasma cell neoplasm (myeloma). In an even further aspect, the cancer is selected from a leukemia, colorectal cancer, pancreatic cancer, ovarian cancer, non-small cell lung carcinoma, and breast cancer. In a still further aspect, the cancer is a liver cancer. In yet a further aspect, the liver cancer is selected from hepatocellular carcinoma, cholangiocarcinoma, and biliary tract cancer. In an even further aspect, the liver cancer is a metastasis originated from another cancer.

In a further aspect, the effective amount is a therapeutically effective amount. In a still further aspect, the effective amount is a prophylactically effective amount.

In a further aspect, the method further comprises the step of administering a therapeutically effective amount of at least one agent associated with the treatment of a disorder of uncontrolled cellular proliferation. In a still further aspect, the at least one agent is a chemotherapeutic agent. In a still further aspect, the chemotherapeutic agent is selected from an alkylating agent, an antimetabolite agent, an antineoplastic antibiotic agent, a mitotic inhibitor agent, and a mTOR inhibitor agent.

In a further aspect, the antineoplastic antibiotic agent is selected from doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof.

In a further aspect, the antimetabolite agent is selected from gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof.

In a further aspect, the alkylating agent is selected from carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt thereof.

In a further aspect, the mitotic inhibitor agent is selected from irinotecan, topotecan, rubitecan, cabazitaxel, docetaxel, paclitaxel, etopside, vincristine, ixabepilone, vinorelbine, vinblastine, and teniposide, or a pharmaceutically acceptable salt thereof.

In a further aspect, the mTor inhibitor agent is selected from everolimus, siroliumus, sapanisertib, and temsirolimus, or a pharmaceutically acceptable salt, hydrate, solvate, or polymorph thereof.

In a further aspect, the at least one compound and the at least one agent are administered sequentially. In a still further aspect, the at least one compound and the at least one agent are administered simultaneously.

In a further aspect, the at least one compound and the at least one agent are co-formulated. In a still further aspect, the at least one compound and the at least one agent are co-packaged.

2. Methods of Modulating Hepatitis Viral Translation in a Subject

In one aspect, disclosed are methods of modulating hepatitis viral translation in a subject, the method comprising the step of administering to the subject an effective amount of at least one disclosed compound, or a pharmaceutically acceptable salt thereof.

In one aspect, disclosed are methods of modulating hepatitis viral translation in a subject, the method comprising the step of administering to the subject an effective amount of at least one compound having a structure represented by a formula selected from:

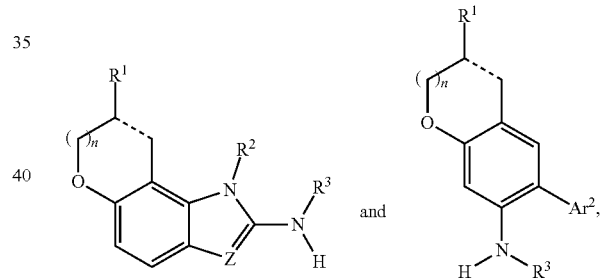

wherein ---- is a single or a double covalent bond; wherein n is 0 or 1; wherein Z, when present, is selected from N and $CR^{10}$; wherein $R^{10}$, when present, is selected from hydrogen and halogen; wherein $R^1$ is selected from —(C1-C4 alkyl) $OR^{11}$, —(C1-C4 alkyl)$NR^{12a}R^{12b}$, —$CO_2R^{13}$, and —C(O) $NR^{14a}R^{14b}$; wherein each of $R^{11}$, $R^{12a}$, and $R^{12b}$, when present, is independently selected from hydrogen, C1-C4 alkyl, —C(=NH)$NH_2$, —$CO_2$(C1-C4 alkyl), —(C1-C4 alkyl)$OR^{20}$, —(C1-C4 alkyl)$NR^{21a}R^{21b}$, —(C1-C4 alkyl) $Ar^1$, and $Ar^1$; wherein $Ar^1$, when present, is selected from aryl and heteroaryl and substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of $R^{13}$, $R^{14a}$, and $R^{14b}$, when present, is independently selected from hydrogen and C1-C4 alkyl; wherein $R^2$, when present, is selected from C1-C4 alkyl and —(C1-C4 alkyl)$NR^{15a}R^{15b}$; wherein each of $R^{15a}$ and $R^{15b}$, when present, is independently selected from hydrogen and C1-C4 alkyl; wherein $R^3$ is selected from hydrogen and C1-C4 alkyl; or wherein each of $R^2$, when present, and R³ together comprise a 5- to 6-membered heterocycle substituted with a group selected from C1-C4 alkyl and —(C1-C4 alkyl)NR$^{16a}$R$^{16b}$; wherein each of R$^{16a}$ and R$^{16b}$, when present, is independently selected from hydrogen and C1-C4 alkyl; and wherein Ar² is a heteroaryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, provided that when the compound has a structure represented by a formula:

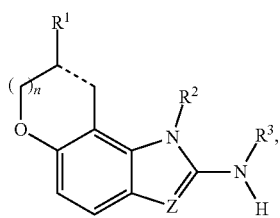

then either ⋯ is a double bond, Z is CR$^{10}$, or R² is C1-C4 alkyl, or a pharmaceutically acceptable salt thereof.

In one aspect, disclosed are methods of modulating hepatitis viral translation in a subject, the method comprising the step of administering to the subject an effective amount of at least one compound selected from:

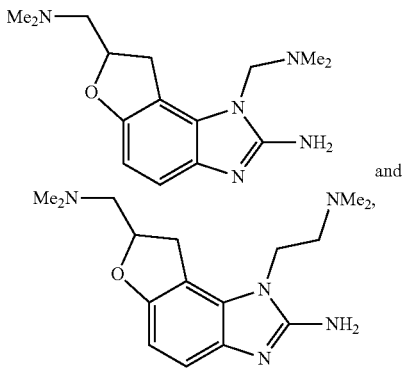

or a pharmaceutically acceptable salt thereof, and a pharmaceutically acceptable carrier.

In a further aspect, modulating is inhibiting.

In a further aspect, the compound exhibits inhibition of hepatitis viral translation. In a still further aspect, the compound exhibits a decrease in hepatitis viral translation.

In a further aspect, the compound exhibits inhibition of hepatitis viral translation with an IC$_{50}$ of less than about 30 μM. In a still further aspect, the compound exhibits inhibition of hepatitis viral translation with an IC$_{50}$ of less than about 25 μM. In yet a further aspect, the compound exhibits inhibition of hepatitis viral translation with an IC$_{50}$ of less than about 20 μM. In an even further aspect, the compound exhibits inhibition of hepatitis viral translation with an IC$_{50}$ of less than about 15 μM. In a still further aspect, the compound exhibits inhibition of hepatitis viral translation with an IC$_{50}$ of less than about 10 μM. In yet a further aspect, the compound exhibits inhibition of hepatitis viral translation with an IC$_{50}$ of less than about 5 μM. In an even further aspect, the compound exhibits inhibition of hepatitis viral translation with an IC$_{50}$ of less than about 1 μM. In a still further aspect, the compound exhibits inhibition of hepatitis viral translation with an IC$_{50}$ of less than about 0.5 μM.

In a further aspect, the subject is a mammal. In a still further aspect, the subject is a human.

In a further aspect, the subject has been diagnosed with a need for treatment of hepatitis prior to the administering step. In a still further aspect, the method further comprises the step of identifying a subject in need of treatment of hepatitis.

In a further aspect, the subject has been diagnosed with a need for treatment of a disorder associated with hepatitis viral translation prior to the administering step. In a still further aspect, the method further comprises the step of identifying a subject in need of treatment of a disorder associated with hepatitis viral translation. In yet a further aspect, the disorder associated with hepatitis viral translation is hepatitis (e.g., hepatitis C).

In a further aspect, the subject has been diagnosed with a need for modifying hepatitis viral translation prior to the administering step. In a still further aspect, the subject has been diagnosed with a need for inhibiting hepatitis viral translation prior to the administering step.

3. Methods of Modulating Hepatitis Viral Translation in at Least One Cell

In one aspect, disclosed are methods for modulating hepatitis viral translation in at least one cell, the method comprising the step of contacting the at least one cell with an effective amount of at least one disclosed compound, or a pharmaceutically acceptable salt thereof.

In one aspect, disclosed are methods of modulating hepatitis viral translation in at least one cell, the method comprising the step of contacting the at least one cell with an effective amount of at least one compound having a structure represented by a formula selected from:

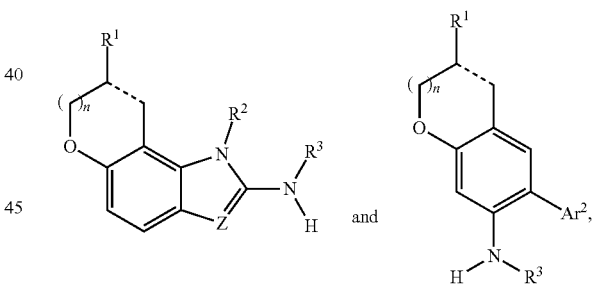

wherein ⋯ is a single or a double covalent bond; wherein n is 0 or 1; wherein Z, when present, is selected from N and CR$^{10}$; wherein R$^{10}$, when present, is selected from hydrogen and halogen; wherein R¹ is selected from —(C1-C4 alkyl)OR$^{11}$, —(C1-C4 alkyl)NR$^{12a}$R$^{12b}$, —CO$_2$R$^{13}$, and —C(O)NR$^{14a}$R$^{14b}$; wherein each of R$^{11}$, R$^{12a}$, and R$^{12b}$, when present, is independently selected from hydrogen, C1-C4 alkyl, —C(=NH)NH$_2$, —CO$_2$(C1-C4 alkyl), —(C1-C4 alkyl)OR$^{20}$, —(C1-C4 alkyl)NR$^{21a}$R$^{21b}$, —(C1-C4 alkyl)Ar¹, and Ar¹; wherein Ar¹, when present, is selected from aryl and heteroaryl and substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of R$^{13}$, R$^{14a}$, and R$^{14b}$, when present, is independently selected from hydrogen and C1-C4 alkyl; wherein R², when present, is selected from C1-C4 alkyl and —(C1-C4 alkyl)NR$^{15a}$R$^{15b}$; wherein each of R$^{15a}$ and R$^{15b}$, when present, is independently selected from hydrogen and C1-C4 alkyl; wherein R$^3$ is selected from hydrogen and C1-C4 alkyl; or wherein each of R$^2$, when present, and R$^3$ together comprise a 5- to 6-membered heterocycle substituted with a group selected from C1-C4 alkyl and —(C1-C4 alkyl)NR$^{16a}$R$^{16b}$; wherein each of R$^{16a}$ and R$^{16b}$, when present, is independently selected from hydrogen and C1-C4 alkyl; and wherein Ar$^2$ is a heteroaryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, provided that when the compound has a structure represented by a formula:

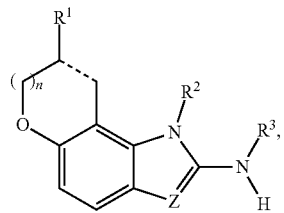

then either $\mathrm{--}$ is a double bond, Z is CR$^{10}$, or R$^2$ is C1-C4 alkyl, or a pharmaceutically acceptable salt thereof.

In one aspect, disclosed are methods of modulating hepatitis viral translation in at least one cell, the method comprising the step of contacting the at least one cell with an effective amount of at least one compound selected from:

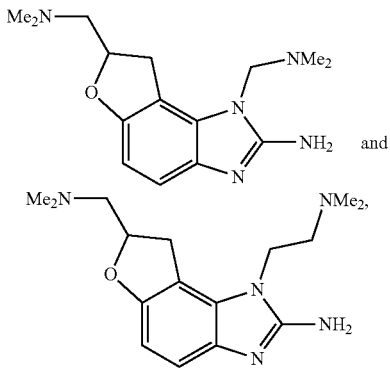

or a pharmaceutically acceptable salt thereof, and a pharmaceutically acceptable carrier.

In a further aspect, modulating is inhibiting.

In a further aspect, the cell is mammalian. In a still further aspect, the cell is human. In yet a further aspect, the cell has been isolated from a mammal prior to the contacting step.

In a further aspect, contacting is via administration to a subject.

In a further aspect, the subject has been diagnosed with a need for modification of hepatitis viral translation prior to the administering step. In a still further aspect, the subject has been diagnosed with a need for treatment of a disorder associated with hepatitis viral translation (e.g., hepatitis such as, for example, hepatitis C).

4. Methods of Modulating Translation of a RNA Virus in a Subject

In one aspect, disclosed are methods of modulating translation of a RNA virus in a subject, the method comprising the step of administering to the subject an effective amount of at least one disclosed compound, or a pharmaceutically acceptable salt thereof.

In one aspect, disclosed are methods of methods for modulating translation of a RNA virus in a subject, the method comprising administering to the subject an effective amount of a compound having a structure represented by a formula selected from:

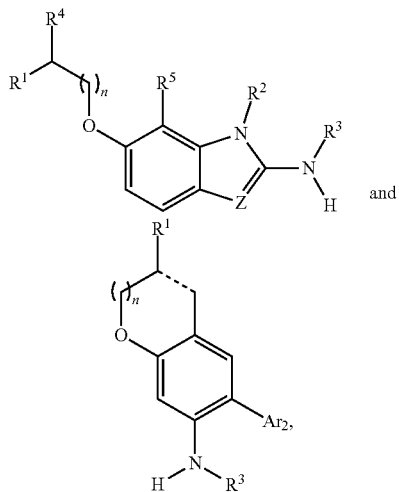

wherein $\mathrm{--}$ is a single or a double covalent bond; wherein n is 0 or 1; wherein Z, when present, is selected from N and CR$^{10}$; wherein R$^{10}$, when present, is selected from hydrogen and halogen; wherein R$^1$ is selected from —(C1-C4 alkyl)OR$^{11}$, —(C1-C4 alkyl)NR$^{12a}$R$^{12b}$, —CO$_2$R$^{13}$, and —C(O)NR$^{14a}$R$^{14b}$; wherein each of R$^{11}$, R$^{12a}$, and R$^{12b}$, when present, is independently selected from hydrogen, C1-C4 alkyl, —C(=NH)NH$_2$, —CO$_2$(C1-C4 alkyl), —(C1-C4 alkyl)OR$^{20}$, —(C1-C4 alkyl)NR$^{21a}$R$^{21b}$, —(C1-C4 alkyl)Ar$^1$, and Ar$^1$; wherein Ar$^1$, when present, is selected from aryl and heteroaryl and substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of R$^{13}$, R$^{14a}$, and R$^{14b}$, when present, is independently selected from hydrogen and C1-C4 alkyl; wherein R$^2$, when present, is selected from C1-C4 alkyl and —(C1-C4 alkyl)NR$^{15a}$R$^{15b}$; wherein each of R$^{15a}$ and R$^{15b}$, when present, is independently selected from hydrogen and C1-C4 alkyl; wherein R$^3$ is selected from hydrogen and C1-C4 alkyl; or wherein each of R$^2$, when present, and R$^3$ together comprise a 5- to 6-membered heterocycle substituted with a group selected from C1-C4 alkyl and —(C1-C4 alkyl)NR$^{16a}$R$^{16b}$; wherein each of R$^{16a}$ and R$^{16b}$, when present, is independently selected from hydrogen and C1-C4 alkyl; wherein each of R$^4$ and R$^5$ is hydrogen or together comprise a 5- to 6-membered heterocycle; and wherein Ar$^2$ is a heteroaryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4) (C1-C4) dialkylamino, provided that when each of R$^4$ and R[5] is hydrogen, then R is —(C1-C4 alkyl)OR[11] or —(C1-C4 alkyl)NR[12a]R[12b], or a pharmaceutically acceptable salt thereof.

In a further aspect, modulating is inhibiting.

In a further aspect, the compound exhibits inhibition of translation of a RNA virus. In a still further aspect, the compound exhibits a decrease in translation of a RNA virus.

In a further aspect, the compound exhibits inhibition of translation of a RNA virus with an $IC_{50}$ of less than about 30 μM. In a still further aspect, the compound exhibits inhibition of translation of a RNA virus with an $IC_{50}$ of less than about 25 μM. In yet a further aspect, the compound exhibits inhibition of translation of a RNA virus with an $IC_{50}$ of less than about 20 μM. In an even further aspect, the compound exhibits inhibition of translation of a RNA virus with an $IC_{50}$ of less than about 15 μM. In a still further aspect, the compound exhibits inhibition of translation of a RNA virus with an $IC_{50}$ of less than about 10 μM. In yet a further aspect, the compound exhibits inhibition of translation of a RNA virus with an $IC_{50}$ of less than about 5 μM. In an even further aspect, the compound exhibits inhibition of translation of a RNA virus with an $IC_{50}$ of less than about 1 μM. In a still further aspect, the compound exhibits inhibition of translation of a RNA virus with an $IC_{50}$ of less than about 0.5 μM.

In a further aspect, the subject is a mammal. In a still further aspect, the subject is a human.

In a further aspect, the subject has been diagnosed with a need for treatment of a RNA virus prior to the administering step. In a still further aspect, the method further comprises the step of identifying a subject in need of treatment of a RNA virus.

In a further aspect, the subject has been diagnosed with a need for treatment of a disorder associated with translation of a RNA virus prior to the administering step. In a still further aspect, the method further comprises the step of identifying a subject in need of treatment of a disorder associated with translation of a RNA virus. In yet a further aspect, the disorder associated with translation of a RNA virus is a RNA virus.

In a further aspect, the subject has been diagnosed with a need for modifying translation of a RNA virus prior to the administering step. In a still further aspect, the subject has been diagnosed with a need for inhibiting translation of a RNA virus prior to the administering step.

In a further aspect, each of R[4] and R[5] is hydrogen. In a still further aspect, each of R[4] and R[5] together comprise a 5- to 6-membered heterocycle.

In a further aspect, the compound has a structure represented by a formula:

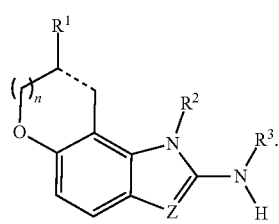

In a further aspect, the compound is selected from:

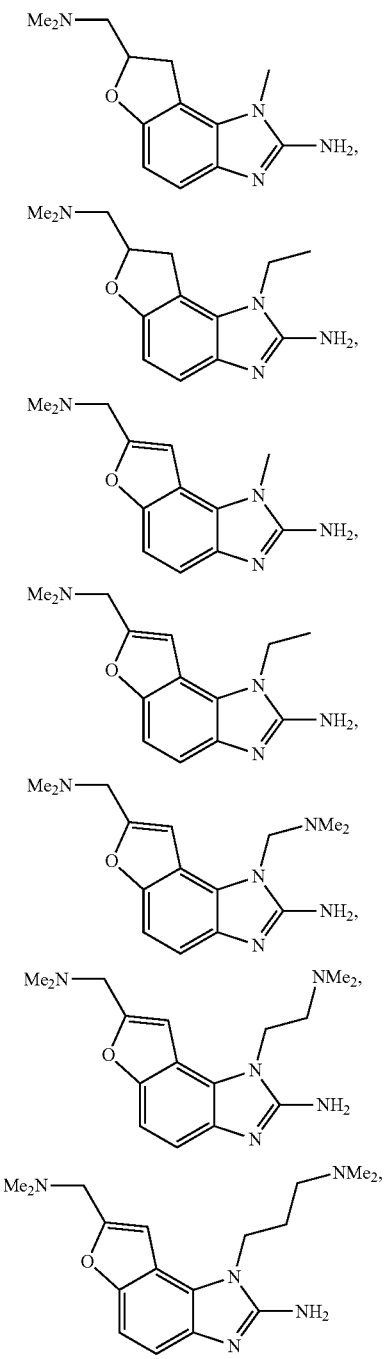

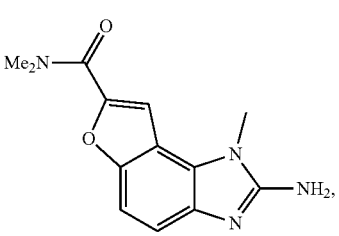

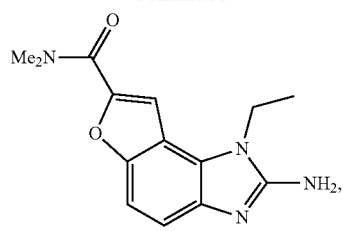
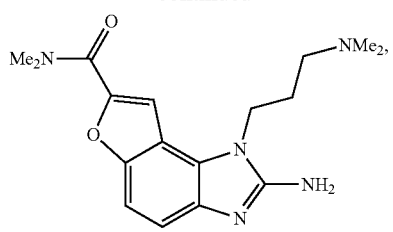
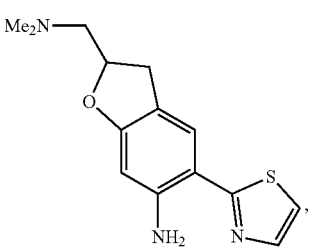

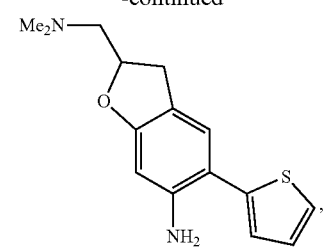
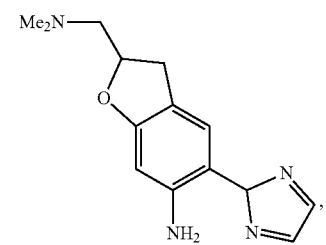
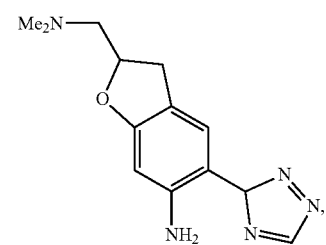
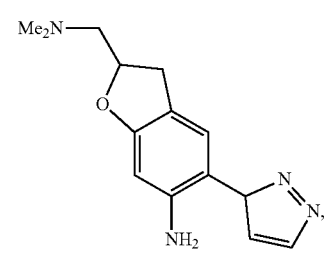
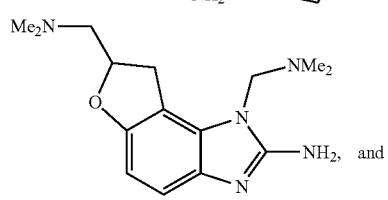
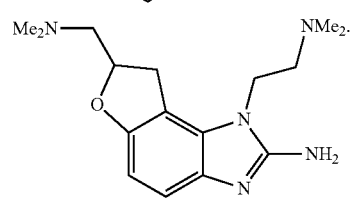

In a further aspect, the compound is selected from:

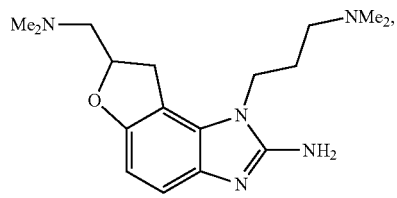

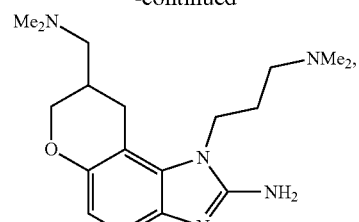
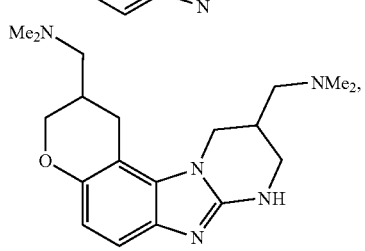
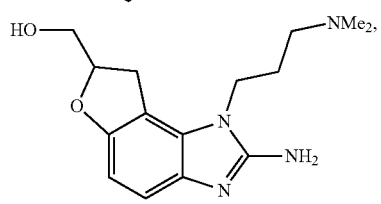
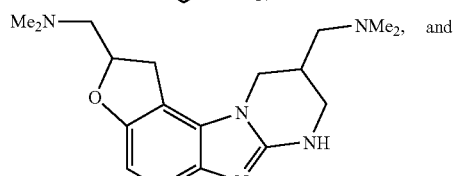
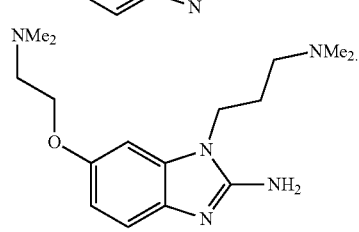

5. Methods of Modulating Translation of a RNA Virus in at Least One Cell

In one aspect, disclosed are methods for modulating translation of a RNA virus in at least one cell, the method comprising the step of contacting the at least one cell with an effective amount of at least one disclosed compound, or a pharmaceutically acceptable salt thereof.

In one aspect, disclosed are methods for modulating translation of a RNA virus in at least one cell, the method comprising contacting the cell with an effective amount of a compound having a structure represented by a formula selected from:

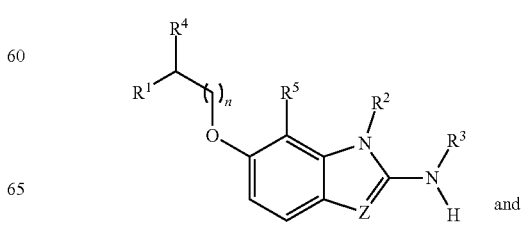

-continued

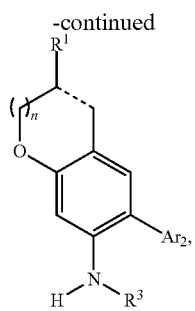

wherein ⌐ is a single or a double covalent bond; wherein n is 0 or 1; wherein Z, when present, is selected from N and $CR^{10}$; wherein $R^{10}$, when present, is selected from hydrogen and halogen; wherein $R^1$ is selected from —(C1-C4 alkyl) $OR^{11}$, —(C1-C4 alkyl)$NR^{12a}R^{12b}$, —$CO_2R^{13}$, and —C(O) $NR^{14a}R^{14b}$; wherein each of $R^{11}$, $R^{12a}$, and $R^{12b}$, when present, is independently selected from hydrogen, C1-C4 alkyl, —C(=NH)$NH_2$, —$CO_2$(C1-C4 alkyl), —(C1-C4 alkyl)$OR^{20}$, —(C1-C4 alkyl)$NR^{21a}R^{21b}$, —(C1-C4 alkyl) $Ar^1$, and $Ar^1$; wherein $Ar^1$, when present, is selected from aryl and heteroaryl and substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of $R^{13}$, $R^{14a}$, and $R^{14b}$, when present, is independently selected from hydrogen and C1-C4 alkyl; wherein $R^2$, when present, is selected from C1-C4 alkyl and —(C1-C4 alkyl)$NR^{15a}R^{15b}$; wherein each of $R^{15a}$ and $R^{15b}$, when present, is independently selected from hydrogen and C1-C4 alkyl; wherein $R^3$ is selected from hydrogen and C1-C4 alkyl; or wherein each of $R^2$, when present, and $R^3$ together comprise a 5- to 6-membered heterocycle substituted with a group selected from C1-C4 alkyl and —(C1-C4 alkyl)$NR^{16a}R^{16b}$; wherein each of $R^{16a}$ and $R^{16b}$, when present, is independently selected from hydrogen and C1-C4 alkyl; wherein each of $R^4$ and $R^5$ is hydrogen or together comprise a 5- to 6-membered heterocycle; and wherein $Ar^2$ is a heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4) (C1-C4) dialkylamino, provided that when each of $R^4$ and $R^5$ is hydrogen, then R is —(C1-C4 alkyl)$OR^{11}$ or —(C1-C4 alkyl)$NR^{12a}R^{12b}$, or a pharmaceutically acceptable salt thereof.

In a further aspect, modulating is inhibiting.

In a further aspect, the cell is mammalian. In a still further aspect, the cell is human. In yet a further aspect, the cell has been isolated from a mammal prior to the contacting step.

In a further aspect, contacting is via administration to a subject.

In a further aspect, the subject has been diagnosed with a need for modification of translation of a RNA virus prior to the administering step. In a still further aspect, the subject has been diagnosed with a need for treatment of a disorder associated with translation of a RNA virus.

In a further aspect, each of $R^4$ and $R^5$ is hydrogen. In a still further aspect, each of $R^4$ and $R^5$ together comprise a 5- to 6-membered heterocycle.

In a further aspect, the compound has a structure represented by a formula:

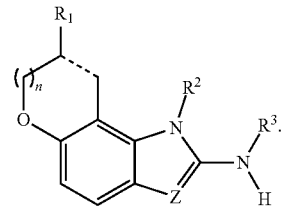

In a further aspect, the compound is selected from:

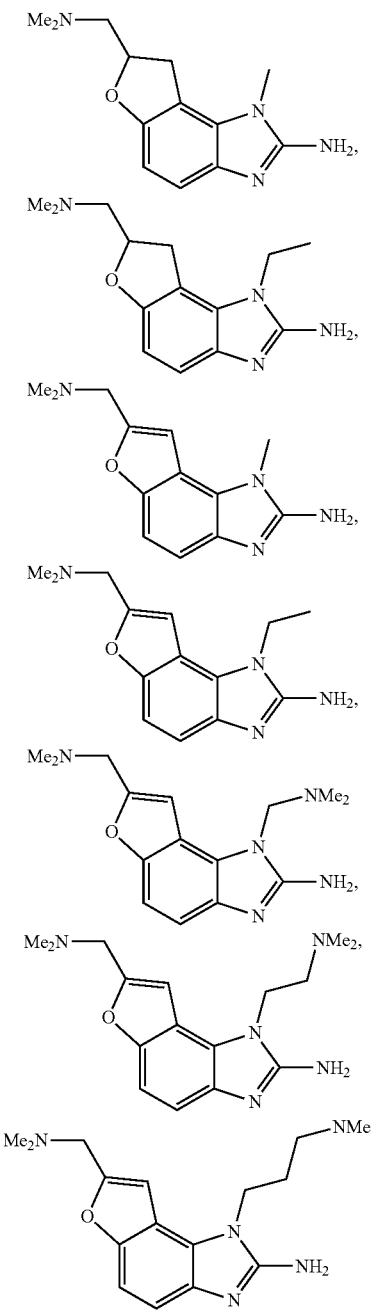

-continued
| 101 | 102 |
|---|---|
| 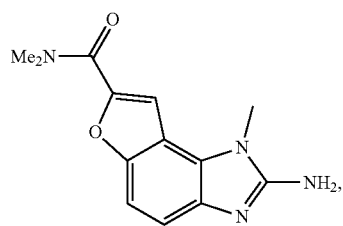 | 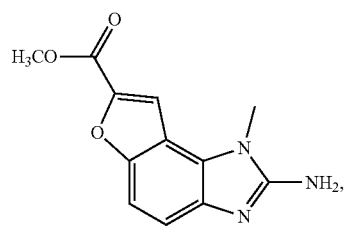 |
| 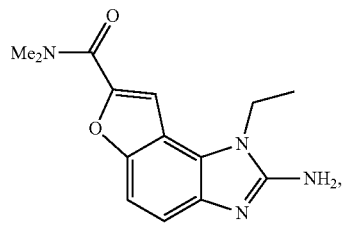 | 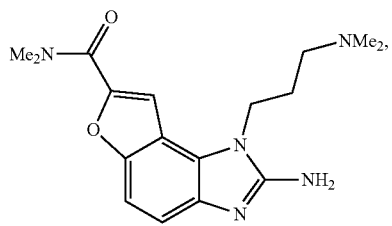 |
| 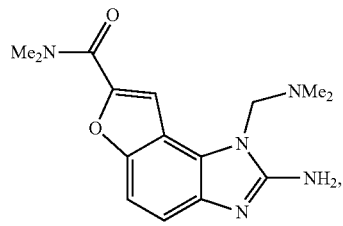 | 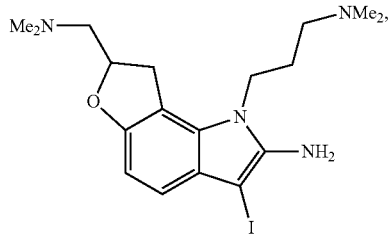 |
| 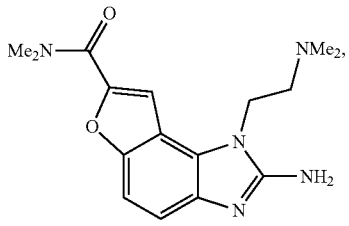 | 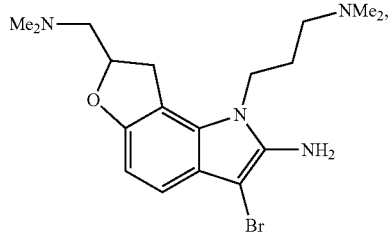 |
| 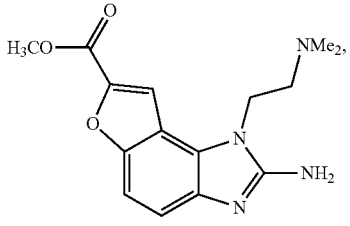 | 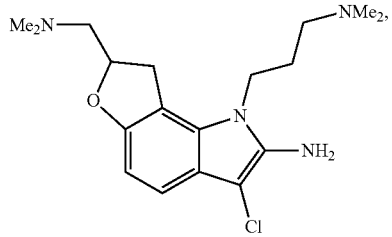 |
| 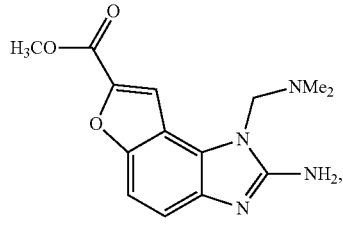 | 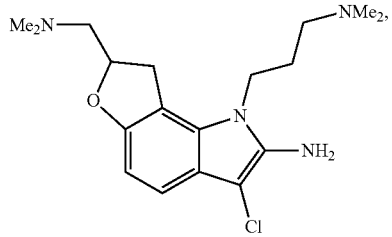 |
| 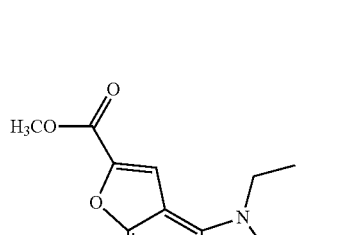 | 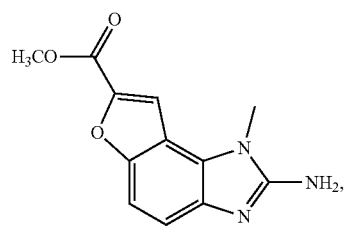 |

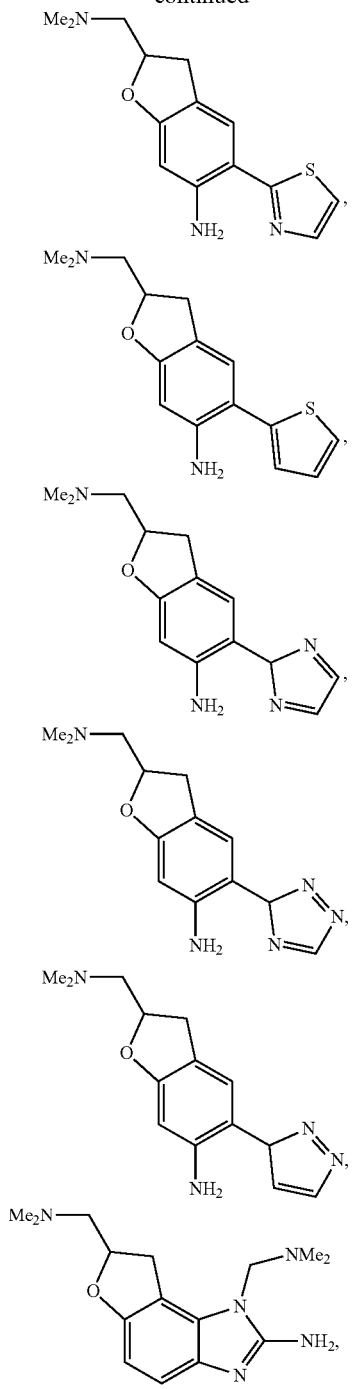

In a further aspect, the compound is selected from:

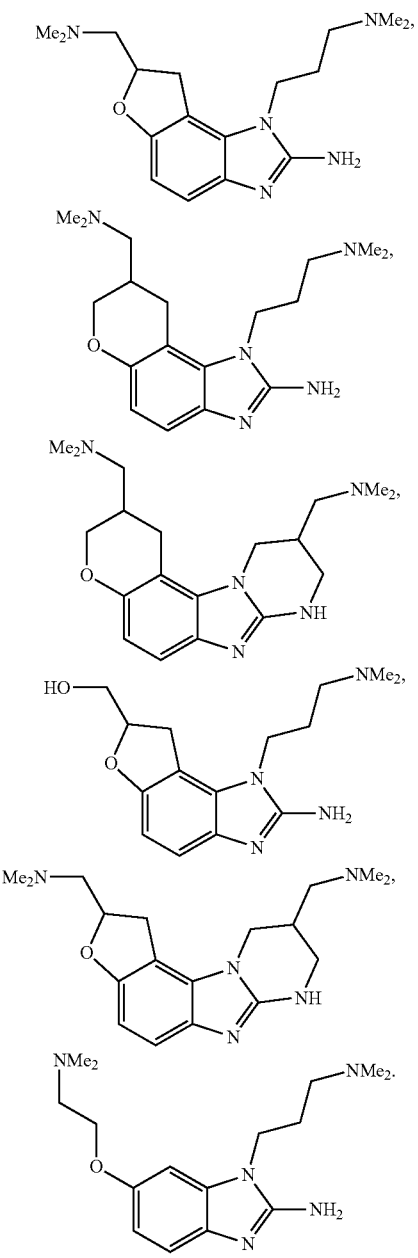

6. Use of Compounds

In one aspect, the invention relates to the use of a disclosed compound or a product of a disclosed method. In a further aspect, a use relates to the manufacture of a medicament for the treatment of hepatitis (e.g., hepatitis C), a RNA virus (e.g., Zika virus, dengue virus, Powassan virus, Chikungunya virus, Enterovirus, respiratory syntactical virus (RSV), Rift Valley fever, Influenza virus, Tacaribe virus, Mayaro virus, West Nile virus, yellow fever virus, and coronavirus), and/or a disorder of uncontrolled cellular proliferation (e.g., cancer) in a subject.

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of hepatitis in a subject. Also disclosed is the use of a compound for antagonism of hepatitis viral translation. In one aspect, the use is characterized in that the subject is a human. In one aspect, the use is characterized in that the hepatitis is hepatitis C.

In a further aspect, the use relates to the manufacture of a medicament for the treatment of hepatitis in a subject.

In a further aspect, the use relates to antagonism of hepatitis viral translation in a subject.

In various aspects, the use relates to a treatment of a RNA virus in a subject. Also disclosed is the use of a compound for antagonism of translation of a RNA viral infection. In one aspect, the use is characterized in that the subject is a human. In one aspect, the use is characterized in that the RNA virus is Zika virus. In one aspect, the use is characterized in that the RNA virus is a coronavirus such as, for example, severe acute respiratory syndrome coronavirus 2 (SARS-CoV-2).

In a further aspect, the use relates to the manufacture of a medicament for the treatment of a RNA virus in a subject.

In a further aspect, the use relates to antagonism of translation of a RNA viral infection in a subject.

In various aspects, the use relates to a treatment of a disorder of uncontrolled cellular proliferation in a subject. Also disclosed is the use of a compound for antagonism of c-Myc. In one aspect, the use is characterized in that the subject is a human. In one aspect, the use is characterized in that the disorder of uncontrolled cellular proliferation is a cancer.

In a further aspect, the use relates to the manufacture of a medicament for the treatment of a disorder of uncontrolled cellular proliferation in a subject.

In a further aspect, the use relates to antagonism of c-Myc in a subject.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of hepatitis (e.g., hepatitis C), a RNA virus (e.g., Zika virus, dengue virus, Powassan virus, Chikungunya virus, Enterovirus, respiratory syntactical virus (RSV), Rift Valley fever, Influenza virus, Tacaribe virus, Mayaro virus, West Nile virus, yellow fever virus, and coronavirus), and/or a disorder of uncontrolled cellular proliferation (e.g., cancer) in a mammal.

7. Manufacture of a Medicament

In one aspect, the invention relates to a method for the manufacture of a medicament for treating hepatitis (e.g., hepatitis C), a RNA virus (e.g., Zika virus, dengue virus, Powassan virus, Chikungunya virus, Enterovirus, respiratory syntactical virus (RSV), Rift Valley fever, Influenza virus, Tacaribe virus, Mayaro virus, West Nile virus, yellow fever virus, and coronavirus), and/or a disorder of uncontrolled cellular proliferation (e.g., cancer) in a subject, the method comprising combining a therapeutically effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in the treatment of hepatitis (e.g., hepatitis C), a RNA virus (e.g., Zika virus, dengue virus, Powassan virus, Chikungunya virus, Enterovirus, respiratory syntactical virus (RSV), Rift Valley fever, Influenza virus, Tacaribe virus, Mayaro virus, West Nile virus, yellow fever virus, and coronavirus), and/or a disorder of uncontrolled cellular proliferation (e.g., cancer). The dose administered to an animal, particularly a human, in the context of the present invention should be sufficient to affect a therapeutic response in the animal over a reasonable period. One skilled in the art will recognize that dosage will depend upon a variety of factors including the condition of the animal and the body weight of the animal.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose can also be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

8. Kits

In one aspect, disclosed are kits comprising a disclosed compound, and one or more of: (a) at least one agent known for the treatment of hepatitis; (b) instructions for administering the compound in connection with hepatitis; and (c) instructions for treating hepatitis.

Thus, in one aspect disclosed are kits comprising at least one compound having a structure represented by a formula selected from:

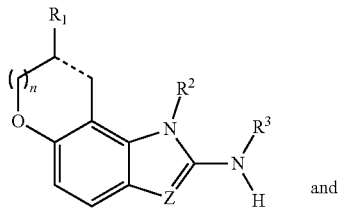

and

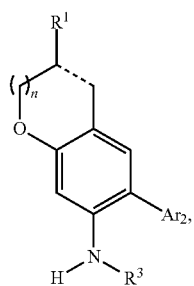

wherein ⌁ is a single or a double covalent bond; wherein n is 0 or 1; wherein Z, when present, is selected from N and CR$^{10}$; wherein R$^{10}$, when present, is selected from hydrogen and halogen; wherein R$^1$ is selected from —(C1-C4 alkyl) OR$^{11}$, —(C1-C4 alkyl)NR$^{12a}$R$^{12b}$, —CO$_2$R$^{13}$, and —C(O) NR$^{14a}$R$^{14b}$; wherein each of R$^{11}$, R$^{12a}$, and R$^{12b}$, when present, is independently selected from hydrogen, C1-C4 alkyl, —C(=NH)NH$_2$, —CO$_2$(C1-C4 alkyl), —(C1-C4 alkyl)OR$^{20}$, —(C1-C4 alkyl)NR$^{21a}$R$^{21b}$, —(C1-C4 alkyl) Ar$^1$, and Ar$^1$; wherein Ar$^1$, when present, is selected from aryl and heteroaryl and substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of R$^{13}$, R$^{14a}$, and R$^{14b}$, when present, is independently selected from hydrogen and C1-C4 alkyl; wherein R$^2$, when present, is selected from C1-C4 alkyl and —(C1-C4 alkyl)NR$^{15a}$R$^{15b}$; wherein each of R$^{15a}$ and R$^{151}$, when present, is independently selected from hydrogen and C1-C4 alkyl; wherein R$^3$ is selected from hydrogen and C1-C4 alkyl; or wherein each of R$^2$, when present, and R$^3$ together comprise a 5- to 6-membered heterocycle substituted with a group selected from C1-C4 alkyl and —(C1-C4 alkyl)NR$^{16a}$R$^{16b}$; wherein each of R$^{16a}$ and R$^{16b}$, when present, is independently selected from hydrogen and C1-C4 alkyl; and wherein Ar$^2$ is a heteroaryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, provided that when the compound has a structure represented by a formula:

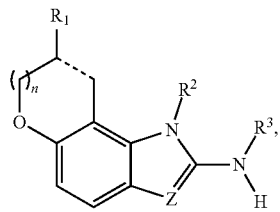

then either ⌁ is a double bond, Z is CR$^{10}$, or R$^2$ is C1-C4 alkyl, or a pharmaceutically acceptable salt thereof, and one or more of: (a) at least one agent known for the treatment of hepatitis; (b) instructions for administering the compound in connection with hepatitis; and (c) instructions for treating hepatitis.

In one aspect, disclosed are kits comprising at least one compound selected from:

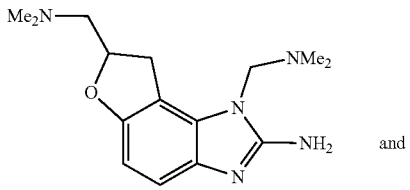

and

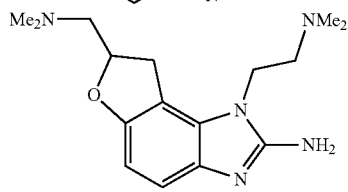

or a pharmaceutically acceptable salt thereof, and a pharmaceutically acceptable carrier, and one or more of: (a) at least one agent known for the treatment of hepatitis; (b) instructions for administering the compound in connection with hepatitis; and (c) instructions for treating hepatitis.

In one aspect, disclosed are kits comprising a compound having a structure represented by a formula selected from:

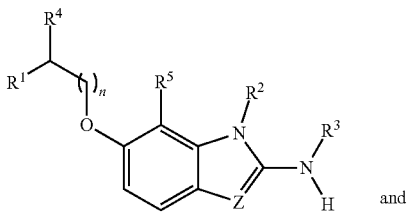

and

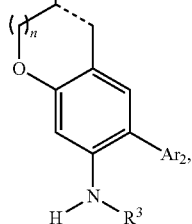

wherein ⌁ is a single or a double covalent bond; wherein n is 0 or 1; wherein Z, when present, is selected from N and CR$^{10}$; wherein R$^{10}$, when present, is selected from hydrogen and halogen; wherein R$^1$ is selected from —(C1-C4 alkyl)OR$^{11}$, —(C1-C4 alkyl)NR$^{12a}$R$^{12b}$, —CO$_2$R$^{13}$, and —C(O)NR$^{14a}$R$^{14b}$; wherein each of R$^{11}$, R$^{12a}$, and R$^{12b}$, when present, is independently selected from hydrogen, C1-C4 alkyl, —C(=NH)NH$_2$, —CO$_2$(C1-C4 alkyl), —(C1-C4 alkyl)OR$^{20}$, —(C1-C4 alkyl)NR$^{21a}$R$^{21b}$, —(C1-C4 alkyl)Ar$^1$, and Ar$^1$; wherein Ar$^1$, when present, is selected from aryl and heteroaryl and substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of R$^{13}$, R$^{14a}$, and R$^{14b}$, when present, is independently selected from hydrogen and C1-C4 alkyl; wherein R$^2$, when present, is selected from C1-C4 alkyl and —(C1-C4 alkyl)NR$^{15a}$R$^{15b}$; wherein each of R$^{15a}$ and R$^{15b}$, when present, is independently selected from hydrogen and C1-C4 alkyl; wherein R$^3$ is selected from hydrogen and C1-C4 alkyl; or wherein each of R$^2$, when present, and R$^3$ together comprise a 5- to 6-membered heterocycle substituted with a group selected from C1-C4 alkyl and —(C1-C4 alkyl)NR$^{16a}$R$^{16b}$; wherein each of R$^{16a}$ and R$^{16b}$, when present, is independently selected from hydrogen and C1-C4 alkyl; wherein each of R$^4$ and R$^5$ is hydrogen or together comprise a 5- to 6-membered heterocycle; and wherein Ar$^2$ is a heteroaryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, provided that when each of R$^4$ and R$^5$ is hydrogen, then R is —(C1-C4 alkyl)OR$^{11}$ or —(C1-C4 alkyl)NR$^{12a}$R$^{12b}$, or a pharmaceutically acceptable salt thereof, and one or more of: (a) at least one agent known for the treatment of a RNA virus infection; (b) instructions for administering the compound in connection with a RNA virus infection; (c) instructions for administering the compound in connection with reducing the risk of a RNA virus infection; and (d) instructions for treating a RNA virus infection.

In one aspect, disclosed are kits comprising a compound having a structure represented by a formula selected from:

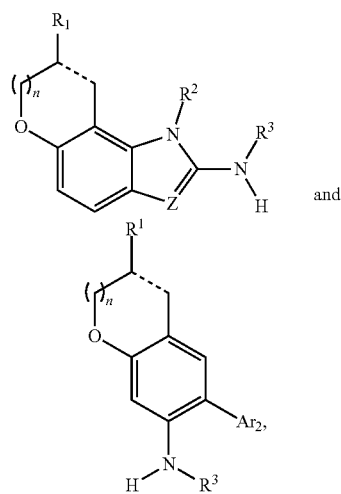

wherein ⌒ is a single or a double covalent bond; wherein n is 0 or 1; wherein Z, when present, is selected from N and CR$^{10}$; wherein R$^{10}$, when present, is selected from hydrogen and halogen; wherein R$^1$ is selected from —(C1-C4 alkyl)OR$^{11}$, —(C1-C4 alkyl)NR$^{12a}$R$^{12b}$, —CO$_2$R$^{13}$, and —C(O)NR$^{14a}$R$^{14b}$; wherein each of R$^{11}$, R$^{12a}$, and R$^{12b}$, when present, is independently selected from hydrogen, C1-C4 alkyl, —C(=NH)NH$_2$, —CO$_2$(C1-C4 alkyl), —(C1-C4 alkyl)OR$^{20}$, —(C1-C4 alkyl)NR$^{21a}$R$^{21b}$, —(C1-C4 alkyl)Ar$^1$, and Ar$^1$; wherein Ar$^1$, when present, is selected from aryl and heteroaryl and substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino; wherein each of R$^{13}$, R$^{14a}$, and R$^{14b}$, when present, is independently selected from hydrogen and C1-C4 alkyl; wherein R$^2$, when present, is selected from C1-C4 alkyl and —(C1-C4 alkyl)NR$^{15a}$R$^{15b}$; wherein each of R$^{15a}$ and R$^{15l}$, when present, is independently selected from hydrogen and C1-C4 alkyl; wherein R$^3$ is selected from hydrogen and C1-C4 alkyl; or wherein each of R$^2$, when present, and R$^3$ together comprise a 5- to 6-membered heterocycle substituted with a group selected from C1-C4 alkyl and —(C1-C4 alkyl)NR$^{16a}$R$^{16b}$; wherein each of R$^{16a}$ and R$^{16b}$, when present, is independently selected from hydrogen and C1-C4 alkyl; and wherein Ar$^2$ is a heteroaryl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, or a pharmaceutically acceptable salt thereof, and one or more of: (a) at least one agent associated with the treatment of a disorder of uncontrolled cellular proliferation; (b) instructions for administering the compound in connection with treating a disorder of uncontrolled cellular proliferation; and (c) instructions for treating a disorder of uncontrolled cellular proliferation.

In a further aspect, the hepatitis is selected from hepatitis A, hepatitis B, and hepatitis C. In a further aspect, the hepatitis is hepatitis C.

In a further aspect, the agent associated with the treatment of hepatitis is selected from an antiviral agent (e.g., entecavir, tenofovir, lamivudine, adefovir, telbivudine, ribovarin) and an interferon (e.g., interferon alfa-2b, peginterferon).

In a further aspect, the at least one compound and the at least one agent associated with the treatment of hepatitis are co-formulated. In a further aspect, the at least one compound and the at least one agent associated with the treatment of hepatitis are co-packaged.

In a further aspect, the RNA virus is selected from Zika virus, dengue virus, Powassan virus, Chikungunya virus, Enterovirus, respiratory syntactical virus (RSV), Rift Valley fever, Influenza virus, Tacaribe virus, Mayaro virus, West Nile virus, yellow fever virus, and coronavirus. In a further aspect, the RNA virus is Zika virus.

In a further aspect, the agent associated with the treatment of the RNA viral infection is selected from nucleoside analogs such as, for example, ribavirin, 7DMA, NITD008, 2'-deoxy-2'-fluoro nucleoside analogs (e.g., 2'-deoxy-2'-fluoro guanosine, 2'-deoxy-2'-fluoro cytidine), flavipiravir, lumicitabine, and GS-5734.

In a further aspect, the at least one compound and the at least one agent associated with the treatment of the RNA viral infection are co-formulated. In a further aspect, the at least one compound and the at least one agent associated with the treatment of the RNA viral infection are co-packaged.

In a further aspect, the disorder of controlled cellular proliferation is selected from a cancer. In yet a further aspect, the cancer is selected from a sarcoma, a carcinoma, a hematological cancer, a solid tumor, breast cancer, cervical cancer, gastrointestinal cancer, colorectal cancer, brain cancer, skin cancer, prostate cancer, ovarian cancer, thyroid cancer, testicular cancer, pancreatic cancer, endometrial cancer, melanoma, glioma, medulloblastoma, leukemia, lymphoma, chronic myeloproliferative disorder, myelodysplastic syndrome, myeloproliferative neoplasm, and plasma cell neoplasm (myeloma). In an even further aspect, the cancer is selected from a leukemia, colorectal cancer, pancreatic cancer, ovarian cancer, non-small cell lung carcinoma, and breast cancer. In a still further aspect, the cancer is a liver cancer. In yet a further aspect, the liver cancer is selected from hepatocellular carcinoma, cholangiocarcinoma, and biliary tract cancer. In an even further aspect, the liver cancer is a metastasis originated from another cancer.

In a further aspect, the agent associated with the treatment of the disorder of uncontrolled cellular proliferation is a chemotherapeutic agent. In a still further aspect, the chemotherapeutic agent is selected from an alkylating agent, an antimetabolite agent, an antineoplastic antibiotic agent, a mitotic inhibitor agent, and a mTOR inhibitor agent.

In a further aspect, the antineoplastic antibiotic agent is selected from doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof.

In a further aspect, the antimetabolite agent is selected from gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof.

In a further aspect, the alkylating agent is selected from carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt thereof.

In a further aspect, the mitotic inhibitor agent is selected from irinotecan, topotecan, rubitecan, cabazitaxel, docetaxel, paclitaxel, etopside, vincristine, ixabepilone, vinorelbine, vinblastine, and teniposide, or a pharmaceutically acceptable salt thereof.

In a further aspect, the mTor inhibitor agent is selected from everolimus, siroliumus, sapanisertib, and temsirolimus, or a pharmaceutically acceptable salt, hydrate, solvate, or polymorph thereof.

In a further aspect, the at least one compound and the at least one agent associated with the treatment of the disorder of uncontrolled cellular proliferation are co-formulated. In a further aspect, the at least one compound and the at least one agent associated with the treatment of the disorder of uncontrolled cellular proliferation are co-packaged.

In a further aspect, the compound and the agent are administered sequentially. In a still further aspect, the compound and the agent are administered simultaneously.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

F. Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Evaluation of Benzimidazole Analogs as Translation Inhibitors

Zika virus (ZIKV) has only recently become prominent as a major health hazard, but the virus belongs to the well-established Flaviviridae family of SSRNA (+) RNA viruses of which Dengue, yellow fever virus, and West Nile virus are prominent examples (Garcia et al. (2017) *Virology Journal* 14(1): 95). These flaviviruses have long been recognized as significant human pathogens.

The Dengue inhibitor Celgosivir progressed to the phase Ib trial stage after showing great promise at the preclinical stage (low nanomolar $IC_{50}$ in cell culture), but this compound was ineffective in vivo (Low et al. (2014) *The Lancet Infectious diseases* 14(8): 706-15). A promising nucleoside progdrug (Balapiravir) against Dengue virus (DENV) was found to be inefficiently activated in vivo, resulting in another highly touted, but ultimately disappointing trial (Chen et al. (2014) *Journal of Virology* 88(3): 1740-7). Here, it is hypothesized that ZIKV viral replication can be blocked in vivo with therapeutic effect using potent small molecule inhibitors of the host translational machinery (Wang et al. (2011) *Antimicrobial agents and chemotherapy* 55(9): 4072-80; Roth et al. (2017) *mBio* 8(1): e01250-16). Without wishing to be bound by theory, the activity demonstrated herein against numerous RNA viruses in addition to ZIKV demonstrates that this host-targeted strategy could have utility against emergent RNA viruses.

Substituted benzimidazole analogs were found to inhibit RNA virus replication with potencies in the 80-300 nM $EC_{50}$ range. Without wishing to be bound by theory, the antiviral activity may be dependent upon the single stereocenter provided by the fused dihydrofuran functional group. Two isomers, designated E1 and E2, were isolated by chiral HPLC after chemical synthesis of the racemic compound. The E1 and E2 isomers demonstrate an activity difference that ranges from 10-100 fold depending on the virus and the assay conditions, with the E2 isomer having the lower $EC_{50}$ in every evaluation (see FIG. 1).

As an example, Zika virus belongs to the family of Flaviviridae, along with Dengue, Yellow Fever Virus, and West Nile Virus. The lead compound E2 inhibits viral replication of all 4 viruses with $EC_{50}$ values ranging from 0.29-0.32 µM measured independently. With respect to the inhibition of a Puerto Rica strain of infectious Zika virus in Vero cells, specifically, an $EC_{50}$ of 0.08 µM for compound E2 was determined.

In addition, to further determine the effectiveness of the different anti-Zika virus compounds, newborn C57BL/6 mice will be infected with Zika virus (Sub-Q). Infected mice will be treated with three different novel anti-Zika virus compounds and followed for the development of runting, and central nervous system (CNS) pathology. Compounds will be administered IV at 5 mg/kg. Three weeks after the start of treatment, mice will be euthanized, perfused with PBS, and the CNS removed. Half the brain will be used for flow cytometry to determine the extent of infiltrating immune cells as well as activated microglia via immunophenotyping. The other half of the brain will be fixed in 4% buffered paraformaldehyde (PFA) overnight. Tissues will be processed for paraffin embedding, sectioned, and stained. Alternatively, brains can also be processed for frozen sections. Immunohistochemistry will be performed to identify cells types and changes in the CNS such as hydrocephalus. Groups of 7-10 mice will be used.

a. Comparison of Biocryst BCX4430 Antiviral Activity to ISIS-11 (E2/E1)

The E2 Isomer is 10-100 fold more potent than the polymerase inhibitor BCX4430 against a diverse sampling of therapeutically relevant viruses (see FIG. 1). BCX4430 has been promoted as a "broad-spectrum" antiviral (see Warren et al. (2014) *Nature* 508: 402-405. "Protection against filovirus diseases by a novel broad-spectrum nucleoside analogue BCX4430"); however, E2 is active against a broader range of pathogens and is significantly more potent against Zika, Dengue, Rift Valley Fever Virus (RVFV), and Powassan than BCX4430. For example, the activity is 92-fold greater against RVFV with an $EC_{50}$ of 0.45 µM for E2. The reported $EC_{50}$ value of BCX4430 of 41.6 µM against RVFV is a non-therapeutic potency level.

In addition, a 2017 publication regarding the use of BCX4430 in vivo against Zika, 150-300 mg/kg were used in a mouse model. If E2 was scaled down according to the relative potency shown in the Tables below (i.e., 80-fold), this same level of efficacy could be achieved at only 3.75 mg/kg. This is a much more reasonable dose, and such an IV dose would provide estimated plasma concentrations in the effective range for E2.

Thus, without wishing to be bound by theory, the advantages of using E2 as a therapeutic to target RNA viruses include, but are not limited to, much broader effectiveness, potentially including emerging viruses and druf-resistant mutants, and much higher potency compared to other "broad-spectrum" antivirals currently under development.

b. Evaluation of the Mechanism of Action of Benzimidazole Analogs

Flavivirus mRNA translation must outcompete the translation of endogenous mRNAs that utilize the same translation machinery. This endogenous mammalian translation process includes ribosomes, translation initiation factors, and translation elongation factors. Zika virus mRNAs, for example, are capped and are thought to engage the mRNA translation machinery in a similar fashion to the majority of mRNAs in a mammalian cell. Zika virus mRNA initiation codons are in a non-optimal sequence context (Eva Harris laboratory publications on Dengue virus, and sequence comparisons of Zika/Dengue), further putting the infecting flavivirus at an apparent competitive disadvantage. However, mRNAs from Flaviviruses such as Zika are effectively translated; therefore, these viral mRNAs must engage the host (e.g., human) translational initiation machinery through novel processes.

Here, it was observed that the E2 RNA virus inhibitor binds with very high affinity to the human initiator tRNA (approximately 1 µM $K_D$ in preliminary biochemical assays; FIG. 2). This binding selectively inhibits Zika virus translation, and this target binding inhibits the translation of many RNA viruses that must, by inference, be using a host translational process that facilitates viral mRNA translation. The activity against Zika has been confirmed with a sub-genomic replicon construct.

Referring to FIG. 2, the representative structural model was derived from NMR chemical shift perturbation data. The arrow shows the chiral center—the stereochemical bias for binding and for antiviral activity is profound. In vivo plasma PK measurements (detailed below) indicate similar PK for the two molecules; however, the in vitro activity measurements reflect the stereospecific engagement with the RNA target (also detailed below).

In addition, ZIKV translation initiation could be evaluated using rabbit reticulocyte lysate translation reporter constructs. The fundamental biochemical mechanism is predicated on selective inhibitor of flavivirus translation. Thus, this mechanism could be assayed using a monocistronic translational reporter engineered with the ZIKV 5'-UTR instead of the HCV 5'-UTR that was previously validated (Filbin and Kieft (2011) *RNA* 17: 1258-73). As detailed herein, the initial results show the remarkable sensitivity of this system to inhibition of E2 over E1. Such an assay would further validate the tRNA target.

In sum, the E2 stereoisomer of Isis-11 is a potent pan-viral inhibitor. The mechanism of action is inhibition of viral translation by binding to the ubiquitous initiator tRNA. The tRNA binding selectively inhibits viral mRNA translation initiation while sparing the initiation of most cellular mRNAs.

c. In Vitro Activity Measurements

Figure 3:
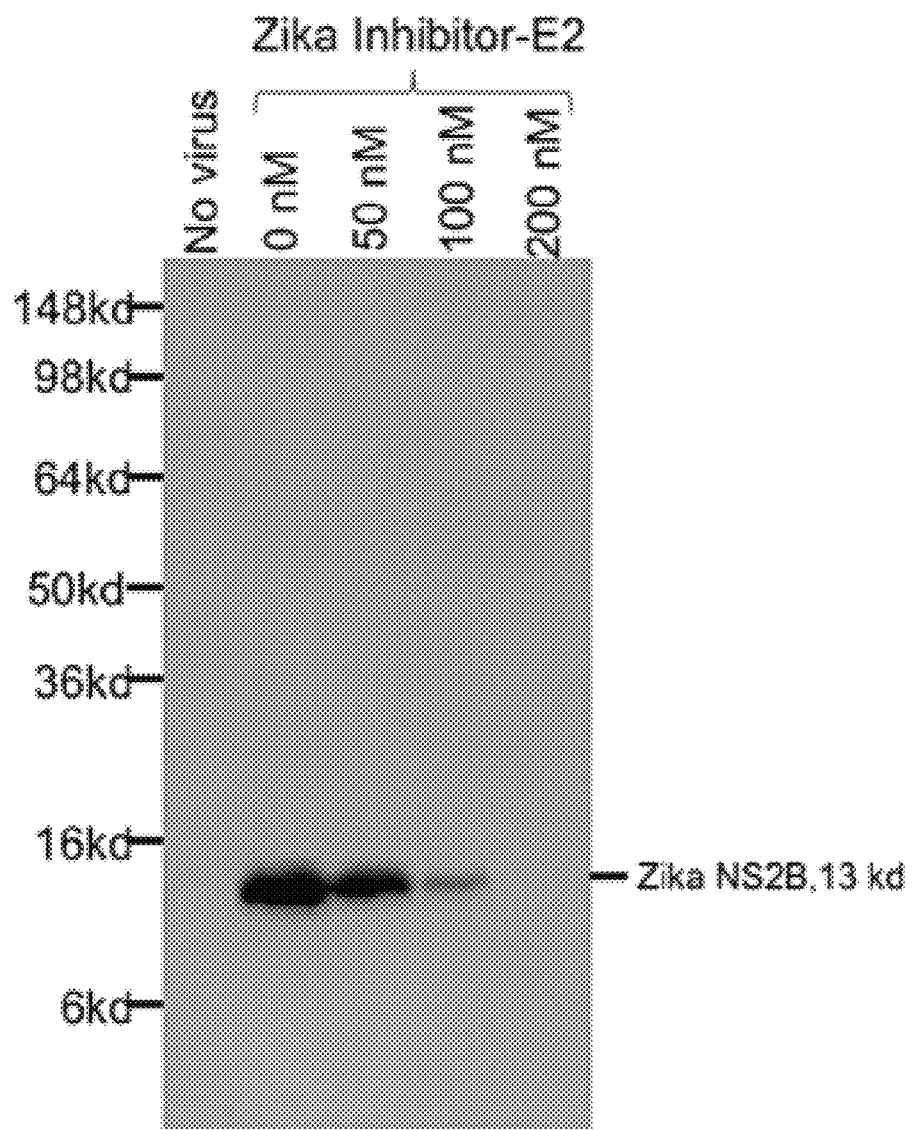
FIG. 3 shows a representative Western blot for Zika NS2B protein from Vero cell lysates of infectious Zika PRVABC59 virus.

Referring to FIG. 3, representative Western blot data for Zika NS2B protein from Huh7.5 cell lysates of infectious Zika PRVABC59 virus is shown. Without wishing to be bound by theory, infected cells treated with inhibitor validate 80 nM $EC_{50}$ that was also determined by CPE for infection of Vero cells.

The conditions and results of the in vitro antiviral screening assays are shown in Tables 1A-C below.

TABLE 1A

| Assay No. | Virus Screened | Virus Strain | Cell Line | Vehicle | Drug Conc. Range | Control Conc. Range |
|---|---|---|---|---|---|---|
| 1 | Dengue virus 2 | New Guinea C | Huh7 | $H_2O$ | 0.1-100 μM | 0.1-100 μg/ml |
| 2 | Dengue virus 2 | New Guinea C | Huh7 | $H_2O$ | 0.1-100 μM | 0.1-100 μg/ml |
| 3 | Zika | MR766 | Vero 76 | $H_2O$ | 0.1-100 μM | 0.1-100 μg/ml |

TABLE 1B

| Assay No. | Control Drug Name | Control Assay Order | Control Assay Name | $EC_{50}$ | $EC_{90}$ | $CC_{50}$ | $SI_{50}$ | $SI_{90}$ |
|---|---|---|---|---|---|---|---|---|
| 1 | 6-azauridine | Secondary | Visual (Virus yield reduction)/Neutral Red (Toxicity) | | 10 | >100 | | >10 |
| | | | Neutral Red (Cytopathic effect/Toxicity) | 5.3 | | >100 | >19 | |
| 2 | 6-azauridine | Secondary | Visual (Virus yield reduction)/Neutral Red (Toxicity) | | 1.8 | 27 | | 15 |
| | | | Neutral Red (Cytopathic effect/Toxicity) | 1.8 | | 27 | 15 | |
| 3 | 6-azauridine | Secondary | Visual (Virus yield reduction)/Neutral Red (Toxicity) | | >26.5 | 26.5 | | 0 |
| | | | Neutral Red (Cytopathic effect/Toxicity) | 0.66 | | 26.5 | 40 | |

TABLE 1C

| Assay No. | Control Drug Name | Control Assay Order | Control Assay Name | $EC_{50}$ | $EC_{90}$ | $CC_{50}$ | $SI_{50}$ | $SI_{90}$ |
|---|---|---|---|---|---|---|---|---|
| 1 | Isis-11 | Secondary | Visual (Virus yield reduction)/Neutral Red (Toxicity) | | 2.7 | 6.9 | | 2.6 |
| | | | Neutral Red (Cytopathic effect/Toxicity) | 1.8 | | 6.9 | 3.8 | |
| | DD041 | Secondary | Visual (Virus yield reduction)/Neutral Red (Toxicity) | | 10 | >100 | | >10 |
| | | | Neutral Red (Cytopathic effect/Toxicity) | 6.7 | | >100 | >15 | |
| 2 | Isis-11 | Secondary | Visual (Virus yield reduction)/Neutral Red (Toxicity) | | 0.38 | 2.4 | | 6.3 |
| | | | Neutral Red (Cytopathic effect/Toxicity) | 0.49 | | 2.4 | 4.9 | |
| | DD041 | Secondary | Visual (Virus yield reduction)/Neutral Red (Toxicity) | | 1.83 | 26 | | 14 |
| | | | Neutral Red (Cytopathic effect/Toxicity) | 5.6 | | 26 | 4.6 | |

TABLE 1C-continued

| Assay No. | Control Drug Name | Control Assay Order | Control Assay Name | $EC_{50}$ | $EC_{90}$ | $CC_{50}$ | $SI_{50}$ | $SI_{90}$ |
|---|---|---|---|---|---|---|---|---|
| 3 | Isis-11 | Secondary | Visual (Virus yield reduction)/Neutral Red (Toxicity) | | 0.93 | 20 | | 22 |
| | | | Neutral Red (Cytopathic effect/Toxicity) | 0.88 | | 20 | 23 | |
| | DD041 | Secondary | Visual (Virus yield reduction)/Neutral Red (Toxicity) | | 17 | >100 | | >5.9 |
| | | | Neutral Red (Cytopathic effect/Toxicity) | 11 | | >100 | >9.1 | | d. Mouse PK Evaluation i. Preparation of Compound Formulations

E1: 0.73 mg were dissolved in 1.217 mL of 20% HP-β-CD in water (w/v) with vortexing and sonification to obtain a 3 mg/kg, 5 mL/kg solution, IV solution. See also Table 2A below.

TABLE 2A

| Dilution Factor | Nominal (mg/mL) | Measured (mg/mL) | Mean (mg/mL) | Accuracy (%) | SD (mg/mL) | CV (%) |
|---|---|---|---|---|---|---|
| 2000 | 0.6 | 0.572 | 0.595 | 99.1 | 0.021 | 3.56 |
| 2000 | 0.6 | 0.598 | | | | |
| 2000 | 0.6 | 0.614 | | | | |

E2: 0.66 mg were dissolved in 1.100 mL of 20% HP-β-CD in water (w/v) with vortexing and sonification to obtain a 3 mg/kg, 5 mL/kg solution, IV solution. See also Table 2B below.

TABLE 2B

| Dilution Factor | Nominal (mg/mL) | Measured (mg/mL) | Mean (mg/mL) | Accuracy (%) | SD (mg/mL) | CV (%) |
|---|---|---|---|---|---|---|
| 2000 | 0.6 | 0.664 | 0.662 | 110 | 0.002 | 0.302 |
| 2000 | 0.6 | 0.660 | | | | |
| 2000 | 0.6 | 0.662 | | | | |

DD041: 0.55 mg were dissolved in 0.916 mL of 20% HP-β-CD in water (w/v) with vortexing and sonification to obtain a 3 mg/kg, 5 mL/kg solution, IV solution. See also Table 2C below.

TABLE 2C

| Dilution Factor | Nominal (mg/mL) | Measured (mg/mL) | Mean (mg/mL) | Accuracy (%) | SD (mg/mL) | CV (%) |
|---|---|---|---|---|---|---|
| 2000 | 0.6 | 0.686 | 0.679 | 113 | 0.022 | 3.23 |
| 2000 | 0.6 | 0.696 | | | | |
| 2000 | 0.6 | 0.654 | | | | | ii. Analytical Method

The desired serial concentrations of working solutions were achieved by diluting stock solution of analyte with 50% acetonitrile in water solution. 5 μL of working solutions (2, 4, 20, 100, 200, 1000, 2000, and 4000 ng/mL) were added to 10 μL of the blank CD-1 mice plasma to achieve calibration standards of 1-2000 ng/mL (1, 2, 10, 50, 100, 500, 1000, and 2000 ng/mL) in a total volume of 15 μL. Four quality control samples at 2 ng/mL, 5 ng/mL, 50 ng/mL, and 1600 ng/mL for plasma were prepared independently of those used for the calibration curves. These QC samples were prepared on the day of analysis in the same way as calibration standards.

15 μL standards, 15 μL QC samples, and 15 μL unknown samples (10 μL plasma with 5 μL blank solution) were added to 200 μL of acetonitrile containing IS mixture for precipitating protein respectively. Then the samples were vortexed for 30 s. After centrifugation at 4 degree Celsius, 3900 rpm for 15 min, the supernatant was diluted 3 times with water. 20 μL of diluted supernatant was injected into the LC/MS/MS system for quantitative analysis.

iii. In Vivo Plasma PK Results

Figure 4A:
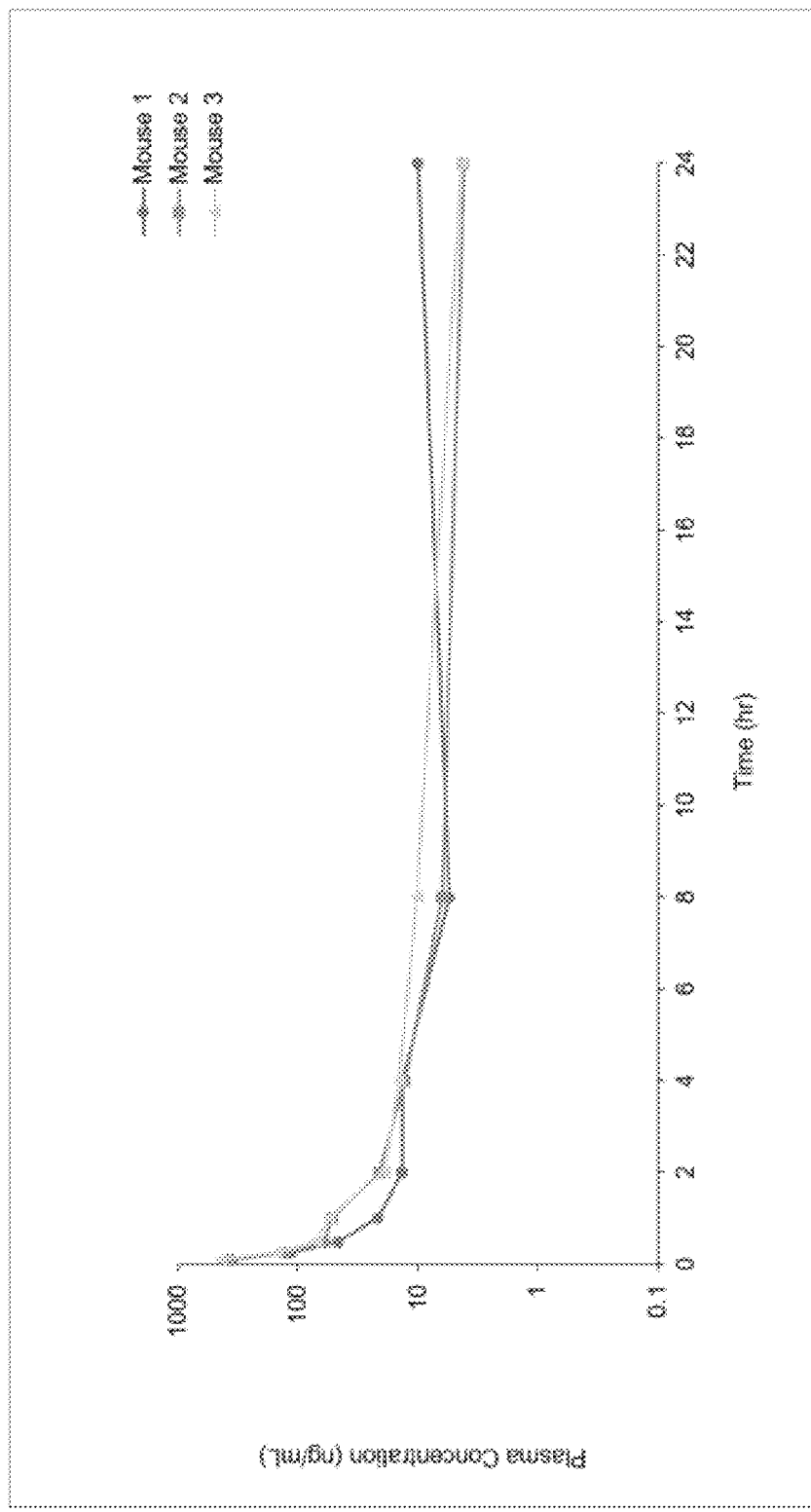
FIG. 4A and FIG. 4B show representative data illustrating the plasma concentration versus time profile (FIG. 4A) and mean plasma concentration versus time profile (FIG. 4B) for E1 after 3 mg/kg IV in CD-1 mice.
Figure 4B:
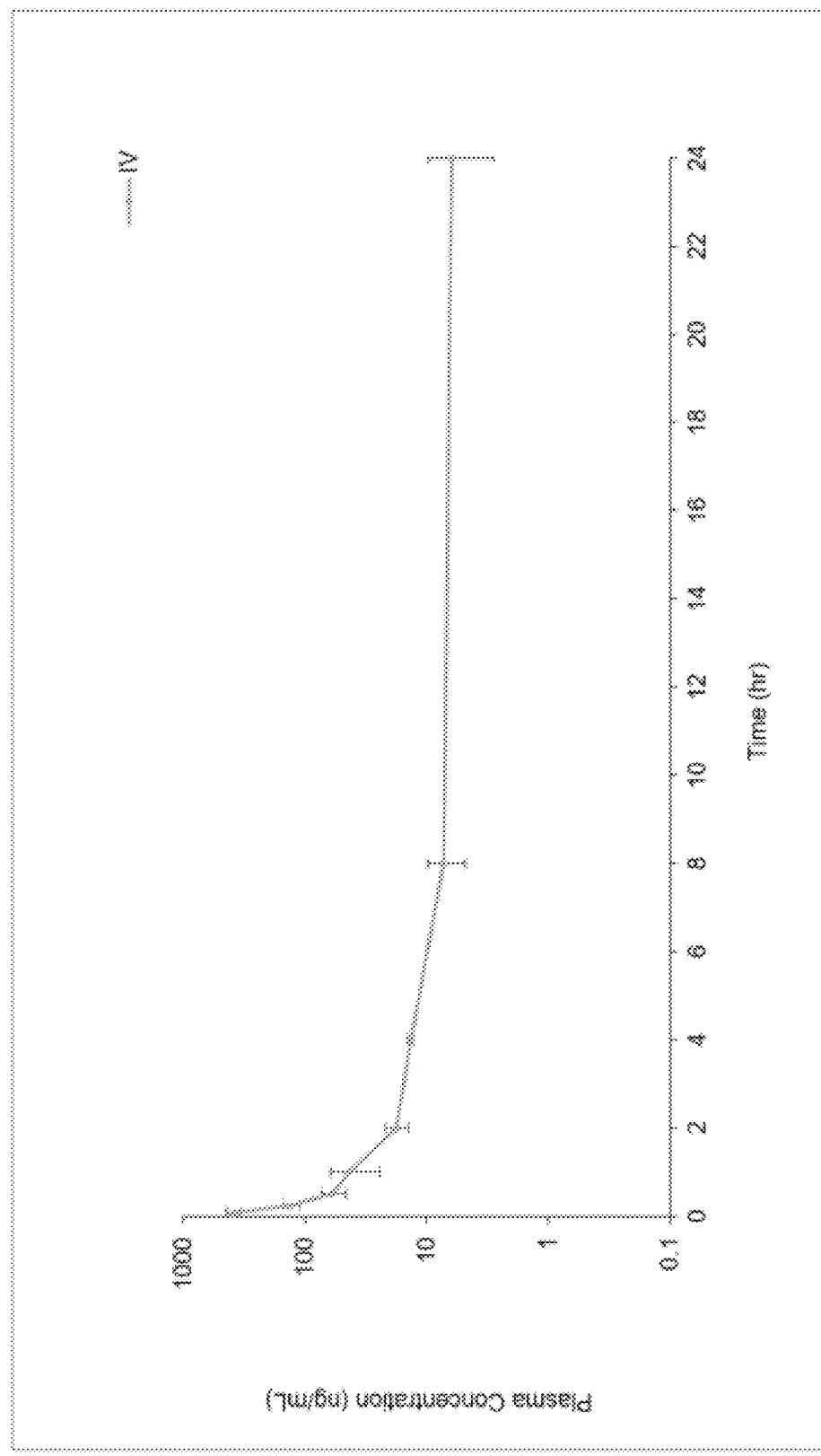
Figure 5A:
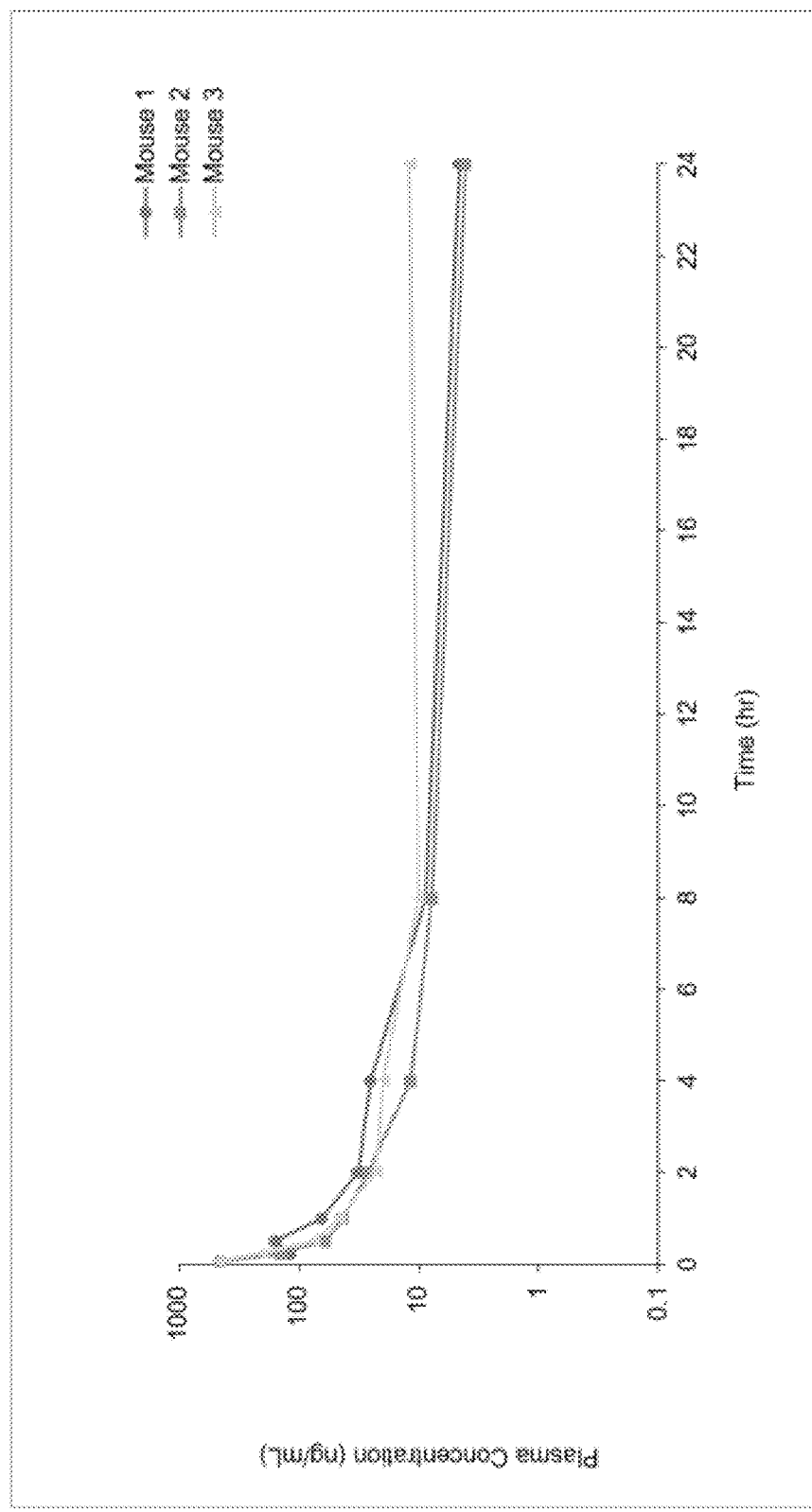
FIG. 5A and FIG. 5B show representative data illustrating the plasma concentration versus time profile (FIG. 5A) and mean plasma concentration versus time profile (FIG. 5B) for E2 after 3 mg/kg IV in CD-1 mice.
Figure 5B:
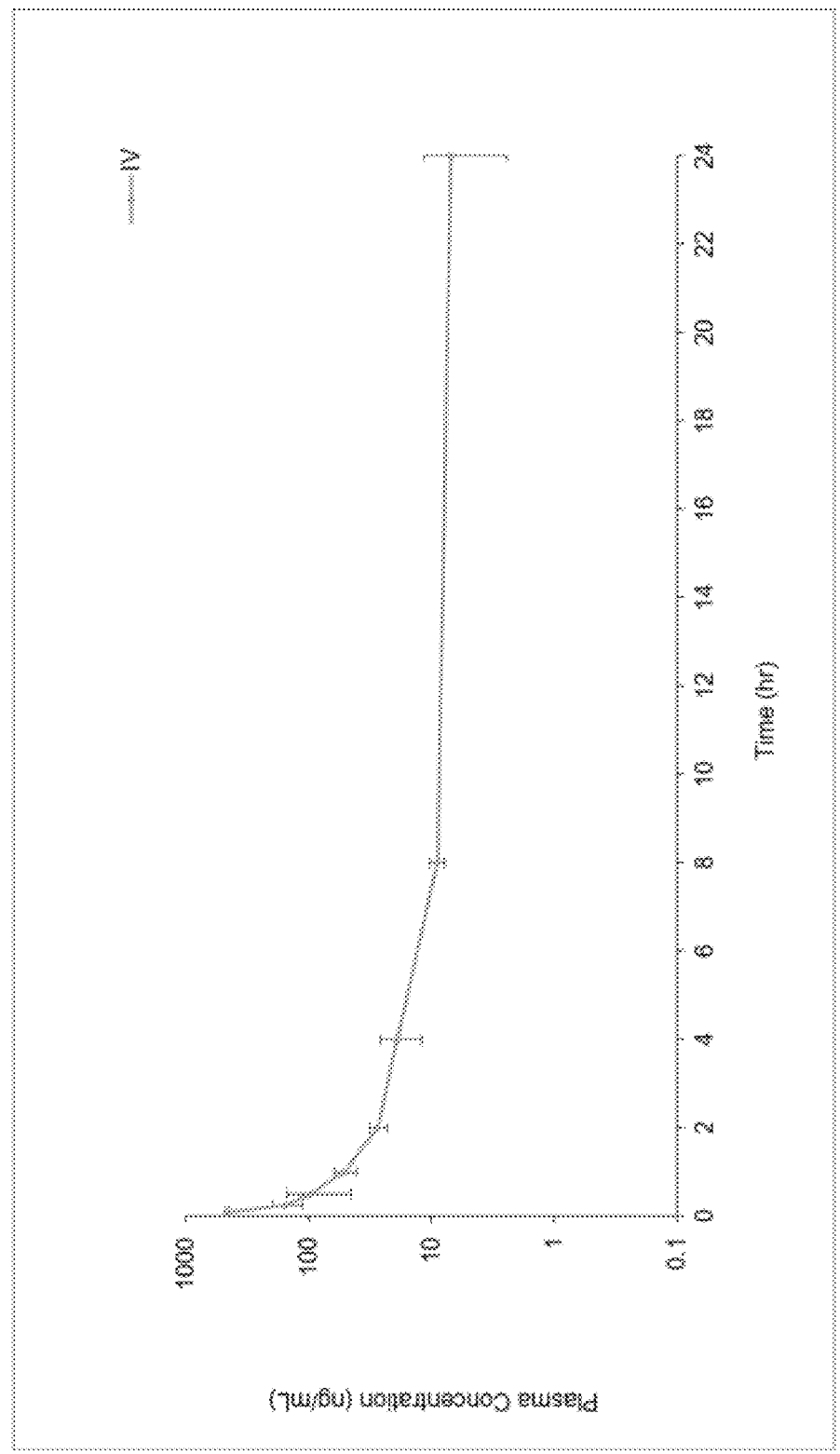
Figure 6A:
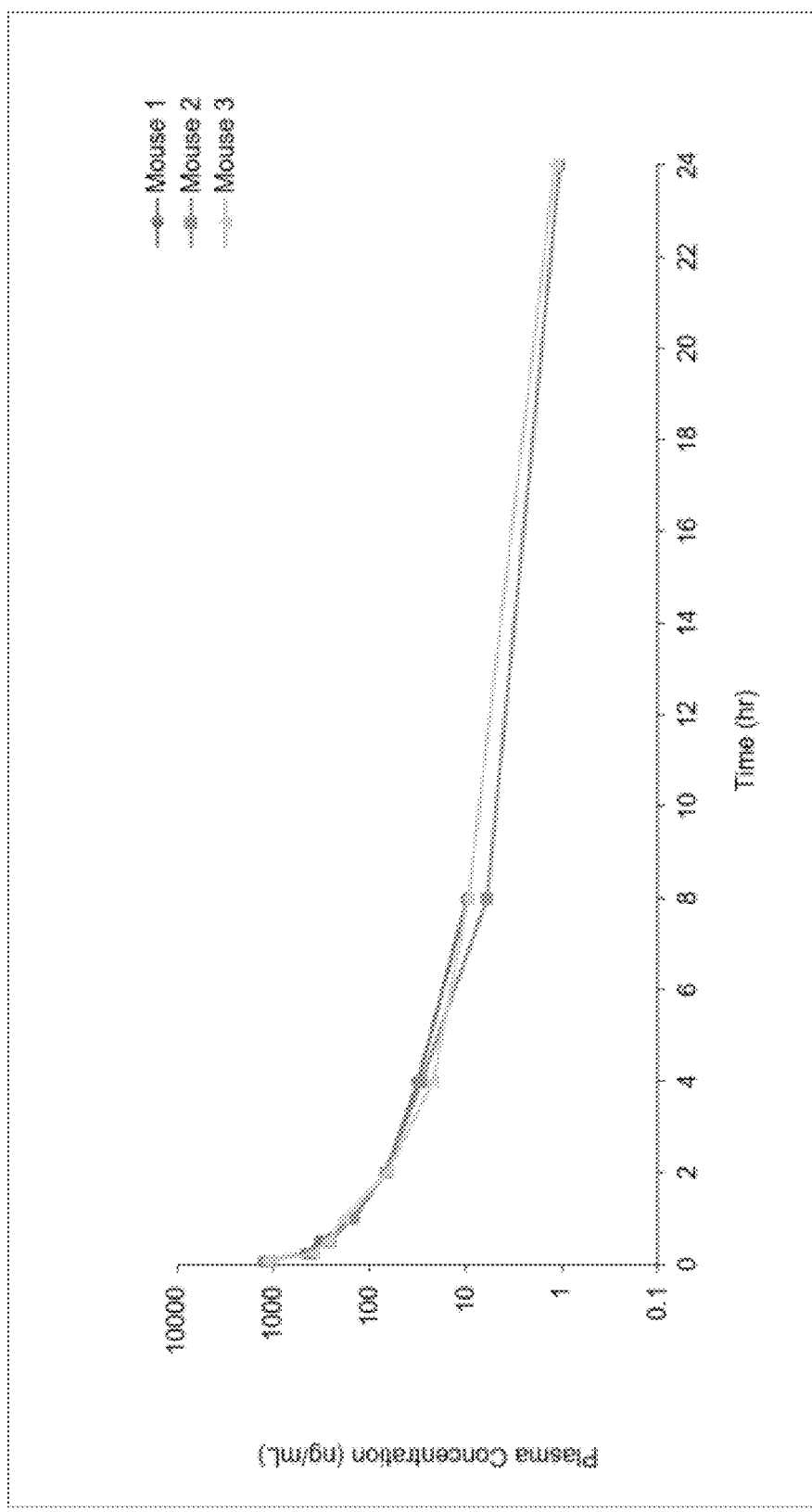
FIG. 6A and FIG. 6B show representative data illustrating the plasma concentration versus time profile (FIG. 6A) and mean plasma concentration versus time profile (FIG. 6B) for DD041 after 3 mg/kg IV in CD-1 mice.
Figure 6B:
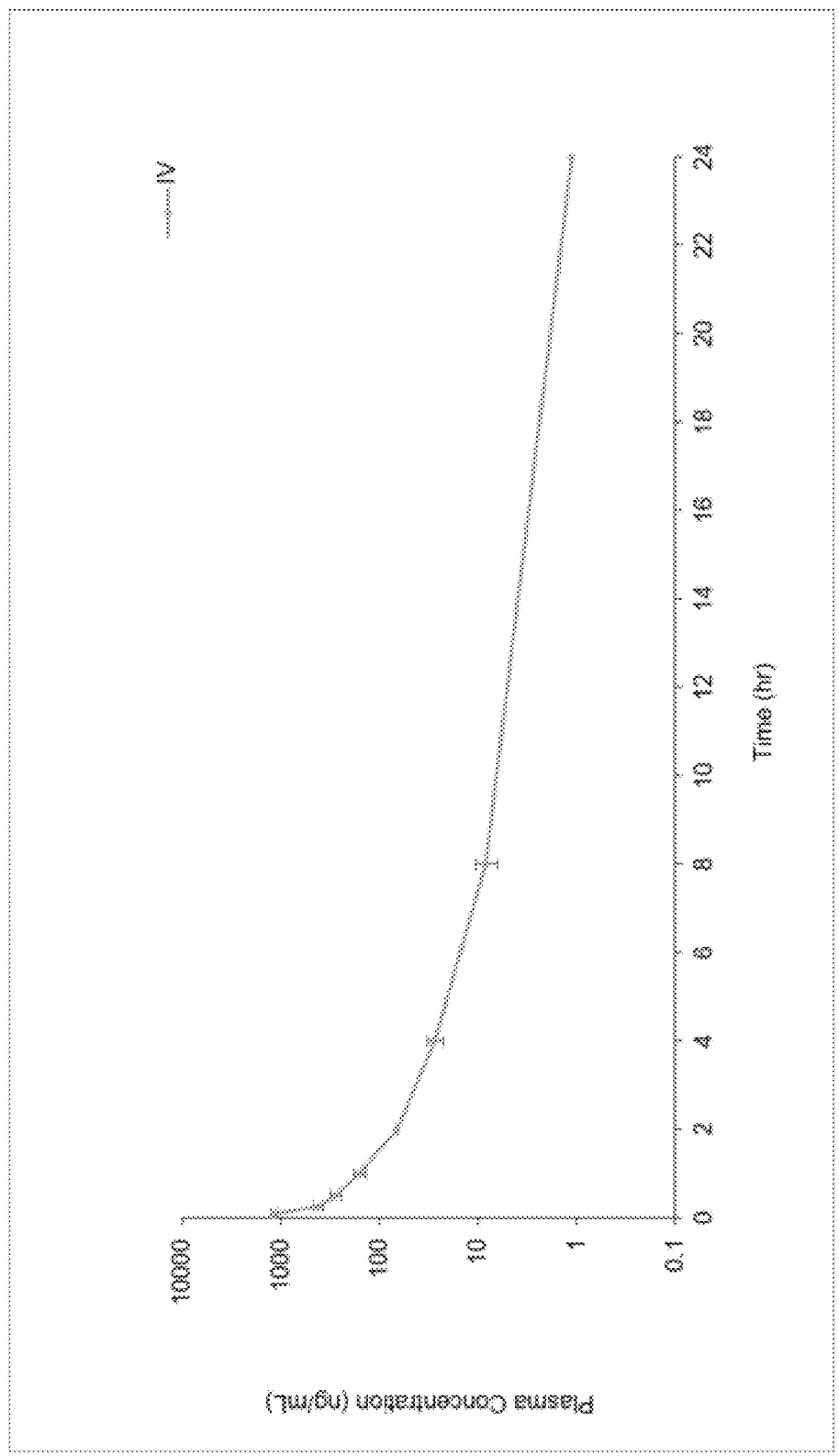

The IV plasma concentration-time data for E1, E2, and DD C4 V are shown in Tables 3A-C, respectively, and FIG. 4A-B, FIG. 5A-B, and FIG. 6A-B, respectively. Referring to FIG. 4A-B, the in vivo plasma PK for compound E2 is shown. Without wishing to be bound by theory, these data indicate that therapeutic levels can likely be obtained in the mouse models proposed herein. Thus, without wishing to be bound by theory, the structure of E2 will likely lend itself to effective CNS penetration.

TABLE 3A

| Time (h) | Concentration (ng/mL) Mouse 1 | Mouse 2 | Mouse 3 | Mean (ng/mL) | SD (ng/mL) | CV (%) |
|---|---|---|---|---|---|---|
| 0.083 | 352 | 367 | 443 | 387 | 49 | 12.6 |
| 0.25 | 113 | 126 | 154 | 131 | 21 | 16.0 |
| 0.5 | 45.5 | 60.9 | 71.0 | 59.1 | 12.8 | 21.7 |
| 1 | 21.4 | 51.8 | 55.5 | 42.9 | 18.7 | 43.6 |
| 2 | 13.4 | 20.7 | 19.2 | 17.8 | 3.9 | 21.7 |
| 4 | 13.3 | 12.9 | 14.3 | 13.5 | 0.7 | 5.34 |
| 8 | 5.50 | 6.20 | 10.2 | 7.30 | 2.54 | 34.7 |
| 24 | 10.0 | 4.11 | 4.33 | 6.1 | 3.3 | 54.3 |

TABLE 3B

| Time (h) | Concentration (ng/mL) Mouse 1 | Mouse 2 | Mouse 3 | Mean (ng/mL) | SD (ng/mL) | CV (%) |
|---|---|---|---|---|---|---|
| 0.083 | 445 | 452 | 473 | 457 | 15 | 3.19 |
| 0.25 | 118 | 143 | 203 | 155 | 44 | 28.2 |
| 0.5 | 158 | 60.2 | 75.5 | 98 | 53 | 53.7 |
| 1 | 64.0 | 42.7 | 46.5 | 51.1 | 11.4 | 22.2 |
| 2 | 31.9 | 26.8 | 22.8 | 27.2 | 4.6 | 16.8 |
| 4 | 25.4 | 11.7 | 19.8 | 19.0 | 6.9 | 36.3 |
| 8 | 8.79 | 7.76 | 10.2 | 8.9 | 1.2 | 13.7 |
| 24 | 4.57 | 4.10 | 12.1 | 6.9 | 4.5 | 64.8 |

TABLE 3C

| Time (h) | Concentration (ng/mL) Mouse 1 | Mouse 2 | Mouse 3 | Mean (ng/mL) | SD (ng/mL) | CV (%) |
|---|---|---|---|---|---|---|
| 0.083 | 1250 | 1070 | 1190 | 1170 | 92 | 7.83 |
| 0.25 | 470 | 403 | 377 | 417 | 48 | 11.5 |
| 0.5 | 322 | 255 | 267 | 281 | 36 | 12.7 |
| 1 | 145 | 152 | 187 | 161 | 23 | 13.9 |
| 2 | 67.5 | 66.4 | 63.3 | 65.7 | 2.2 | 3.31 |
| 4 | 31.6 | 28.5 | 22.0 | 27.4 | 4.9 | 17.9 |
| 8 | 9.69 | 6.00 | 9.51 | 8.40 | 2.08 | 24.8 |
| 24 | BLOQ | 1.05 | 1.17 | 1.11 | NA | NA |

A summary of the pharmacokinetic parameters for E1, E2, and DD041 is shown in Tables 4A-C, respectively.

TABLE 4A

| PK parameters | Unit | Mouse 1 | Mouse 2 | Mouse 3 | Mean | SD | CV(%) |
|---|---|---|---|---|---|---|---|
| Cl_obs | mL/min/kg | 116 | 122 | 106 | 115 | 8 | 6.85 |
| $T_{1/2}$ | h | NA | NA | 12.0 | NA | NA | NA |
| $C_0$ | ng/mL | 619 | 624 | 749 | 664 | 74 | 11.1 |
| $AUC_{last}$ | h * ng/mL | 321 | 324 | 395 | 347 | 42 | 12.0 |
| $AUC_{Inf}$ | h * ng/mL | NA | NA | 470 | NA | NA | NA |
| $AUC\_{\%Extrap}\_obs$ | % | 25.7 | 20.8 | 15.9 | 20.8 | 4.9 | 23.5 |
| $MRT_{Inf}\_obs$ | h | NA | NA | 10.7 | NA | NA | NA |
| $AUC_{last}/D$ | h * mg/mL | 107 | 108 | 132 | 116 | 14 | 12.0 |
| $V_{ss}\_obs$ | L/kg | 104 | 96.2 | 68.3 | 90 | 19 | 21.0 |

$T_{1/2}$ was reported as NA since the Rsq < 0.85.

$AUC_{Inf}$ and $MRT_{Inf}\_obs$ were reported as NA sincie the Extra > 20%.

TABLE 4B

| PK parameters | Unit | Mouse1 | Mouse2 | Mouse3 | Mean | SD | CV(%) |
|---|---|---|---|---|---|---|---|
| Cl_obs | mL/min/kg | 95.0 | 113 | 64.1 | 91 | 25 | 27.1 |
| $T_{1/2}$ | h | NA | 14.2 | NA | NA | NA | NA |
| $C_0$ | ng/mL | 861 | 801 | 720 | 794 | 71 | 8.88 |
| $AUC_{last}$ | h * ng/mL | 472 | 360 | 487 | 439 | 69 | 15.8 |
| $AUC_{Inf}$ | h * ng/mL | 526 | 444 | NA | 485 | NA | NA |
| $AUC\_{\%Extrap}\_obs$ | % | 10.4 | 18.9 | 37.6 | 22.3 | 13.9 | 62.4 |
| $MRT_{Inf}\_obs$ | h | 7.67 | 12.2 | NA | 9.9 | NA | NA |
| $AUC_{last}/D$ | h * mg/mL | 157 | 120 | 162 | 146 | 23 | 15.8 |
| $V_{ss}\_obs$ | L/kg | 43.7 | 82.5 | 87.0 | 71.1 | 23.8 | 33.5 |

$T_{1/2}$ was reported as NA since the Rsq < 0.85.

$AUC_{Inf}$ and $MRT_{Inf}\_obs$ were reported as NA sincie the Extra > 20%.

TABLE 4C

| PK parameters | Unit | Mouse 1 | Mouse 2 | Mouse 3 | Mean | SD | CV(%) |
|---|---|---|---|---|---|---|---|
| Cl_obs | mL/min/kg | 61.4 | 65.8 | 60.3 | 62.5 | 2.9 | 4.61 |
| $T_{1/2}$ | h | 2.17 | 4.65 | 4.87 | 3.90 | 1.50 | 38.5 |
| $C_0$ | ng/mL | 2033 | 1738 | 2107 | 1959 | 195 | 9.95 |
| $AUC_{last}$ | h * ng/mL | 784 | 753 | 821 | 786 | 34 | 4.30 |
| $AUC_{Inf}$ | h * ng/mL | 814 | 760 | 829 | 801 | 36 | 4.51 |
| $AUC\_{\%Extrap}\_obs$ | % | 3.73 | 0.927 | 0.993 | 1.88 | 1.60 | 84.9 |
| $MRT_{Inf}\_obs$ | h | 1.57 | 2.15 | 2.31 | 2.01 | 0.39 | 19.3 |
| $AUC_{last}/D$ | h * mg/mL | 261 | 251 | 274 | 262 | 11 | 4.30 |
| $V_{ss}\_obs$ | L/kg | 5.80 | 8.48 | 8.37 | 7.55 | 1.52 | 20.1 | e. Maximum Tolerated Dose (MTD) Data

Isis-11 (E2) has been shown to have some toxicity in mice, despite broad activity against flaviviruses in cell culture. An initial study in AG129 mice showed substantial toxicity when administered bid, once a day at total daily doses of 32, 10, or 3.2 mg/kg/d. A second study showed that a dose of 3.2 or 1.0 mg/kg/d administered once every third day was well-tolerated with no indication of toxicity. Without wishing to be bound by theory, the purpose of this study is to further identify the MTD and dosing frequency that can be used for Isis-11 (E2) in future antiviral efficacy studies.

i. Materials and Methods

Animals: 21 AG129 mice produced by an in-house colony were used. Groups of animals were assigned by weight to experimental groups and individually marked with ear tags.

Test agent: Isis-11 (E2) was provided by University of Utah for testing in the mouse model.

Experiment Design: Mice were treated either every other day (eod) or every third day (q3d) with Isis-11 (E2) via i.p. injection at doses of 32, 10, or 3.2 mg/kg/d. Additional treatments were administered at various time points. Mice were monitored for mortality until 14 days post-initial treatment (dpi). Individual weights were measured daily 0-10 dpi and on 14 dpi.

Statistical analysis: Survival data were analyzed using the Wilcoxon log-rank survival analysis and all other statistical analyses were done using one-way ANOVA using a Bonferroni group comparison (Prism 5, GraphPad Software, Inc.).

Ethics regulation of Laboratory animals: This study was conducted in accordance with the approval of the Institutional Animal Care and Use Committee of Utah State University dated 20 Feb. 2014 (Protocol #2339). The work was done in the AAALAC-accredited Laboratory Animal Research Center of Utah State University. The U. S. Government (National Institutes of Health) approval was renewed 1 Apr. 2010 (PHS Assurance no. A3801-01) in accordance with the National Institutes of Health Guide for the Care and Use of Laboratory Animals (Revision; 2010).

ii. Results and Discussion

This study confirmed the toxicity of Isis-11 (E2) at a dose of 32 mg/kg, regardless of administration every other day (eod) for 4 treatments or every third day (q3 d) for 3 total treatments. The mice treated with this upper dose all succumbed to the toxic effects of the compound between 3 and 7 days after initial treatment and had weight loss. A dose of 10 mg/kg resulted in an intermediate mortality rate with 2 of 5 total animals succumbing to toxicity between 7 and 9 dpi regardless of eod or q3 d treatment. Mice treated with the intermediate dose displayed some transient weight loss, but an overall weight gain between 0 and 14 days after initial treatment. Treatment with 3.2 mg/kg resulted in no mortality or weight loss and appears to be the maximum tolerated dose with no weight loss or mortality observed (Table 4D) Without wishing to be bound by theory, this suggests future antiviral studies should be performed with a dose of 3.2 mg/kg administered eod for 4 treatments.

TABLE 4D

| Animals: AG129 mice | | Duration of experiment: 14 days Treatment vol./schedule: 0.1 ml, variable dosing, q 3 d × 3 | |
|---|---|---|---|
| Virus/route: N/A | | | Mean wt. |
| Treatment | Alive/total | $MDD^a \pm SD$ | change$^b$ (g) ± SD |
| Isis-11 (E2), 3.2 mg/kg/d | 3/3 | >14.0 ± 0.0 | −0.1 ± 0.8 |
| Isis-11 (E2), 1.0 mg/kg/d | 3/3 | >14.0 ± 0.0 | −1.2 ± 0.8 |
| Saline Placebo | 3/3 | >14.0 ± 0.0 | −0.4 ± 0.1 |

$^a$Average day of death.
$^b$Difference between weight on 0 and 2 days post-initial treatment representing maximal weight change within this study.

iii. Conclusions

In sum, treatment with 3.2 mg/kg of Isis-11 (E2) administered eod or q3 d was well-tolerated in AG129 mice. Treatment with higher doses of 10 or 32 mg/kg were toxic regardless of eod or q3 d frequency.

2. Evaluation of Benzimidazole Analogs as Myc Translation Inhibitors

Without wishing to be bound by theory, benzimidazole analogs have demonstrated modulation of c-Myc activity via translation inhibition. C-Myc is a transcription factor that is overexpressed in many cancer types. This overexpression is linked to upregulation of many other genes, as well as to rapid proliferation of cancers. The Myc gene family comprises, for example, c-Myc, 1-Myc, and n-Myc. To date, as many as 20% of human cancers have been associated with the overexpression of c-Myc.

a. SUFO-KO Light Assays and Dual-Luciferase Assays

The c-Myc translation activity of benzimidazole analogs is shown in Table 5 below. $IC_{50}$ SUFO-KO-Light values are for inhibition of Gli-luciferace activity in the SUFU-KO-light cells developed by the James Chen laboratory at Stanford University.

TABLE 5

| Compound No. | $IC_{50}$ (µM) SUFU-KO-Light |
|---|---|
| Isis-11 (racemic) | 0.2 |
| Isis-11 (−isomer/E2) | 0.1 |
| Isis-11 (+isomer/E1) | 5.0 |
| Isis-12 IBIS-560020 | 1.5 |
| Isis-13 IBIS-560146 | >2 |
| Isis-4 | 10 |
| Isis-187 | >5 |
| Isis-075 | 0.36 |

The dual luciferase plasmid construct described by Willis and co-workers was transfected into Huh 7.5 cells. The *Renilla* luciferase cistron is translated from a 5' cap, then the Myc 5' UTR is placed in front of firefly luciferase to evaluate cap-independent translation from the same mRNA. Notably, Isis-11 (racemic) inhibits both cap-dependent and cap-independent translation, but has a larger effect on cap-independent translation initiated from the Myc 5'-UTR. This assay is a proxy for c-Myc translation activity. See also Stoneley et al. (2000) *Nucleic Acids Res.* 28: 687-94.

Without wishing to be bound by theory, the correlation between structure and activity indicates that a methyl-dimethylamine substituted furan ring may be a key pharmacophore, as the two stereoisomers of this 5-membered ring have dramatically different activities in the SUFU-KO-Light assay and in the Myc-IRES translation reporter assay, The 6-membered pyran compounds, while still active, are less potent.

Figure 7B:
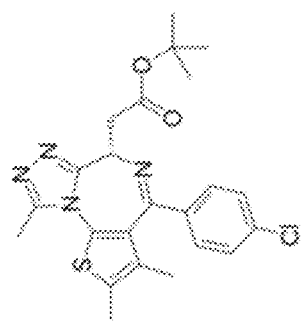
FIG. 7A-7C show representative data illustrating the effects of benzimidazoles described herein on the levels of Gli-1 and c-Myc as determined by Wester blot in SUFU-KO-Light cells. The benzimidazole effects are compared to the effect of JQ1.
Figure 7B:
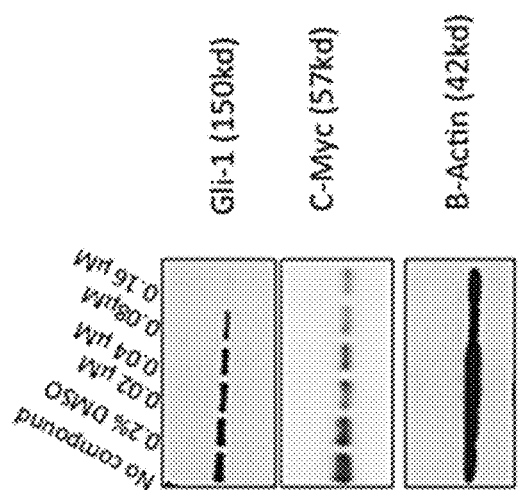
Figure 7A:
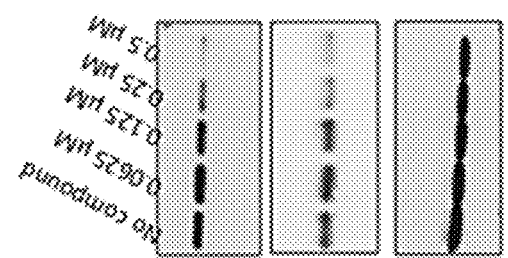

Referring to FIG. 7A and FIG. 7B, the SUFU-KO-Light cells were treated with compounds for 48 hours. The cells were lysed by RIPA buffer. Samples were loaded on 10% SDS-PAGE gel and immunoblotting were performed using antibodies on the right side, as shown. Changes in Gli-1 and c-Myc levels may be coordinated depending on the molecular target. Isis-11 (racemic) (here, referred to as Isis-11) and JQ1 decrease both Gli-1 and c-Myc in SUFO-KO-Light cells. C-Myc mRNA levels increase slightly upon Isis-11 treatment, supporting an effect on translation rather than transcription.

Figure 7C:
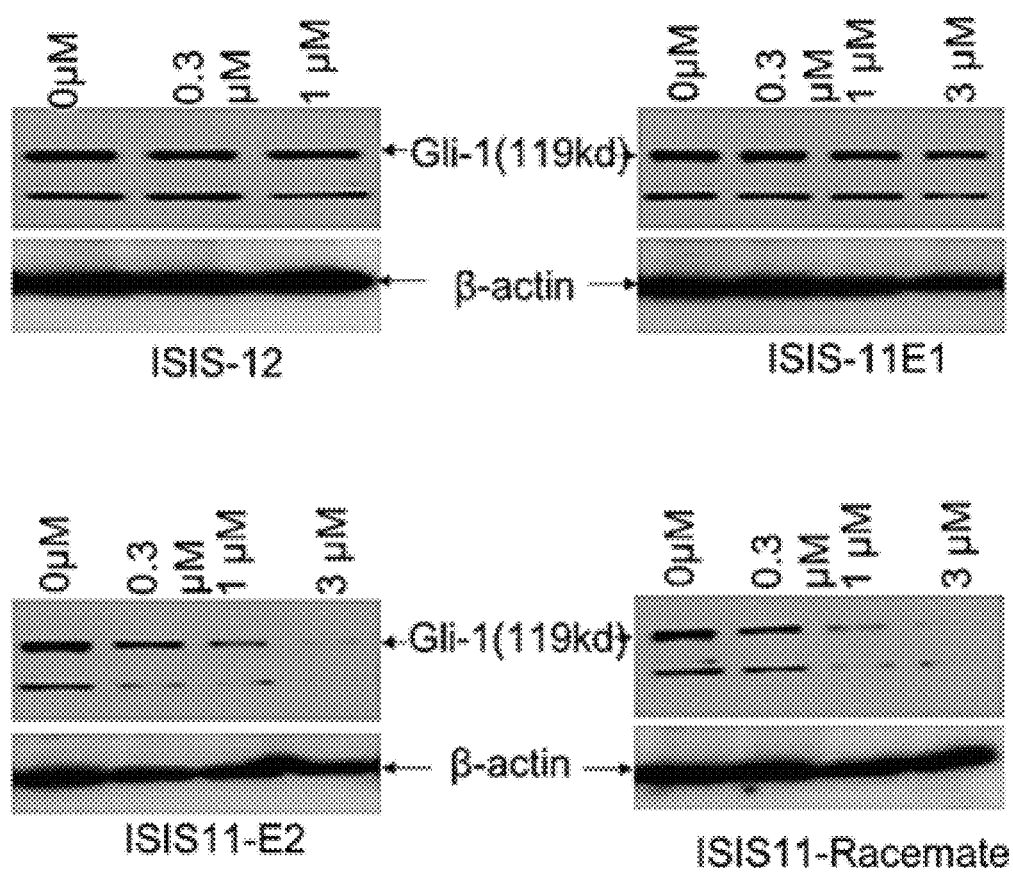

Referring to FIG. 7C, SUFU-KO-Light t cells were treated with compounds as indicated for 48 hours followed by western blotting assay using Gli-1 (Abcam) and R-actin (Sigma) antibodies.

b. Evaluation of Anti-Proliferation Activity

The anti-proliferation against Chronic Myeloid Leukemia (CML) was evaluated in a colony-forming assay using CML CD34+ cells obtained from recently diagnosed leukemia patients. The activity of Isis-11 (racemic) was evaluated against two cell isolates. The $EC_{50}$ value was approximately 0.15 micromolar for inhibition of colony formation. This compares favorably with $IC_{50}$ of Imatinib against wild type BCR-ABL (O'Hare et al. (2005) Cancer Res. 65(11): 4500-4505). Without wishing to be bound by theory, Isis-11 (racemic) is expected to have similar potency against tyrosine kinase inhibitor (i.e., imatinib) resistant mutants as against the wild type BCR-ABL cells, allowing for effective treatment of tyrosine kinase inhibitor resistant cancers.

Table 5 below shows inhibition by Isis-11 of CML CD34+ colony formation for the two CML colonies 14-290 and 15-186. The approximate $EC_{50}=0.15$ μM. At 0.8 μM, colony formation is completely inhibited.

TABLE 6

|  | 0 μM | 0.1 μM | 0.2 μM | 0.4 μM | 0.8 μM | 1.6 μM |
| --- | --- | --- | --- | --- | --- | --- |
| 14-290 | 100 | 91.81 | 19.40 | 12.50 | 0 | 0 |
| 15-186 | 100 | 87.06 | 52.10 | 38.81 | 0 | 0 |
| AVG | 100 | 89.44 | 35.75 | 25.66 | 0 | 0 | c. Assay for Inhibition of C-Myc and N-Myc

Figure 8:
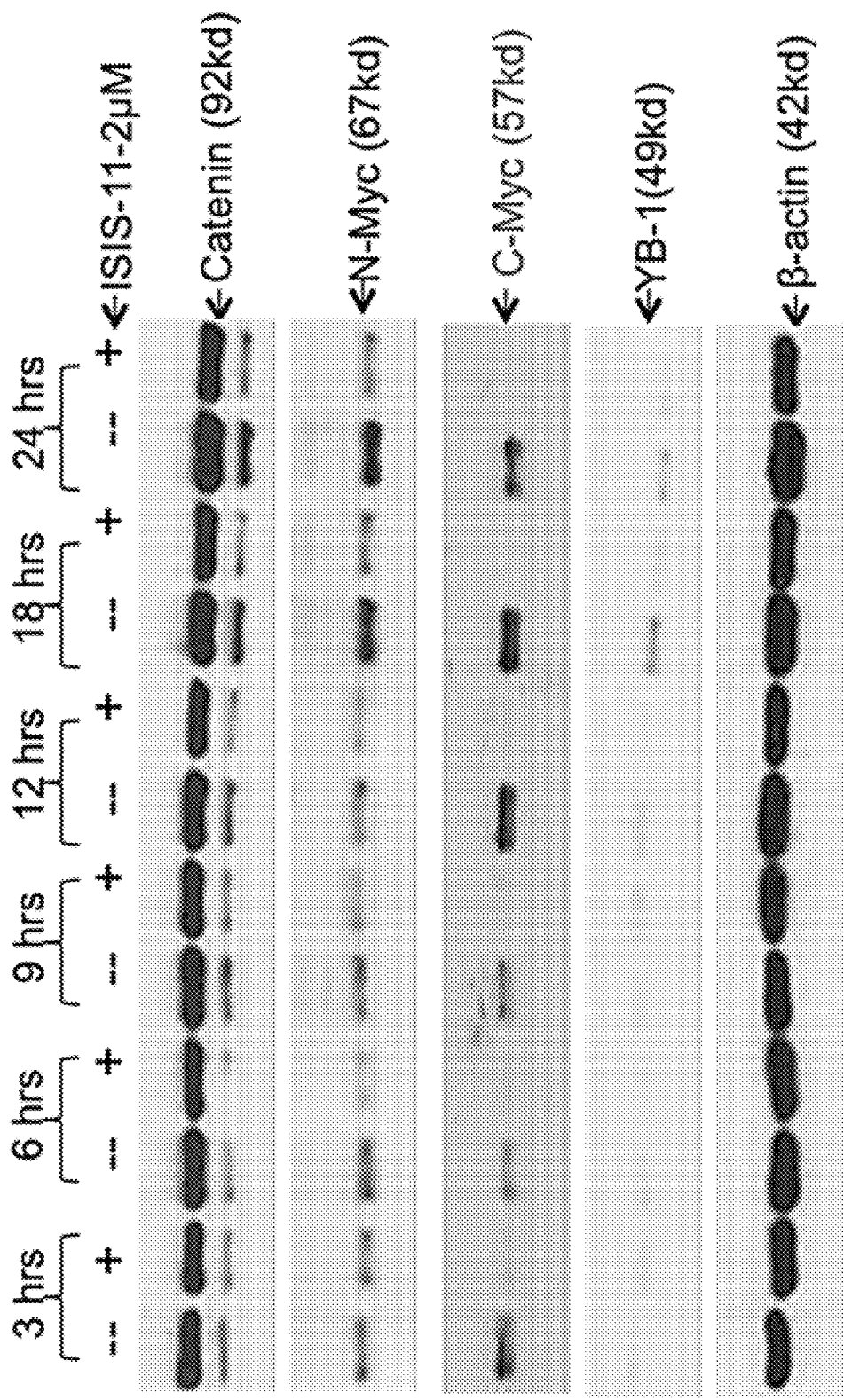
FIG. 8 shows representative data illustrating Isis-11-E2 inhibition of C-Myc and N-Myc.

Referring to FIG. 8, the ability of Isis-11 (racemic) to inhibit c-Myc and n-Myc was evaluated. Huh7.5 cells were treated with 2 μM compound or no compound as a control. The cells were lysed and harvested at the indicated times. Western blotting was performed using antibodies as shown after serial stripping. Both c-Myc and n-Myc were inhibited at the protein level. YB-1 is known to be part of a positive feedback loop with Myc and is also affected by Myc inhibition.

d. Raji Cell Viability

Figure 9:
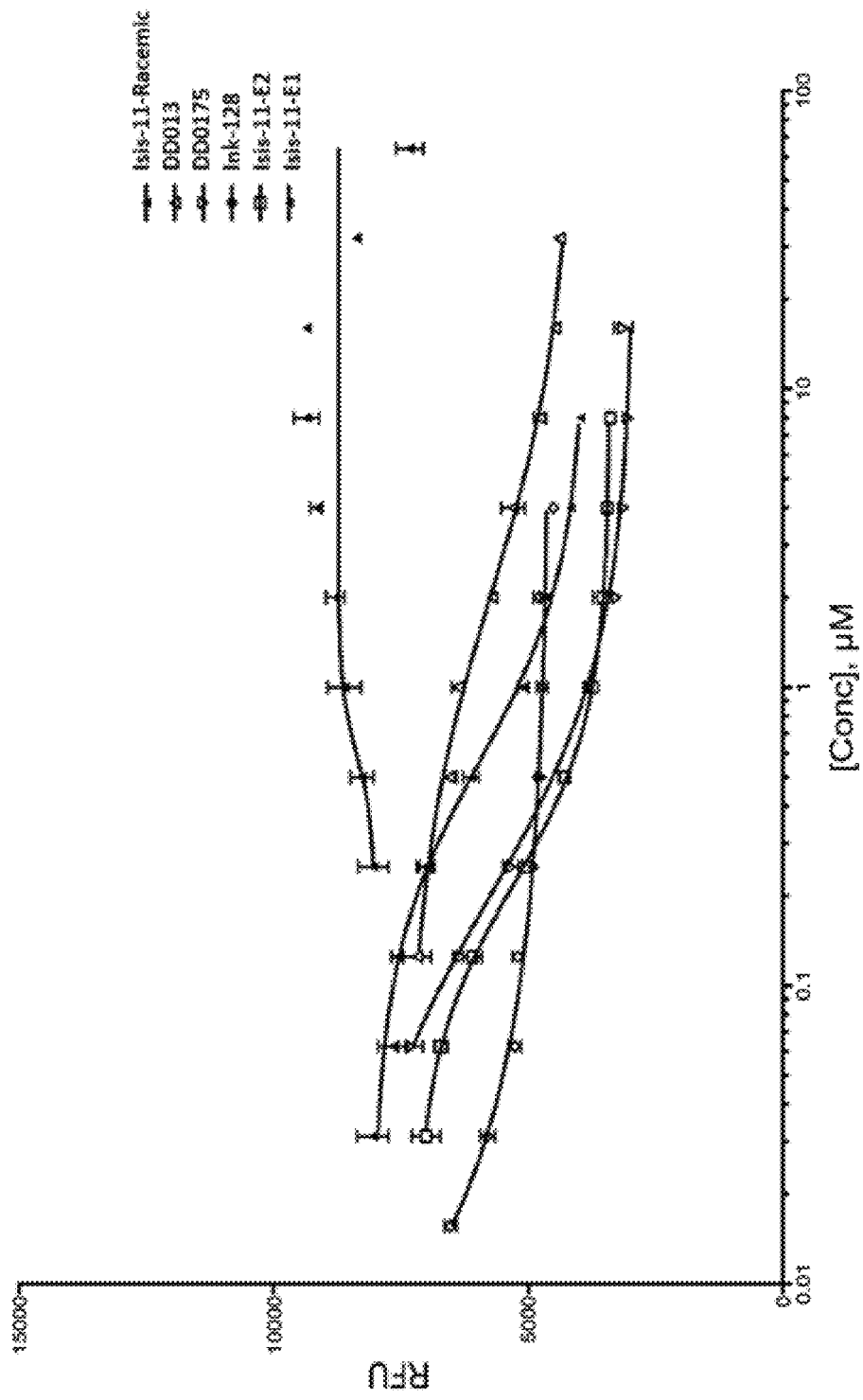
FIG. 9 shows representative data illustrating that Isis-11 and structurally related benzimidazoles inhibit proliferation of Burkitt Lymphoma Model Cell Line (Raji). Compound DD013 (IBIS-560146); Compound DD0175 (IBIS-561075)

The activity of benzimidazole analogs against a Burkitt Lymphoma cell line is shown in FIG. 9. Specifically, the compounds were evaluated in both Raji and Ramos cell lines (only Raji data are shown). Without wishing to be bound by theory, both Isis-11 (racemic) and Isis-11 E2 potently inhibited Raji cell proliferation, with $IC_{50}$'s of 500 nm and 200 nm, respectively.

e. Differential Effect on Myc P64/P67 Translation

Figure 10:
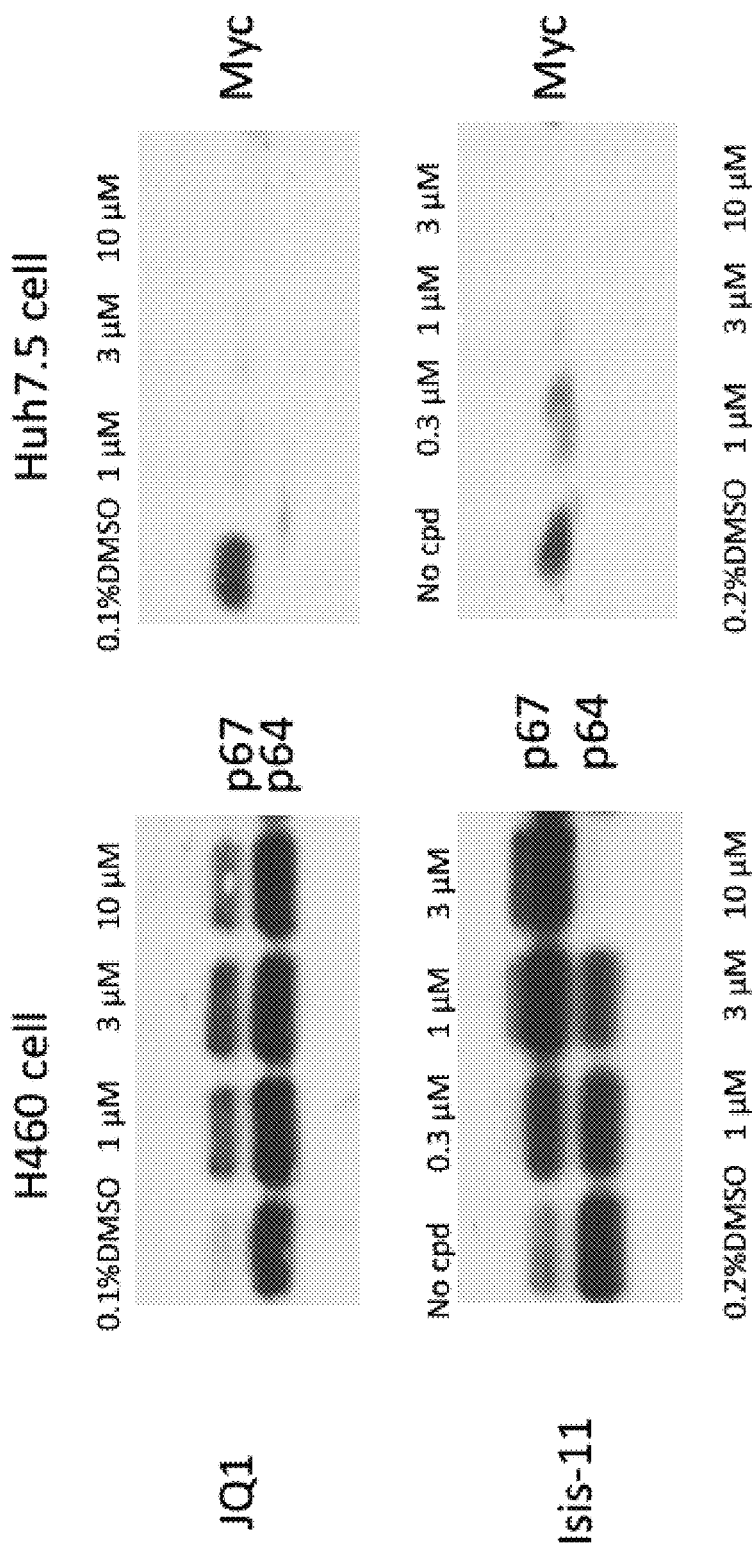
FIG. 10 shows representative data illustrating the differential effect of Isis-11 on Myc p64/p67 protein levels. The selective effect of Isis-11 on p64 and p67 protein translation is compared to the effect of JQ1 that affects c-Myc transcription.

H460 and Huh7.5 cells were treated with diluted compounds for 24 hours, followed by western blotting using anti-c-Myc antibody (see FIG. 10). Two Myc isoforms, p64 and p67, are from alternative translational start sites on the same mRNA. Without wishing to be bound by theory, the differential response to Isis-11 (racemic) is inconsistent with regulation at the transcriptional level.

f. Time-Course Assay

Figure 11:
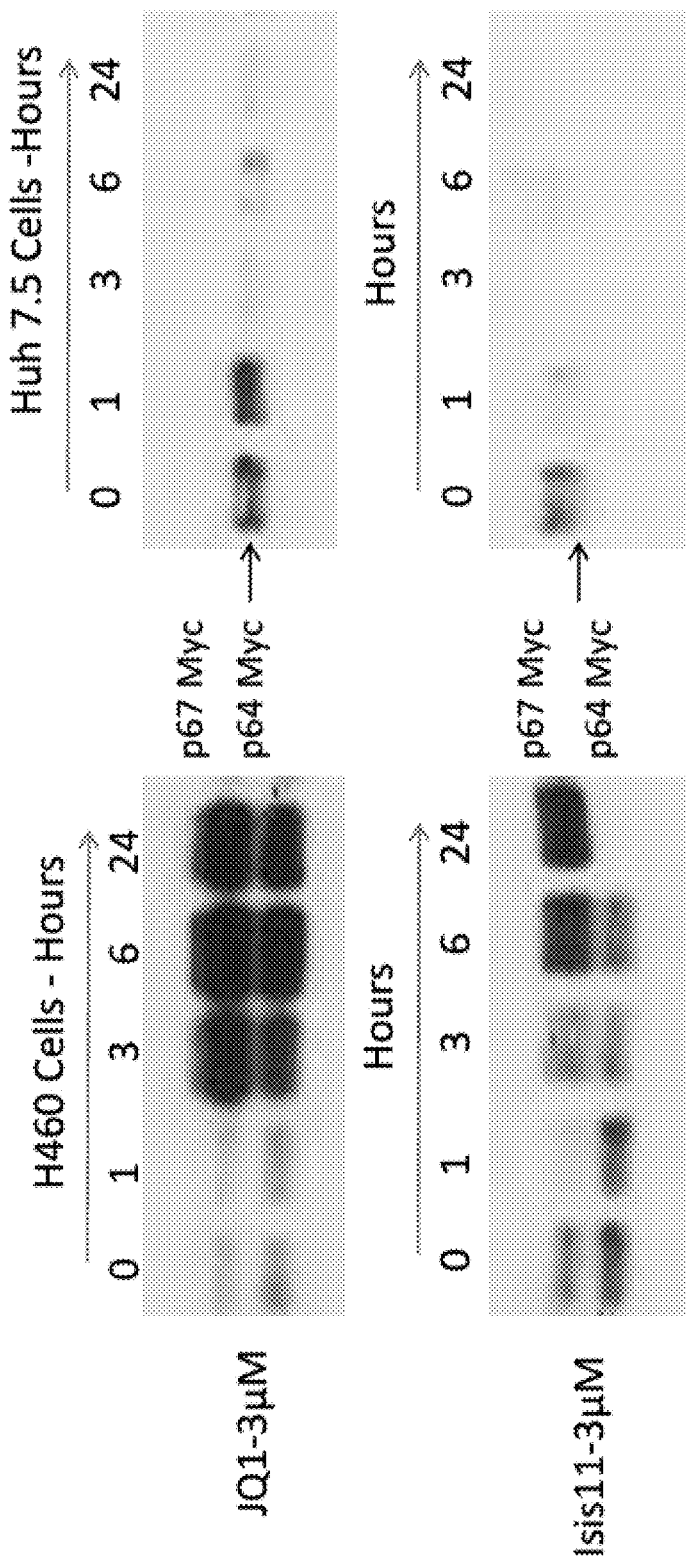
FIG. 11 shows representative data from a time course assay for JQ1 and Isis-11

H460 and Huh7.5 cells were treated with compounds, and cells were lysed and harvested at the indicated times (see FIG. 11). Western blotting was performed using anti-C-Myc antibody. JQ1 shows effects at the transcriptional level that change both p64/p67 simultaneously.

g. Western Blot Assay Using Anti-C-Myc and B-Actin

Figure 12:
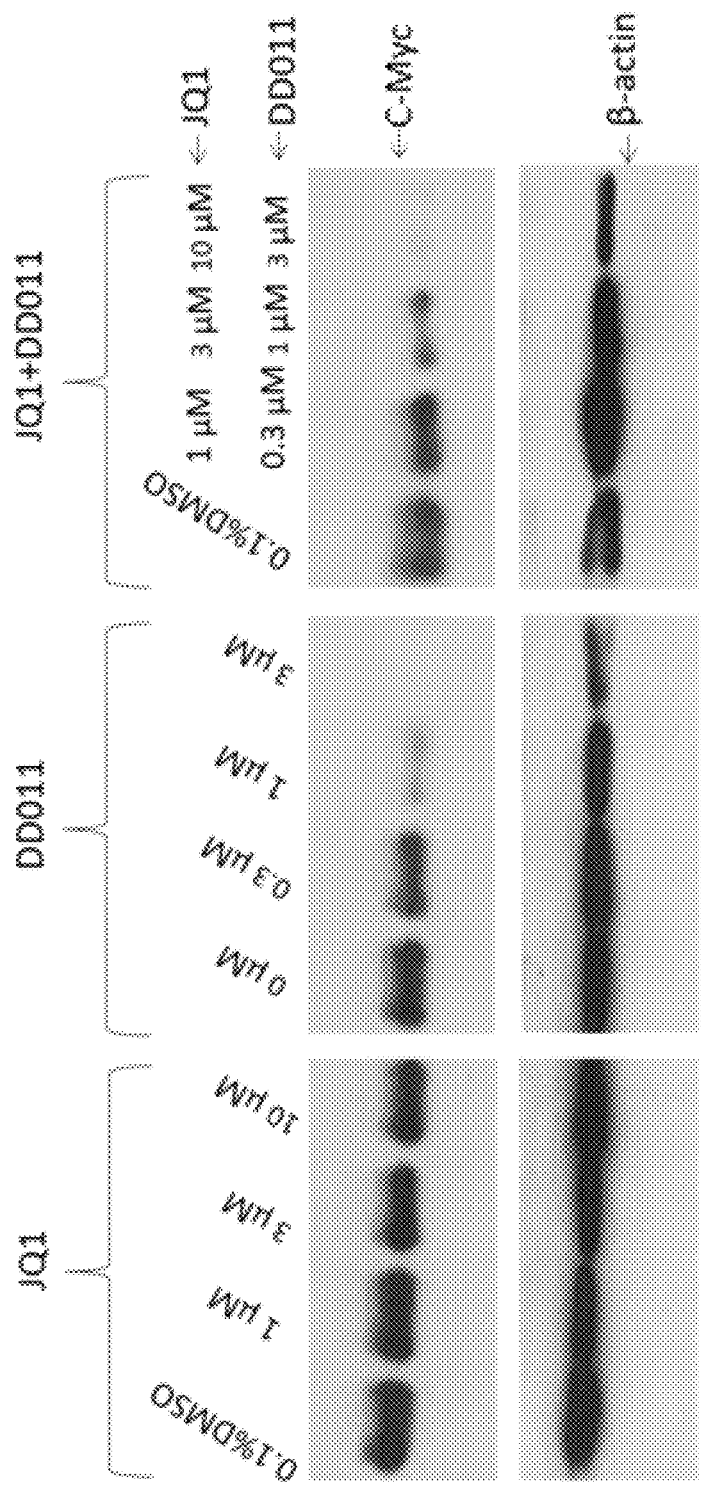
FIG. 12 shows representative data illustrating Isis-11 inhibition of C-Myc in Huh7.5.

Referring to FIG. 12, Huh7.5 cells were treated with compounds as shown for 24 hours following western blotting assay using anti-C-Myc and β-actin.

h. Western Blot Assay Using Mb002 Cells

Figure 13:
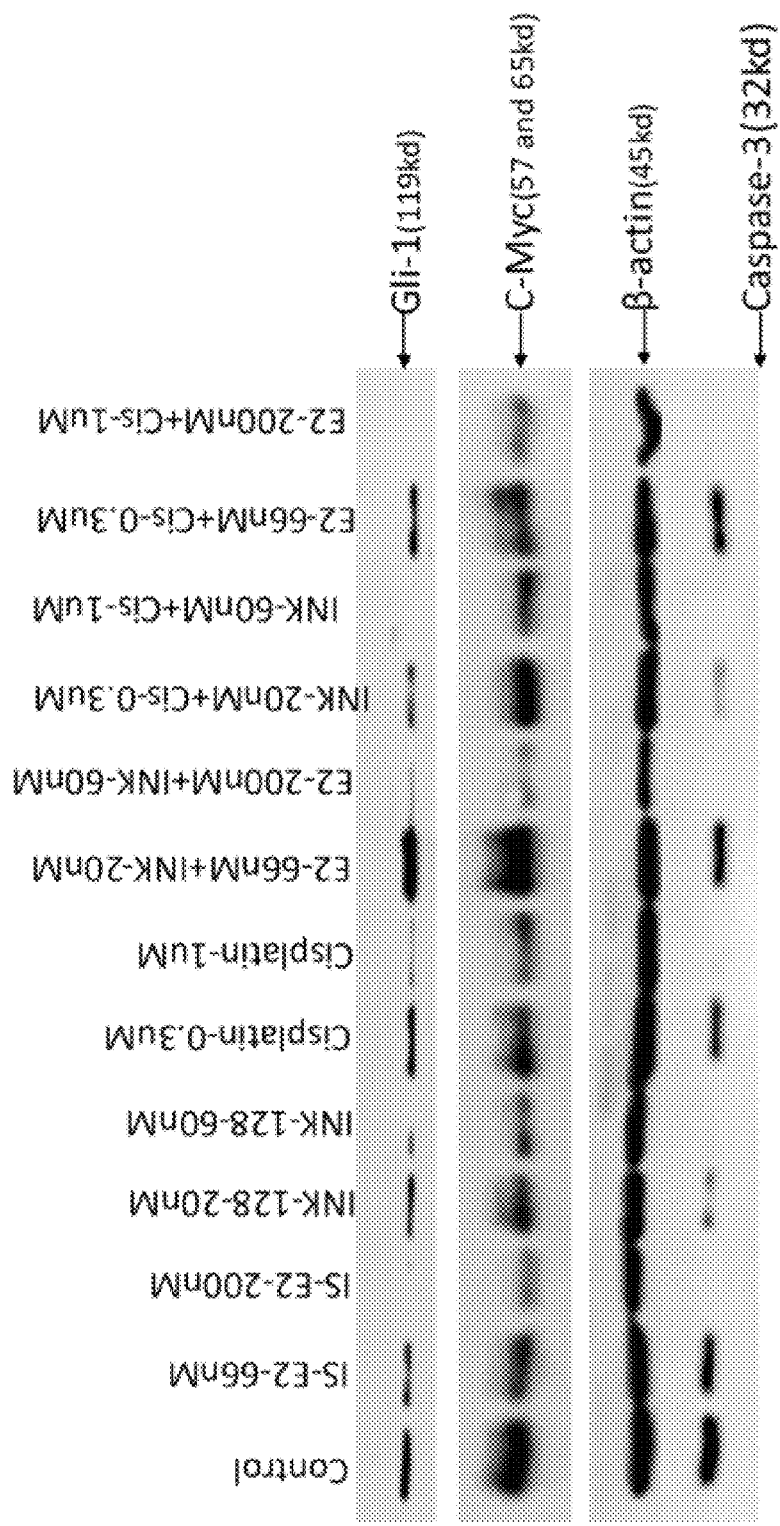
FIG. 13 shows representative data illustrating the results of Western blot of MB002 cells using antibodies of anti-Gli-1, anti-C-Myc, anti-Caspase-3, and anti-β-actin.

Referring to FIG. 13, MB002 cells (c-Myc driven medulloblastoma cell line) were seeded in a 24-well plate and cultured overnight. Next, the cells were treated with compounds as indicated for 72 hours followed by a series of western blots using antibodies of anti-Gli-1, anti-C-Myc, Anti-Caspase-3, and anti-β-actin. The membranes were stripped in between probing for Gli-1, c-Myc, β-actin, and Caspase-3.

i. MTT Assay

Figure 14:
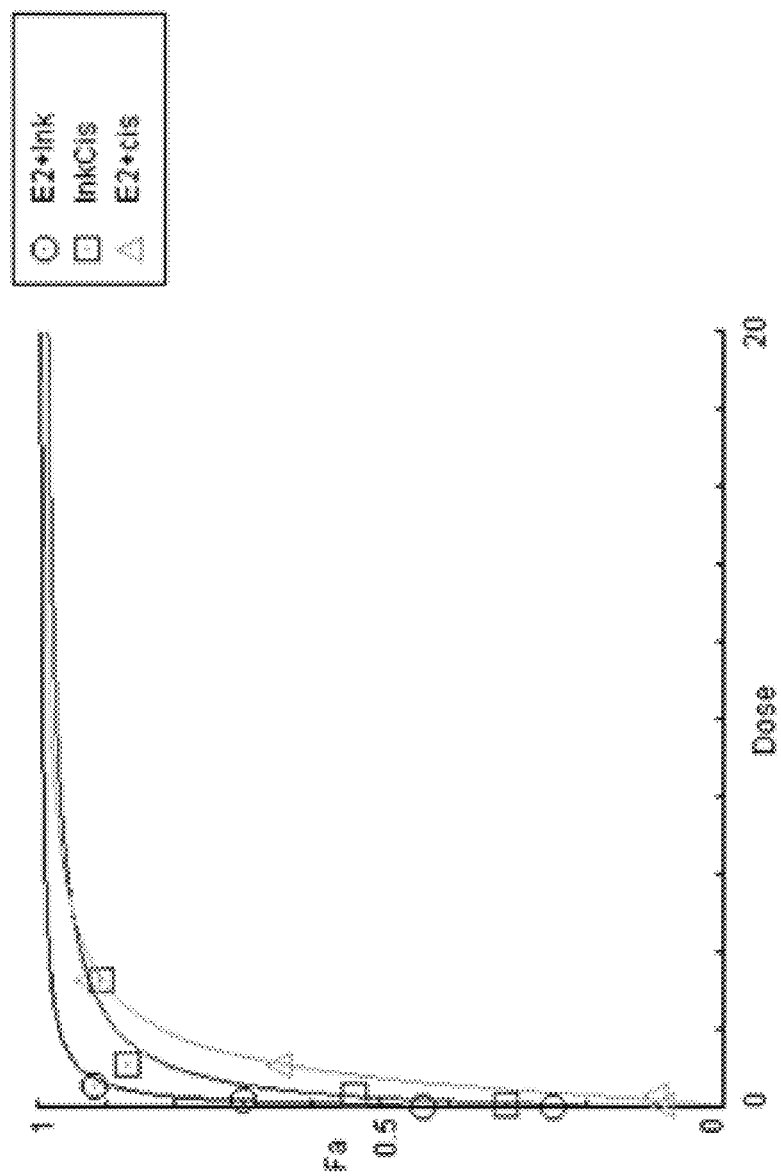
FIG. 14 shows representative data of cell viability determined by MTT assay wherein MB002 cells are treated with inhibitor E2, Ink-128, or Cisplatin. Fa is the fractional effect; the dose is in units of micromolar. The MTT colorimetric intensity was evaluated by Compusyn software.

The MTT detected inhibition of cellular proliferation is shown in FIG. 14 and Table 7 below. Specifically, Table 7 shows the dose in micromolar for Fa=0.5 inhibition (50%) for MB002 cell proliferation in response to Isis-11 E2, Ink-128, cisplatin, or a combination thereof as indicated.

TABLE 7

| Drug/Combo | CI value | Dose E2 | Dose Ink | Dose Cis | Dose E1 |
| --- | --- | --- | --- | --- | --- |
| Isis-11 E2 |  | 0.32 |  |  |  |
| Ink-128 |  |  | 0.06 |  |  |
| Cisplatin |  |  |  | 0.78 |  |
| Isis-11 E1 |  |  |  |  | 16.49 |
| E2 + Ink | 0.63500 | 0.034 | 0.034 |  |  |
| Ink + Cis | 0.62068 |  | 0.02138 | 0.21382 |  |
| E2 + Cis | 1.01654 | 0.06769 |  | 0.67690 |  |

Referring to Table 8, the CI values for E2+Ink-128 and for E2+Cisplatin indicate more synergy at higher effective dose (ED) levels. Without wishing to be bound by theory, this may be particularly beneficial for anticancer therapy where cell killing is important. Ink-128 has been shown effective in cell culture, but clinical trials as monotherapy are disappointing. The combination of Ink-128+E2 could result in tumor regression at very low combination doses. At Fa=0.9, the combination dose of Ink-128 and E2 is 290 nM of each compound, a very achievable therapeutic dose for in vivo evaluation.

TABLE 8

| Combo | $ED_{50}$ | $ED_{75}$ | $ED_{90}$ | $ED_{95}$ |
| --- | --- | --- | --- | --- |
| E2 + Ink | 0.63500 | 0.42621 | 0.29233 | 0.22966 |
| InkCis | 0.62068 | 0.61194 | 0.67793 | 0.76685 |
| E2 + Cis | 1.01654 | 0.87484 | 0.76086 | 0.69527 |

The $EC_{50}$ values shown below in Table 9 were determined for Isis-11 (E2) by MTT assay in the Medulloblastoma cell lines as indicated.

TABLE 9

| Cell Line | Isis-11 E2 $EC_{50}$ (nM) |
| --- | --- |
| Shh-NPD (Hh subcategory) | 720 |
| UW-426 (Hh subcategory) | 105 |
| MB002 (Myc subcategory) | 430 | j. Dose-Effect Curves

Figure 15:
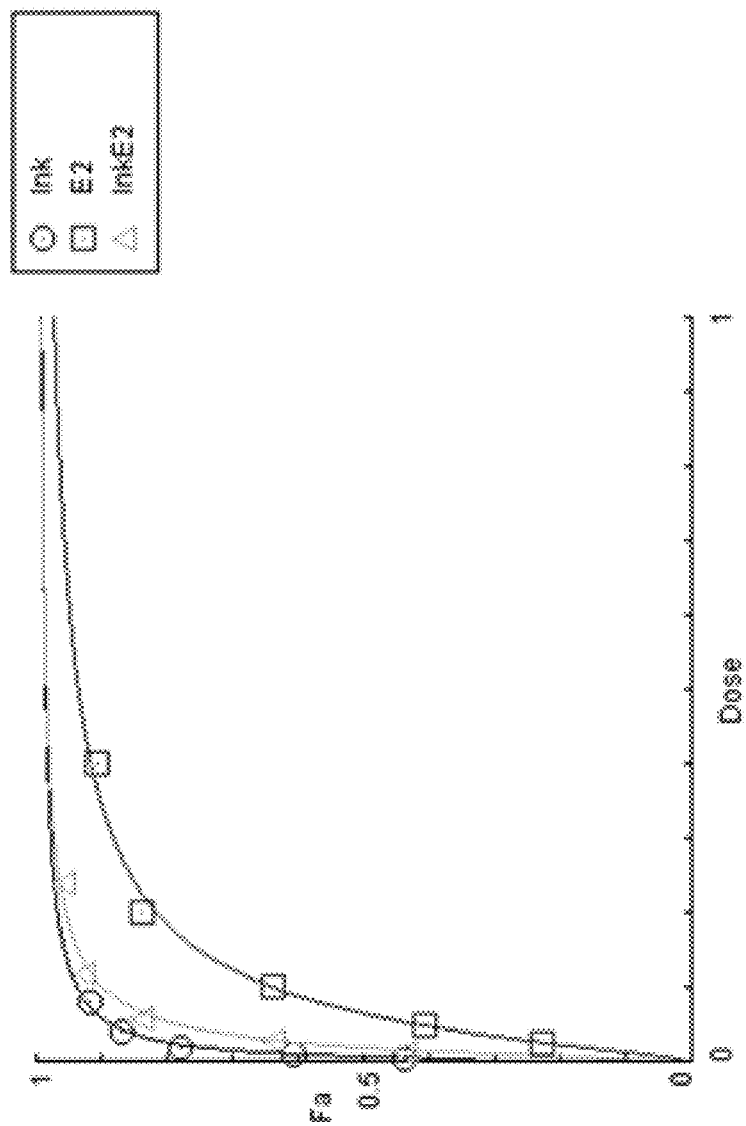
FIG. 15 shows representative dose-effect curves for Ink-128, E2, and the combination of Ink-128+E2 in SUFU-KO-Light cells expressing Gli-luciferase. Fa is the fractional effect, the dose is in units of micromolar. The luciferase intensity as determined by dual-Glo assay was evaluated by Compusyn software

Referring to FIG. 15, dose-effect curves for Ink-128, E2, and the combination of Ink-128+E2, in SUFU-KO-Light cells expressing Gli-luciferase is shown. Table 10A below shows the CI (synergy vale) at different effective doses, showing that at greater effects there is increased Synergy. Table 10B shows Synergy at Fa=0.5, indicating that the $EC_{50}$ for Ink-128 is 6 nM and for E2 is 60 nM as single agents. For the combination, a combined dose of 2.9 nM and 14.8 nM for Ink-128 and E2, respectively, is the $EC_{50}$ (i.e., Fa=0.5). In sum, the combination dose is nearly single digit nanomolar for each compound and in other experiments it has been shown that the combination causes apoptosis in MB cell lines.

TABLE 10A

| Combo | $ED_{50}$ | $ED_{75}$ | $ED_{90}$ | $ED_{95}$ |
| --- | --- | --- | --- | --- |
| Ink + E2 | 0.71744 | 0.61305 | 0.53344 | 0.49055 |

TABLE 10B

| Drug/Combo | CI value | Dose Ink | Dose E2 |
| --- | --- | --- | --- |
| Ink |  | 0.00613 |  |
| E2 |  |  | 0.06345 |
| INK + E2 | 0.71744 | 0.00297 | 0.041483 | k. SUFO-KO Light Assays Using Anti-C-Myc Antibody

Figure 16:
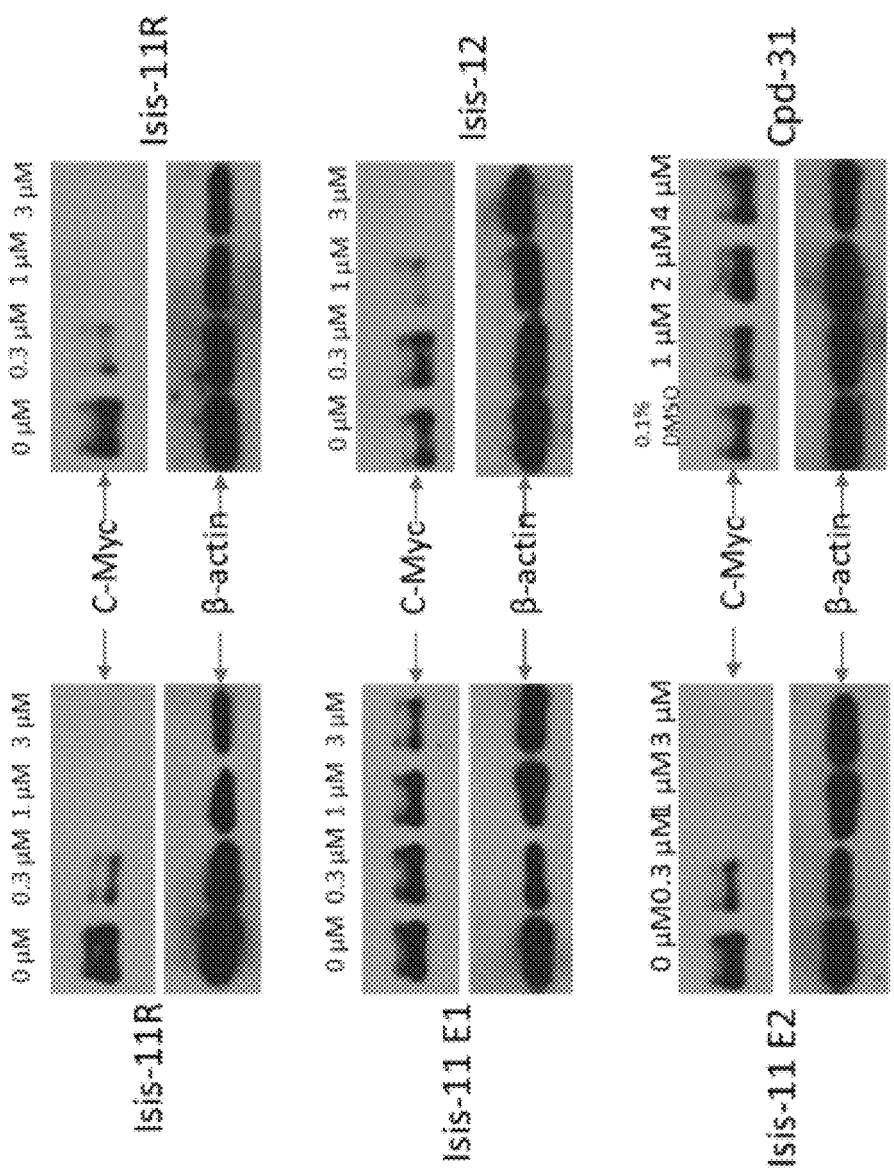
FIG. 16 shows representative data illustrating treatment of SUFU-KO-Light cells with Isis-11R (racemic), Isis-11-E1, Isis-11-E2, Isis-11R (racemic-repeat), Isis-12, and Cpd-31 (non-translational control) for 24 hours followed by western blotting assay with Anti-C-Myc antibody.

Referring to FIG. 16, SUFO-KO-Light cells were treated with compounds as indicated for 24 hours followed by western blot assay with Anti-C-Myc antibody. The racemic Isis-11 is repeated as shown, compound-31 is a negative control for this cell line.

Isis-11 isomers have different effects on c-Myc in all cell lines. Stereochemical selectivity is a hallmark of specific acting compounds.

l. Hedgehog Pathway Inhibition

Without wishing to be bound by theory, Isis-11 (racemic) inhibits the activity of Hedgehog signaling in cell-based assays of the Gli transcription factors. The hedgehog inhibition potency is ~ $EC_{50}$=100 nM in a cell-based reporter sensitive to Shh ligand and also in separate cell-based reports derived from fibroblast SUFU knockouts that decouple Gli activity from the G-protein smoothened. Without wishing to be bound by theory, this latter activity may indicate that the hedgehog inhibition of Isis-11 (racemic) and related compounds affects elements of the pathway downstream of smoothened, a particularly desirable activity as such compounds would be active against smoothened resistance mutants, and active against cancer stem cells arising from resistance to standard chemotherapy. Western blots of Gli1 protein in SUFU-KO-Light cells indicate that Isis-11 directly affects the levels of Gli1 protein rather than an indirect effect on Hedgehog signaling.

3. Evaluation of Benzimidazole Analogs as Coronavirus Translation Inhibitors

Without wishing to be bound by theory, benzimidazole analogs have demonstrated activity as coronavirus translation inhibition agents. Coronaviruses are single-stranded, RNA viruses with a large genome in which mutations are very common. There are six human types of coronavirus: 229E, OC43, NL63, HKU1, which are often associated with mild upper respiratory tract infections, as well as the virus causing severe acute respiratory syndrome (SARS-CoV), Middle East respiratory syndrome (MERS-CoV), and severe acute respiratory syndrome coronavirus 2 (SARS-CoV-2), each of which are zoonotic but have also caused human disease. Interspecies transmission and the resulting emergent coronaviruses have been important factors in emerging respiratory disease as coronaviruses are known to infect feline, swine, canine, and bat species. Indeed, MERS-CoV, SARS-CoV, and SARS-CoV-2 emerged from animal reservoirs and are now increasingly important respiratory virus threats. To date, over 1 million cases of SARS-CoV-2 have been confirmed in humans, resulting in over 74,000 deaths.

Figure 17:
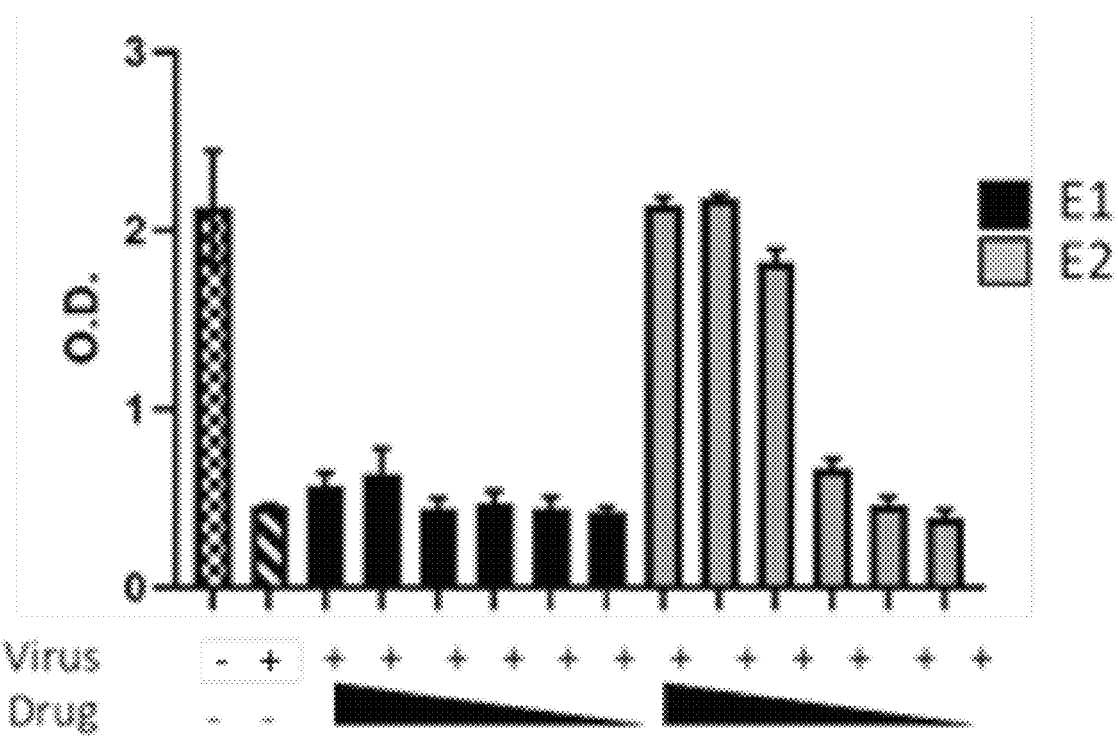
FIG. 17 shows representative data illustrating Isis-11-E1 and Isis-11-E2 inhibition of cell death in SARS-CoV-2-infected Vero E6 cells.
Figure 18:
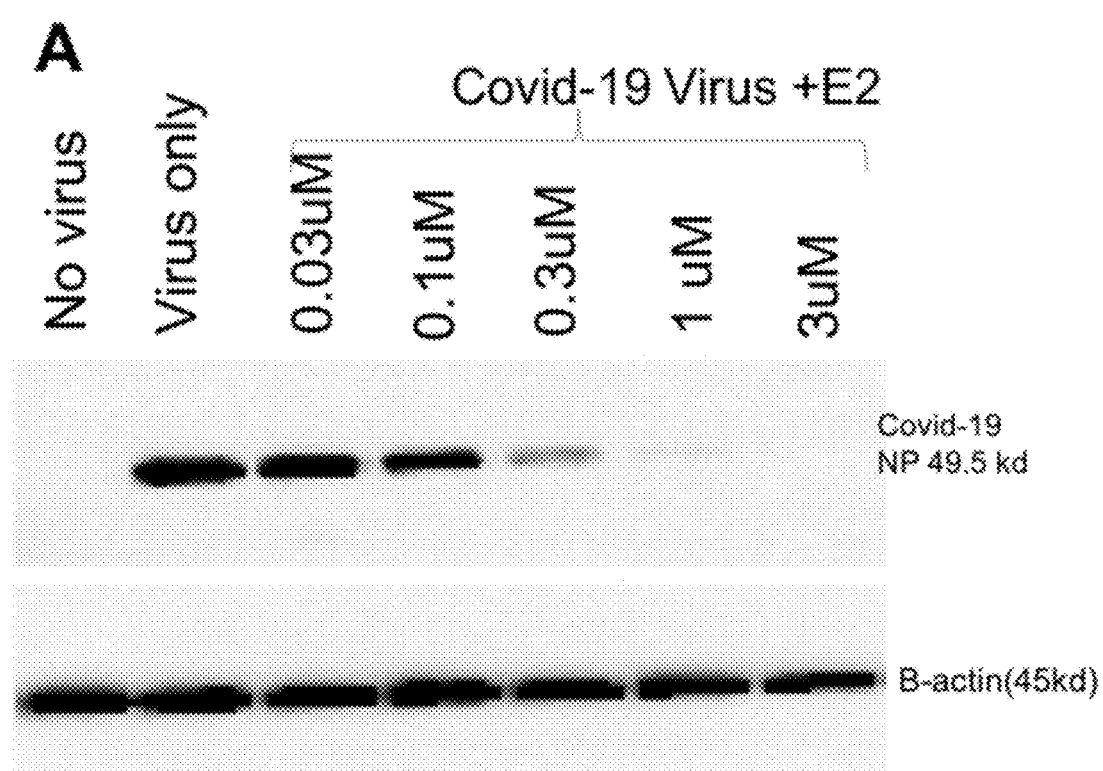
FIG. 18 shows the reduction of SARS-CoV-2 nucleocapsid protein levels upon treatment of viral infected Vero cells with Isis-11-E2 for 24 hours post-infection.
Figure 19:
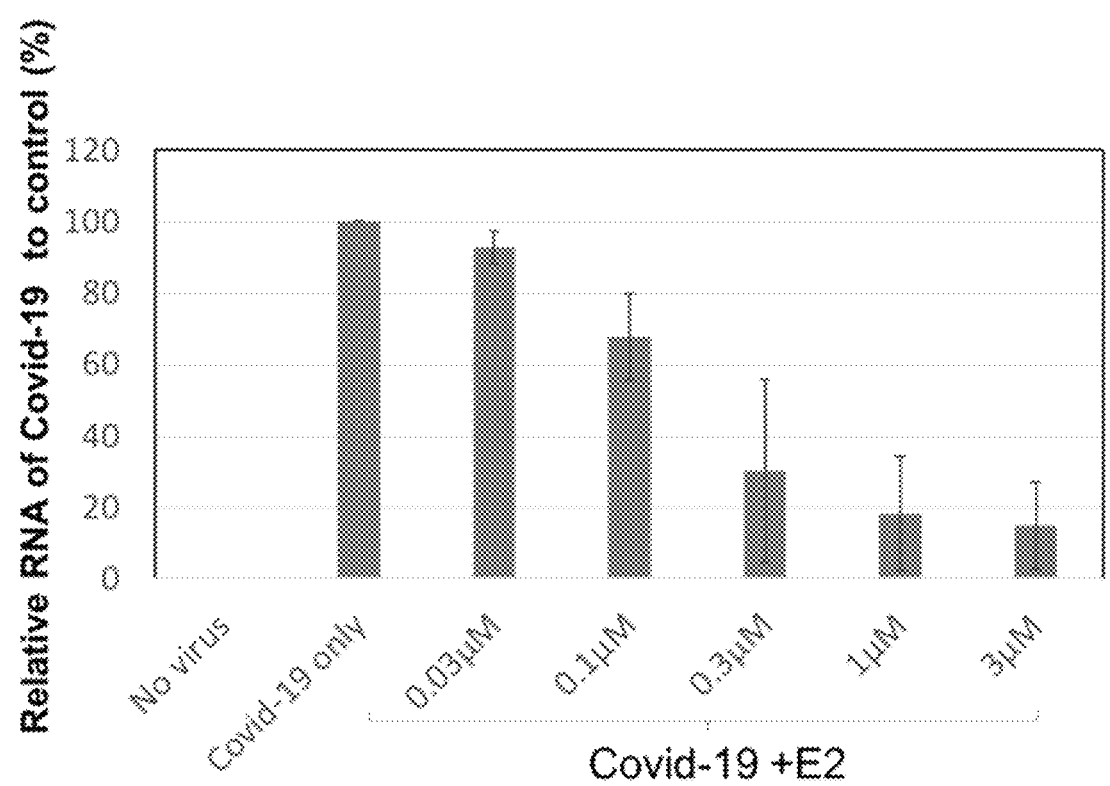
FIG. 19 show the reduction of SARS-CoV-2 viral RNA upon treatment of viral infected Vero cells with Isis-11-E2 for 24 hours post-infection.

Here, E1 and E2 were tested at 6 concentrations for inhibition of cell death in SARS-CoV-2-infected Vero E6 cells. This experiment was conducted with triplicate wells, with compound added 1 hour before infection and kept in the wells for 48 hours. At that point, XTT reagent is added and O.D. is read (higher O.D.=more live cells). As shown in FIG. 17, E2 inhibited cell death with an $EC_{50}$=0.142 micromolar (Table 1) while the enantiomeric compound E1 had no effect on viral replication over this concentration range. The specific effect on viral protein and on genomic viral RNA is shown in FIG. 18 and in FIG. 19. The Western blot for SARS-CoV-2 nucleocapsid protein shows a dose-dependent reduction of viral protein with no effect on the levels of β-actin protein in the viral infected Vero cells. Further confirmation of a selective effect on virus levels is indicated in FIG. 19, which shows that viral RNA is decreased with the same concentration dependence of Isis-11-E2 as for the reduction in cellular toxicity (CPE) as shown in FIG. 17.

4. Exemplary Benzimidazole Analogs

A list of compounds evaluated for activity is shown in Table 11 below.

The Isis compounds are described in Seth et al. (2005) J. Med. Chem; the IBIS compounds are described in Seth et al. U.S. Pat. No. 7,642,265.

TABLE 11

| No. | Structure |
| --- | --- |
| BCX4430 | (structure of BCX4430) |

TABLE 11-continued

| No. | Structure |
|---|---|
| JQ1 | 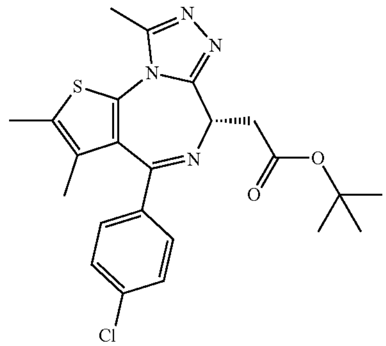 [SMILES: Cc1sc2c(c1C)C(c1ccc(Cl)cc1)=N[C@@H](CC(=O)OC(C)(C)C)c1nnc(C)n1-2] |
| Ink-128 | 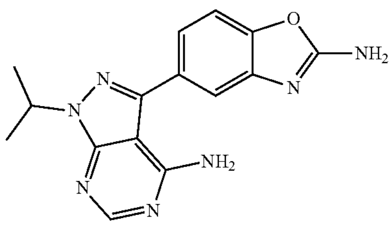 [SMILES: CC(C)n1nc(-c2ccc3oc(N)nc3c2)c2c(N)ncnc21] |
| Isis-11 (R or racemic) | 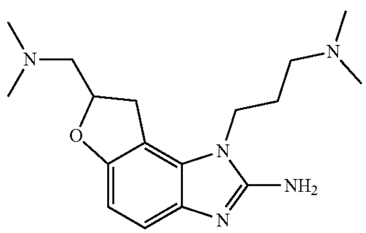 |
| Isis-11 (E1 or + isomer) | 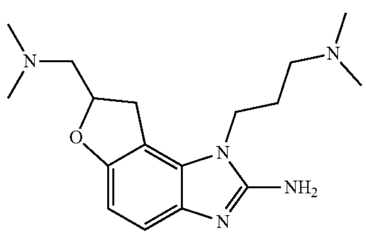 |
| Isis-11 (E2 or − isomer) | 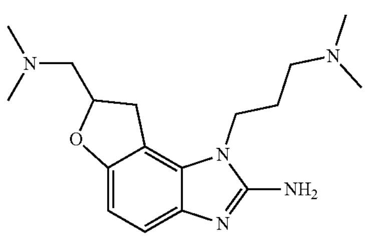 |
| DD041 | 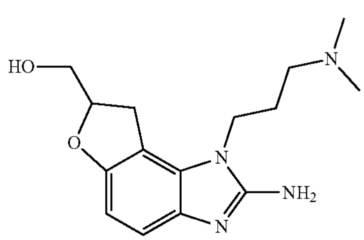 [SMILES: CN(C)CCCn1c(N)nc2ccc3c(c21)CC(CO)O3] |
| Isis-12 | 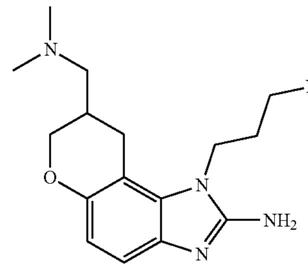 |
| Isis-13 | 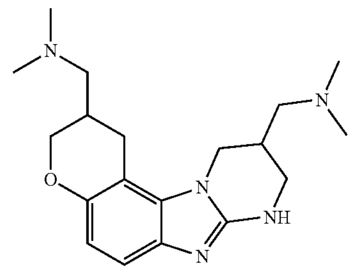 |
| Isis-4 | 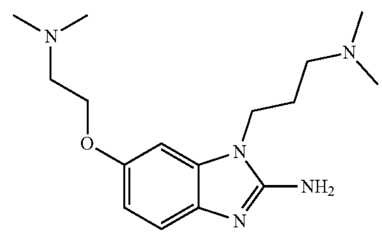 |
| IBIS-528637 | 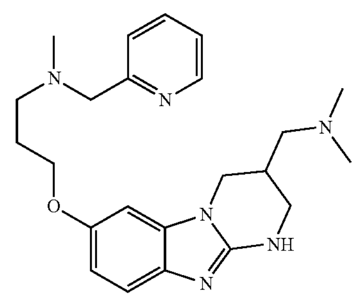 [SMILES: CN(C)CC1CNc2nc3ccc(OCCCN(C)Cc4ccccn4)cc3n2C1] |
| IBIS-561075 | 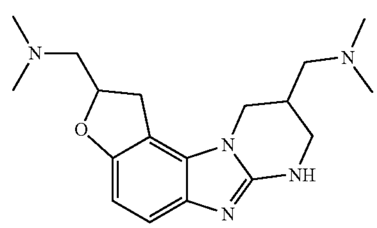 |

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for treating a disorder of uncontrolled cellular proliferation in a subject, the method comprising administering to the subject an effective amount of a compound having a structure represented by a formula selected from:

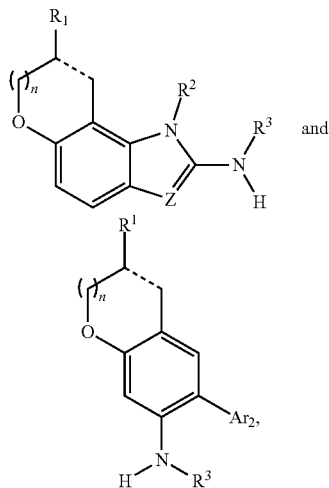

wherein ⟋ is a single or a double covalent bond;
wherein n is 0 or 1;
wherein Z, when present, is selected from N and $CR^{10}$;
  wherein $R^{10}$, when present, is selected from hydrogen and halogen;
wherein $R^1$ is selected from —(C1-C4 alkyl)$OR^{11}$, —(C1-C4 alkyl)$NR^{12a}R^{12b}$, —$CO_2R^{13}$, and —C(O)$NR^{14a}R^{14b}$;
  wherein each of $R^{11}$, $R^{12a}$, and $R^{12b}$, when present, is independently selected from hydrogen, C1-C4 alkyl, —C(=NH)$NH_2$, —$CO_2$(C1-C4 alkyl), —(C1-C4 alkyl)$OR^{20}$, —(C1-C4 alkyl)$NR^{21a}R^{21b}$, —(C1-C4 alkyl)$Ar^1$, and $Ar^1$;
    wherein $Ar^1$, when present, is selected from aryl and heteroaryl and substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino;
  wherein each of $R^{13}$, $R^{14a}$, and $R^{14b}$, when present, is independently selected from hydrogen and C1-C4 alkyl;
wherein $R^2$, when present, is selected from C1-C4 alkyl and —(C1-C4 alkyl)$NR^{15a}R^{15b}$;
  wherein each of $R^{15a}$ and $R^{15b}$, when present, is independently selected from hydrogen and C1-C4 alkyl;
wherein $R^3$ is selected from hydrogen and C1-C4 alkyl;
or wherein each of $R^2$, when present, and $R^3$ together comprise a 5- to 6-membered heterocycle substituted with a group selected from C1-C4 alkyl and —(C1-C4 alkyl)$NR^{16a}R^{16b}$
  wherein each of $R^{16a}$ and $R^{16b}$, when present, is independently selected from hydrogen and C1-C4 alkyl; and
wherein $Ar^2$ is a heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, or a pharmaceutically acceptable salt thereof, wherein treating is one or more selected from active treatment, causal treatment, palliative treatment, and supportive treatment.

2. The method of claim 1, wherein the compound has a structure represented by a formula:

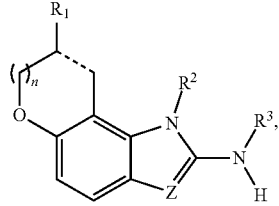

or a pharmaceutically acceptable salt thereof.

3. The method of claim 2, wherein the compound has a structure represented by a formula:

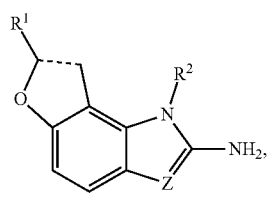

or a pharmaceutically acceptable salt thereof.

4. The method of claim 1, wherein the compound has a structure represented by a formula:

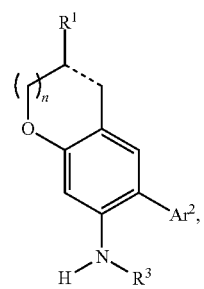

or a pharmaceutically acceptable salt thereof.

5. The method of claim 4, wherein the compound has a structure represented by a formula:

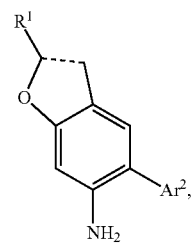

or a pharmaceutically acceptable salt thereof.

6. The method of claim 1, wherein the compound is selected from:
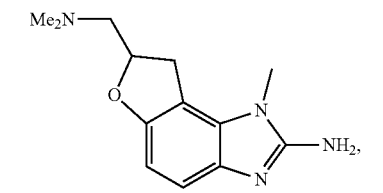
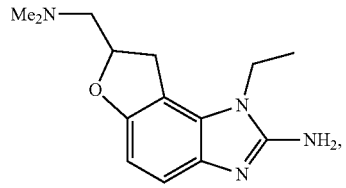
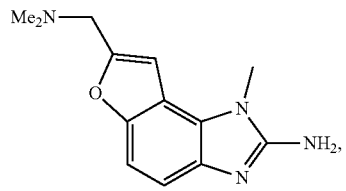
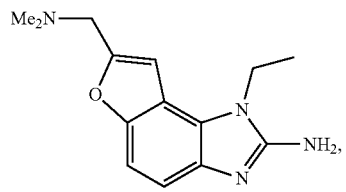
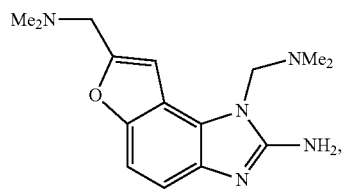
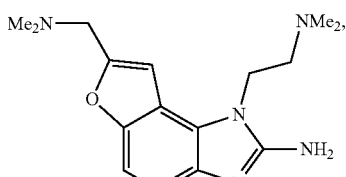
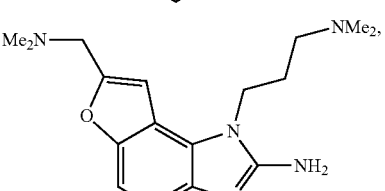
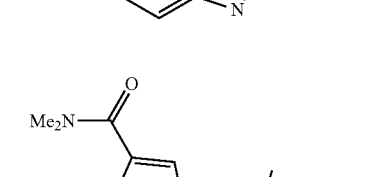
-continued
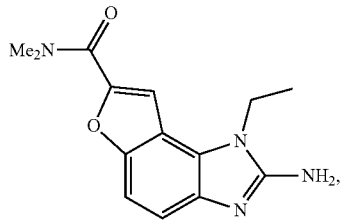
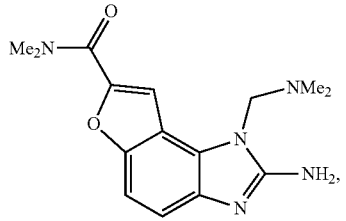
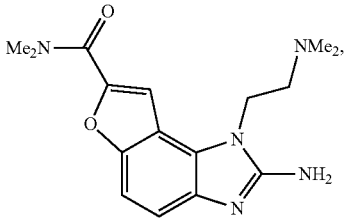
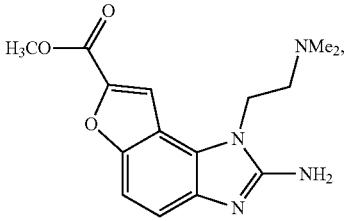
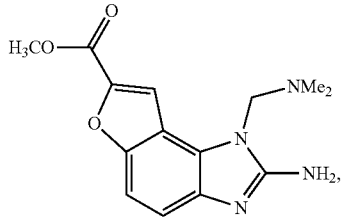
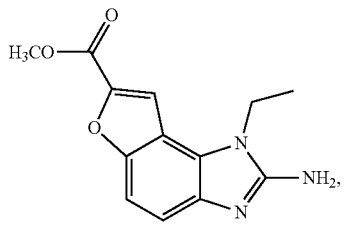
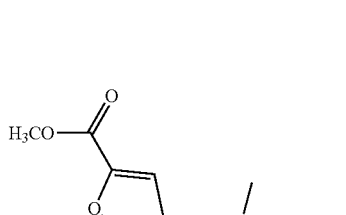

-continued

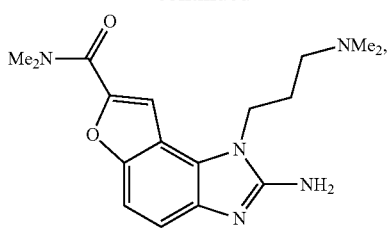
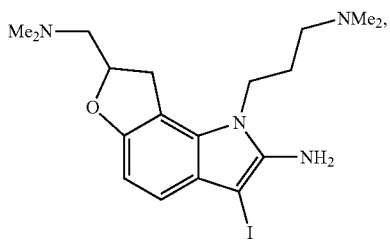
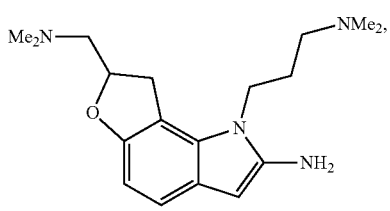
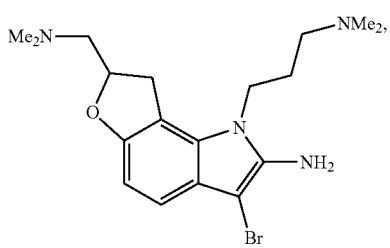
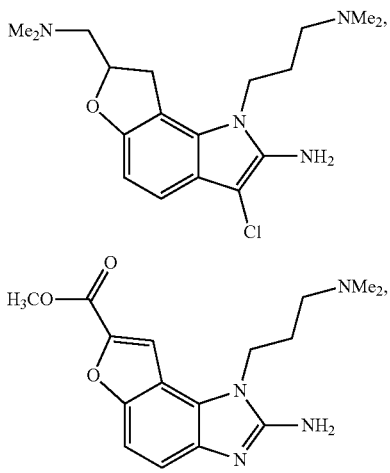
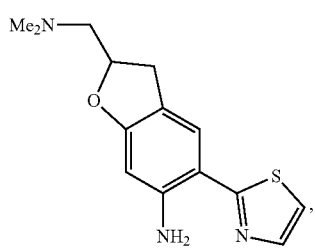

-continued

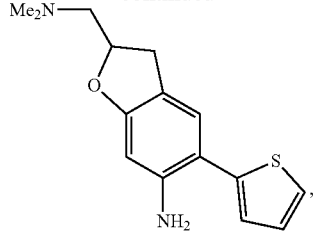
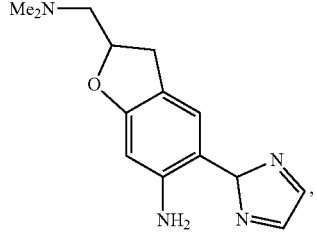
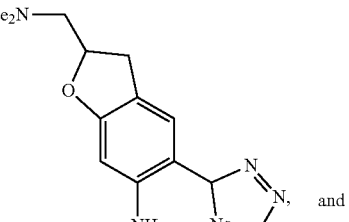
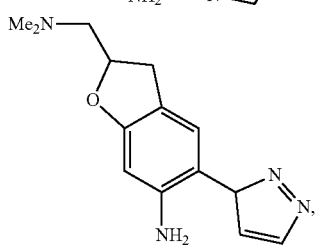

or a pharmaceutically acceptable salt thereof.

7. The method of claim 1, wherein the compound is:

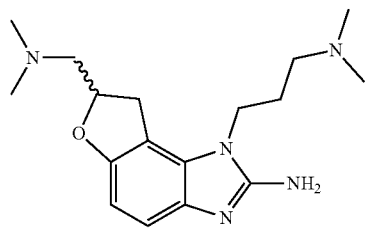

or a pharmaceutically acceptable salt thereof.

8. The method of claim 1, wherein the disorder is a cancer.

9. The method of claim 8, wherein the cancer is selected from a sarcoma, a carcinoma, a hematological cancer, a solid tumor, breast cancer, cervical cancer, gastrointestinal cancer, colorectal cancer, brain cancer, skin cancer, prostate cancer, ovarian cancer, non-small cell lung carcinoma, thyroid cancer, testicular cancer, pancreatic cancer, endometrial cancer, melanoma, glioma, medulloblastoma, leukemia, lymphoma, chronic myeloproliferative disorder, myelodysplastic syndrome, myeloproliferative neoplasm, and plasma cell neoplasm (myeloma).

10. The method of claim 8, wherein the cancer is a liver cancer.

11. A method for treating a RNA virus infection in a subject, the method comprising administering to the subject an effective amount of a compound having a structure represented by a formula selected from:

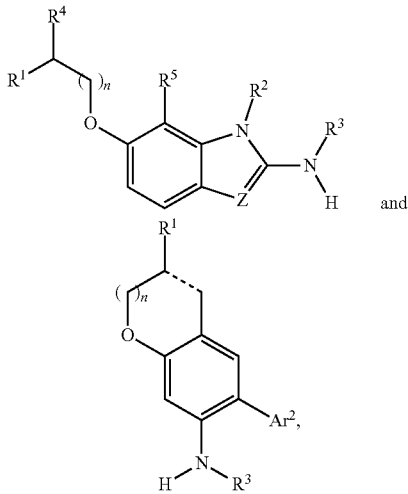

and 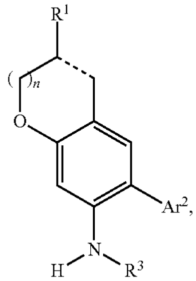 wherein - - - is a single or a double covalent bond;

wherein n is 0 or 1;
wherein Z, when present, is selected from N and $CR^{10}$;

wherein $R^{10}$, when present, is selected from hydrogen and halogen;

wherein $R^1$ is selected from —(C1-C4 alkyl)$OR^{11}$, —(C1-C4 alkyl)$NR^{12a}R^{12b}$, —$CO_2R^{13}$, and —C(O)$NR^{14a}R^{14b}$;

wherein each of $R^{11}$, $R^{12a}$, and $R^{12b}$, when present, is independently selected from hydrogen, C1-C4 alkyl, —C(=NH)$NH_2$, —$CO_2$(C1-C4 alkyl), —(C1-C4 alkyl)$OR^{20}$, —(C1-C4 alkyl)$NR^{21a}R^{21b}$, —(C1-C4 alkyl)$Ar^1$, and $Ar^1$;

wherein $Ar^1$, when present, is selected from aryl and heteroaryl and substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino;

wherein each of $R^{13}$, $R^{14a}$, and $R^{14b}$, when present, is independently selected from hydrogen and C1-C4 alkyl;

wherein $R^2$, when present, is selected from C1-C4 alkyl and —(C1-C4 alkyl)$NR^{15a}R^{15b}$;

wherein each of $R^{15a}$ and $R^{15b}$, when present, is independently selected from hydrogen and C1-C4 alkyl;

wherein $R^3$ is selected from hydrogen and C1-C4 alkyl;
or wherein each of $R^2$, when present, and $R^3$ together comprise a 5- to 6-membered heterocycle substituted with a group selected from C1-C4 alkyl and —(C1-C4 alkyl)$NR^{16a}R^{16b}$;

wherein each of $R^{16a}$ and $R^{16b}$, when present, is independently selected from hydrogen and C1-C4 alkyl;

wherein each of $R^4$ and $R^5$ is hydrogen or together comprise a 5- to 6-membered heterocycle; and wherein $Ar^2$ is a heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, and (C1-C4)(C1-C4) dialkylamino, provided that when each of $R^4$ and $R^5$ is hydrogen, then R is —(C1-C4 alkyl)$OR^{11}$ or —(C1-C4 alkyl)$NR^{12a}R^{12b}$;

or a pharmaceutically acceptable salt thereof, wherein the RNA virus is selected from Zika virus, dengue virus, Powassan virus, Chikungunya virus, Enterovirus, respiratory syntactical virus (RSV), Rift Valley fever, Influenza virus, Tacaribe virus, Mayaro virus, West Nile virus, yellow fever virus, and coronavirus, and wherein treating is one or more selected from active treatment, causal treatment, palliative treatment, and supportive treatment.

12. The method of claim 11, wherein the coronavirus is severe acute respiratory syndrome coronavirus 2 (SARS-CoV-2).

* * * * *